US012544373B2

(12) United States Patent
Farhan et al.

(10) Patent No.: US 12,544,373 B2
(45) Date of Patent: Feb. 10, 2026

(54) TREATMENT OF CANCER, INFLAMMATORY DISEASES AND AUTOIMMUNE DISEASES

(71) Applicant: Usher III Initiative, Inc., Chicago, IL (US)

(72) Inventors: Mahdi Farhan, Chicago, IL (US); James M. Hamby, Chicago, IL (US); Tracey L. Fletcher, Chicago, IL (US)

(73) Assignee: Usher III Initiative, Inc., Chicago, IL (US)

( * ) Notice: Subject to any disclaimer, the term of this patent is extended or adjusted under 35 U.S.C. 154(b) by 512 days.

(21) Appl. No.: 18/093,599

(22) Filed: Jan. 5, 2023

(65) Prior Publication Data

US 2023/0149399 A1 May 18, 2023

Related U.S. Application Data

(63) Continuation of application No. PCT/US2021/040810, filed on Jul. 8, 2021.

(60) Provisional application No. 63/049,948, filed on Jul. 9, 2020.

(51) Int. Cl.

| | |
|---|---|
| ***A61K 31/5025*** | (2006.01) |
| ***A61K 45/06*** | (2006.01) |
| ***A61P 1/00*** | (2006.01) |
| ***A61P 1/18*** | (2006.01) |
| ***A61P 13/08*** | (2006.01) |
| ***A61P 15/08*** | (2006.01) |
| ***A61P 17/00*** | (2006.01) |
| ***A61P 19/08*** | (2006.01) |
| ***A61P 25/00*** | (2006.01) |
| ***A61P 35/00*** | (2006.01) |

(52) U.S. Cl.

CPC .......... *A61K 31/5025* (2013.01); *A61K 45/06* (2013.01); *A61P 1/00* (2018.01); *A61P 1/18* (2018.01); *A61P 13/08* (2018.01); *A61P 15/08* (2018.01); *A61P 17/00* (2018.01); *A61P 19/08* (2018.01); *A61P 25/00* (2018.01); *A61P 35/00* (2018.01)

(58) Field of Classification Search

None

See application file for complete search history.

(56) References Cited

U.S. PATENT DOCUMENTS

| | | | |
|---|---|---|---|
| 7,390,808 | B2 | 6/2008 | Green et al. |
| 7,666,647 | B2 | 2/2010 | Ter Haar et al. |
| 7,812,166 | B2 | 10/2010 | Dai et al. |
| 7,883,881 | B2 | 2/2011 | Ter Haar et al. |
| 8,318,467 | B2 | 11/2012 | Ter Haar et al. |
| 8,338,439 | B2 | 12/2012 | Singh et al. |
| 8,450,335 | B2 | 5/2013 | Singh et al. |
| 8,609,679 | B2 | 12/2013 | Singh et al. |
| 8,765,762 | B2 | 7/2014 | Bürli et al. |
| 8,785,391 | B2 | 7/2014 | Johansson |
| 9,079,909 | B2 | 7/2015 | Bürli et al. |
| 9,212,181 | B2 | 12/2015 | Singh et al. |
| 9,227,976 | B2 | 1/2016 | Bürli et al. |
| 9,260,381 | B2 | 2/2016 | Bürli et al. |
| 9,371,332 | B2 | 6/2016 | Bürli et al. |
| 9,549,910 | B2 | 1/2017 | Bürli et al. |
| 9,783,545 | B2 | 10/2017 | Bürli et al. |
| 9,925,187 | B2 | 3/2018 | Bürli et al. |
| 10,307,422 | B2 | 6/2019 | Bürli et al. |
| 2008/0194562 | A1 | 8/2008 | Wyatt et al. |
| 2010/0029610 | A1 | 2/2010 | Singh et al. |
| 2013/0065879 | A1 | 3/2013 | Singh et al. |
| 2013/0065899 | A1 | 3/2013 | Singh et al. |
| 2013/0072469 | A1 | 3/2013 | Singh et al. |
| 2013/0165462 | A1 | 6/2013 | Singh et al. |
| 2013/0252936 | A1 | 9/2013 | Bürli et al. |
| 2014/0121197 | A1 | 5/2014 | Bürli et al. |
| 2014/0121205 | A1 | 5/2014 | Bürli et al. |
| 2014/0288005 | A1 | 9/2014 | Johansson |
| 2014/0288093 | A1 | 9/2014 | Krainc et al. |
| 2015/0265617 | A1 | 9/2015 | Bürli et al. |
| 2015/0266812 | A1 | 9/2015 | Bürli et al. |
| 2016/0158172 | A1 | 6/2016 | Bürli et al. |
| 2016/0272647 | A1 | 9/2016 | Bürli et al. |
| 2017/0143718 | A1 | 5/2017 | Bürli et al. |
| 2018/0099974 | A1 | 4/2018 | Saperstein |
| 2018/0207159 | A1 | 7/2018 | Bürli et al. |
| 2024/0279229 | A1 | 8/2024 | Saperstein |

FOREIGN PATENT DOCUMENTS

| | | | |
|---|---|---|---|
| JP | 2014515758 | A | 7/2014 |
| WO | WO-03080616 | A1 | 10/2003 |
| WO | WO-2006077401 | A1 | 7/2006 |
| WO | WO-2006091246 | A1 | 8/2006 |

(Continued)

OTHER PUBLICATIONS

Vocka, M. et al., "Novel serum markers HSP60, CHI3L1, and IGFBP-2 in metastatic colorectal cancer," Oncology Letters, 18:6284-6292 (2019).

Alagramam, K. N. et al., "A Small Molecule Mitigates Hearing Loss in a Mouse Model of Usher Syndrome III," Nature Chemical Biology, Jun. 2016, vol. 12, No. 6, pp. 444-451.

Brana, M. F. et al., "Pyrazolo[3,4-c]pyridazines as Novel and Selective Inhibitors of Cyclin-dependent Kinases," Journal of Medicinal Chemistry, Nov. 2005, vol. 48, No. 22, pp. 6843-6854.

Churcher, I. "Tau Therapeutic Strategies for the Treatment of Alzheimer's Disease," Current Topics in Medicinal Chemistry, 2006, vol. 6, No. 6, pp. 579-595.

(Continued)

*Primary Examiner* — Brian J Davis

(74) *Attorney, Agent, or Firm* — COOLEY LLP

(57) ABSTRACT

The present disclosure relates to methods for the treatment or prevention of cancer, an inflammatory disease or an autoimmune disease with compounds of the invention as disclosed herein. The present disclosure also relates to methods for reducing risk of developing cancer, an inflammatory disease or an autoimmune disease with compounds of the invention as disclosed herein.

22 Claims, No Drawings

(56) References Cited

FOREIGN PATENT DOCUMENTS

| | | | |
|---|---|---|---|
| WO | WO-2006127396 | A1 | 11/2006 |
| WO | WO-2007075911 | A2 | 7/2007 |
| WO | WO-2007120827 | A2 | 10/2007 |
| WO | WO-2008051757 | A1 | 5/2008 |
| WO | WO-2009039420 | A1 | 3/2009 |
| WO | WO-2009062118 | A2 | 5/2009 |
| WO | WO-2010046013 | A1 | 4/2010 |
| WO | WO-2012148994 | A1 | 11/2012 |
| WO | WO-2014066835 | A1 | 5/2014 |
| WO | WO-2014066836 | A1 | 5/2014 |
| WO | WO-2014121205 | A1 | 8/2014 |
| WO | WO-2016201266 | A1 | 12/2016 |
| WO | WO-2017098367 | A1 | 6/2017 |
| WO | WO-2022011091 | A1 | 1/2022 |

OTHER PUBLICATIONS

El-Amraoui, A. et al., "Usher I Syndrome: Unravelling the Mechanisms That Underlie the Cohesion of the Growing Hair Bundle in Inner Ear Sensory Cells," Journal of Cell Science, Oct. 2005, vol. 118(Pt 20), pp. 4593-4603.

Geng, R. et al., "Noddy, a Mouse Harboring a Missense Mutation in Protocadherin-15, Reveals the Impact of Disrupting a Critical Interaction Site Between Tip-link Cadherins in Inner Ear Hair Cells," The Journal of Neuroscience, Mar. 2013, vol. 33, No. 10, pp. 4395-4404.

Geng, R. et al., "The Mechanosensory Structure of the Hair Cell Requires Clarin-1, a Protein Encoded by Usher Syndrome III Causative Gene," The Journal of Neuroscience, Jul. 2012, vol. 32, No. 28, pp. 9485-9498.

Geng, R. et al., "Usher Syndrome IIIA Gene Clarin-1 is Essential for Hair Cell Function and Associated Neural Activation," Human Molecular Genetics, Aug. 2009, vol. 18, No. 15, pp. 2748-2760.

International Preliminary Report on Patentability for International Application No. PCT/US2021/040810 dated Jan. 19, 2023, 8 pages.

International Search Report and Written Opinion for International Application No. PCT/US2012/034959, mailed Sep. 21, 2012, 10 pages.

International Search Report and Written Opinion for International Application No. PCT/US2013/066938, mailed Jan. 30, 2014, 6 pages.

International Search Report and Written Opinion for International Application No. PCT/US2013/066939, mailed Mar. 5, 2014, 8 pages.

International Search Report and Written Opinion for International Application No. PCT/US2016/036945, mailed Sep. 7, 2016, 12 pages.

International Search Report and Written Opinion for International Application No. PCT/US2021/040810 dated Dec. 15, 2021, 11 pages.

Office Action for U.S. Appl. No. 13/791,205, mailed Aug. 6, 2014, 7 pages.

Office Action for U.S. Appl. No. 13/791,744, mailed Jun. 27, 2014, 9 pages.

Office Action for U.S. Appl. No. 14/731,535, mailed Oct. 5, 2015, 6 pages.

Office Action for U.S. Appl. No. 15/141,949, mailed Feb. 3, 2017, 6 pages.

Office Action for U.S. Appl. No. 15/924,831, mailed Dec. 19, 2018, 5 pages.

Shelkovnikova, T. A. et al., "Proteinopathies, neurodegenerative disorders with protein aggregation-based pathology," Molecular Biology, vol. 46, No. 3, pp. 362-374 (Jun. 2012).

Tian, G. et al., "Clarin-1, Encoded by the Usher Syndrome III Causative Gene, Forms a Membranous Microdomain: Possible Role of Clarin-1 in Organizing the Actin Cytoskeleton," The Journal of Biological Chemistry, Jul. 2009, vol. 284, No. 28, pp. 18980-18993.

Tian, G. et al., "Impairment of vision in a mouse model of Usher Syndrome Type III," Investigative Ophthalmology & Visual Science, Mar. 2016, vol. 57, 866-875. doi:10.1167/iovs.15-16946.

Tretyakov, E. V. et al., "Investigations of the Richter reaction in a series of vicinal alkynylpyrazolediazonium salts," J. Chem. Soc., Perkin Trans., vol. 1, No. 24, pp. 3721-3726 (1999).

Tretyakov, E. V. et al., "New findings in the Richter reaction in series of vicinal alkynylpyrazolyldiazonium salts," Heterocyclic Communications, vol. 4, No. 6, pp. 519-524 (1998).

Vasilevsky, S. F. et al., "Cinnolines and pyrazolopyridazines. Novel synthetic and mechanistic aspects of the Richter reaction," Liebigs Ann., vol. 5, pp. 775-779 (1995).

Becq, F. et al., "The rescue of F508del-CFTR by elexacaftor/tezacaftor/ivacaftor (Trikafta) in human airway epithelial cells is underestimated due to the presence of ivacaftor," Eur Respir J, (Feb. 2022); 59(2):2100671, 18 pages.

Bertrand, C. A. et al., "SLC26A9 is a constitutively active, CFTR-regulated anion conductance in human bronchial epithelia," J Gen Physiol. (Apr. 2009), 133(4):421-438.

Chan, C-H et al., "Transcript and in silico analysis of CLN3 in juvenile neuronal ceroid lipofuscinosis and associated mouse models," Human Molecular Genetics, 2008, vol. 17, No. 21, pp. 3332-3339. doi:10.1093/hmg/ddn228.

Fauvet, B. et al., "Repair or Degrade: the Thermodynamic Dilemma of Cellular Protein Quality-Control," Frontiers in Molecular Biosciences, vol. 8, Article 768888, Oct. 2021, 11 pages.

Fiedorczuk, K. et al., "Molecular structures reveal synergistic rescue of A508 Cftr by Trikafta modulators," Science, (Oct. 2022), 378(6617):284-290.

Gomez-Giro, G. et al., "Synapse alterations precede neuronal damage and storage pathology in a human cerebral organoid model of CLN3-juvenile neuronal ceroid lipofuscinosis," Acta Neuropathologica Communications (2019) 7:222, 19 pages.

Laselva, O. et al., "Rescue of multiple class II CFTR mutations by elexacaftor+tezacaftor+ivacaftor mediated in part by the dual activities of elexacaftor as both corrector and potentiator," Eur Respir J. (Jun. 2021), 57(6):2002774, 13 pages.

Ostergaard, J. R., "Juvenile neuronal ceroid lipofuscinosis (Batten disease): current insights," Degenerative Neurological and Neuromuscular Disease 2016:6, pp. 73-83.

Singh, M. K. et al., "Molecular Chaperonin HSP60: Current Understanding and Future Prospects," Int. J. Mol. Sci. 2024, 25, 5483, 25 pages.

Stefl, S. et al., "Molecular mechanisms of disease-causing missense mutations," J Mol Biol. Nov. 1, 2013; 425(21):3919-3936. doi:10.1016/j.jmb.2013.07.014.

Van Goor, F. et al., "Rescue of CF airway epithelial cell function in vitro by a CFTR potentiator, VX-770," Proc Natl Acad Sci USA, (Nov. 2009), 106(44):18825-18830.

Carrell, R.W., et al., "Alpha1-antitrypsin Deficiency—a Model for Conformational Diseases," The New England Journal of Medicine, Jan. 3, 2002, vol. 346(1), pp. 45-53.

Dichgans, M., et al., "Small in-frame Deletions and Missense Mutations in Cadasil: 3D Models Predict Misfolding of Notch3 EGF-like Repeat Domains," European Journal of Human Genetics, Apr. 2000, vol. 8(4), pp. 280-285.

Dietz, H. C., et al., "Marfan Syndrome Caused by a Recurrent De Novo Missense Mutation in the Fibrillin Gene," Nature, Jul. 25, 1991, vol. 352 (6333), pp. 337-339.

Gao, H., et al., "Mutations in a Novel CLN6-Encoded Transmembrane Protein Cause Variant Neuronal Ceroid Lipofuscinosis in Man and Mouse," American Journal of Human Genetics, Feb. 2002, vol. 70 (2), pp. 324-335.

Menaa, F., "Stroke in Sickle Cell Anemia Patients: a Need for Multidisciplinary Approaches," Atherosclerosis, Aug. 2013, vol. 229(2), pp. 496-503.

Meriin, A. B., and Sherman, M. Y., "Role of Molecular Chaperones in Neurodegenerative Disorders," International Journal of Hyperthermia, Aug. 2005, vol. 21(5), pp. 403-419.

Polymeropoulos, M.H., et al., "Mutation in the Alpha-synuclein Gene Identified in Families With Parkinson's Disease," Science, Jun. 27, 1997, vol. 276(6321), pp. 2045-2047.

(56) References Cited

OTHER PUBLICATIONS

Ranta, S., et al., "The Neuronal Ceroid Lipofuscinoses in Human EPMR and mnd Mutant Mice are Associated with Mutations in CLN8," Nature Genetics, Oct. 1999, vol. 23(2), pp. 233-236.
Savukoski, M., et al., "CLN5, a Novel Gene Encoding a Putative Transmembrane Protein Mutated in Finnish Variant Late Infantile Neuronal Ceroid Lipofuscinosis," Nature Genetics, Jul. 1998, vol. 19(3), pp. 286-288.
Sleat, D.E., et al., "Association of Mutations in a Lysosomal Protein With Classical Late-infantile Neuronal Ceroid Lipofuscinosis," Science, Sep. 19, 1997, vol. 277 (5333), pp. 1802-1805.
Tang, G., et al., "Autophagy Induced by Alexander Disease-Mutant GFAP Accumulation is Regulated by p38/MAPK and mTOR Signaling Pathways," Human Molecular Genetics, Jun. 1, 2008, vol. 17 (11), pp. 1540-1555.
Vesa, J., et al., "Mutations in the Palmitoyl Protein Thioesterase Gene Causing Infantile Neuronal Ceroid Lipofuscinosis," Nature, Aug. 17, 1995, vol. 376(6451), pp. 584-587.
Windpassinger, C., et al., "Heterozygous Missense Mutations in BSCL2 Are Associated With Distal Hereditary Motor Neuropathy and Silver Syndrome," Nature Genetics, Mar. 2004, vol. 36(3), pp. 271-276.

TREATMENT OF CANCER, INFLAMMATORY DISEASES AND AUTOIMMUNE DISEASES

CROSS-REFERENCE TO RELATED APPLICATIONS

This application is a continuation of international application no. PCT/US2021/040810, filed Jul. 8, 2021, which claims the benefit of U.S. Provisional Application No. 63/049,948, filed Jul. 9, 2020, the disclosure of each of which is incorporated by reference herein in its entirety.

BACKGROUND OF THE INVENTION

Cancer is one of the leading causes of death worldwide. In the United States alone, it is estimated that in 2020, more than 1.8 million new cancer cases will be diagnosed and more than 600,000 lives will be lost due to cancer. Cancer affects a large portion of the population—about 40% of people in the US will develop cancer in their lifetime. See "Cancer Costs and Figures" by the American Cancer Society. Inflammatory diseases and autoimmune diseases also afflict millions of people worldwide and remain a significant threat to people's health. While substantial progress in the treatment of these diseases have been made in recent years, there are still needs for identifying new methods for treating, preventing or reducing risk of developing cancer, inflammatory disease or autoimmune disease.

SUMMARY OF THE INVENTION

Each of a compound of Formula I, II, III, IV, V, VI, VII, XIII, XIV or XV; Compounds 1-35, 37-39, 42, 43, 44, 45, 46, 47-97, 98-123, 124a, 124b, 125-213, Va-Vz, Vaa-Vii, VIa-VIy, VIIa-VIId, XIIIa-XIIIz, XIVa or XVa-XVm; or a pharmaceutically acceptable salt of any of the foregoing, as disclosed herein, is a "compound of the invention".

The invention provides methods for treating cancer, preventing cancer, or reducing risk of developing cancer, comprising administering to a subject in need thereof an effective amount of a compound of Formula II:

Formula II

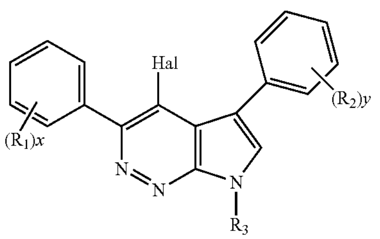

or a pharmaceutically acceptable salt thereof, wherein

Hal is —Cl, or —Br;

x is an integer ranging from 0 to 5;

each $R_1$ is independently —Cl, —F, —I, —Br, —$C_1$-$C_3$ alkyl, —O— $C_1$-$C_3$ alkyl, —CN, —$CF_3$, —C(O)NH($CH_3$), or —C≡$CCH_2OH$;

y is an integer ranging from 0 to 5;

each $R_2$ is independently —Cl, —F, —Br, —$C_1$-$C_3$ alkyl, —O—$C_1$-$C_3$ alkyl, —$CF_3$, —C(O)NH($CH_3$), or —C≡$CCH_2OH$;

$R_3$ is —H, —$C_1$-$C_6$ alkyl, —($C_1$-$C_6$ alkylene)-OH, —($C_1$-$C_6$ alkylene)-phenyl, —($C_1$-$C_6$ alkylene)-O—($C_1$-$C_6$ alkyl), —$C_2$-$C_6$ alkenyl), —$C_1$-$C_6$ alkylene)-C(O)$R_4$, —($C_1$-$C_6$alkylene)-$R_5$,

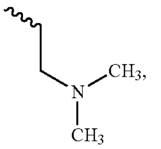
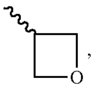
or
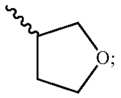

$R_4$ is —OH, —O—($C_1$-$C_6$ alkyl), —$NH_2$, —NH($C_1$-$C_6$ alkyl), —NH(($C_1$-$C_6$ alkylene)-OH), —NH(($C_1$-$C_6$alkylene)N($C_1$-$C_6$ alkyl)$_2$), —N($C_1$-$C_6$ alkyl)(($C_1$-$C_6$ alkylene)-CN), —N($C_1$-$C_6$ (alkyl)(($C_1$-$C_6$ alkylene) N($C_1$-$C_6$ alkyl)$_2$), —NH($C_1$-$C_6$ alkylene)-O—($C_1$-$C_6$ alkyl),

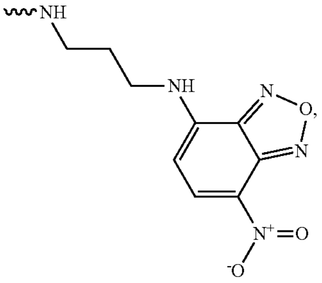
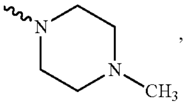
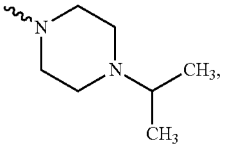
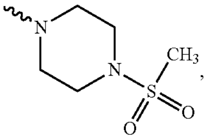
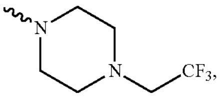
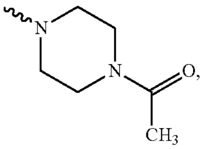
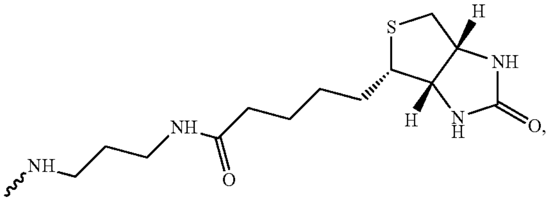
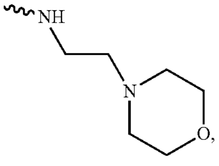
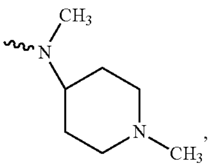
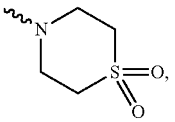
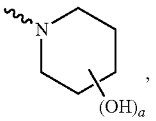
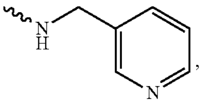
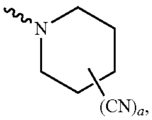
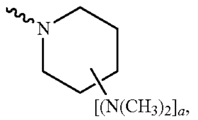

-continued

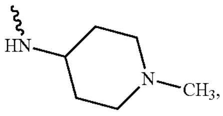
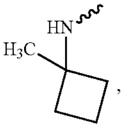,
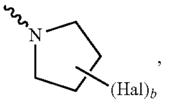,
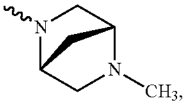
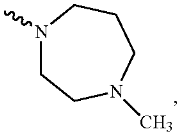,
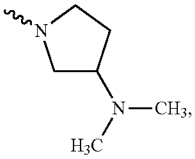
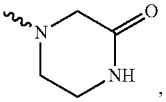,
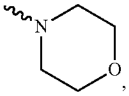
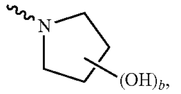, or
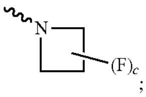;

a is an integer ranging from 0 to 10;

b is an integer ranging from 0 to 8;

c is an integer ranging from 0 to 6; and $R_5$ is

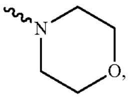
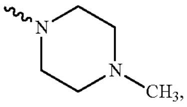
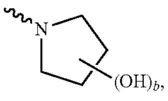, or
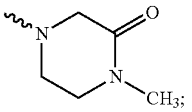;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention also provides methods for treating cancer, preventing cancer, or reducing risk of developing cancer, comprising administering to a subject in need thereof an effective amount of a compound of Formula III:

Formula III

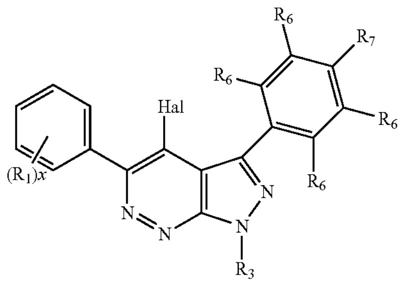

or a pharmaceutically acceptable salt thereof, wherein:

Hal is —Cl, —F, —I, or —Br;

x is an integer ranging from 0 to 5;

each $R_1$ is independently —Cl, —F, —I, —Br, —$C_1$-$C_3$ alkyl, —O—$C_1$-$C_3$ alkyl, —CN, —$CF_3$, —C(O)NH($CH_3$), or —C≡$CCH_2$OH;

$R_3$ is —H, —$C_1$-$C_6$ alkyl, —($C_1$-$C_6$ alkylene)-OH, —($C_1$-$C_6$ alkylene)-phenyl, —($C_1$-$C_6$ alkylene)-O—($C_1$-$C_6$ alkyl), —($C_1$-$C_6$ alkenyl, —$C_2$-$C_6$ alkylene)-C(O)$R_4$, —($C_1$-$C_6$ alkylene)-$R_5$.

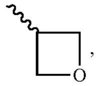, or
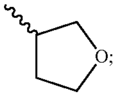;

$R_4$ is —OH, —O—($C_1$-$C_6$ alkyl), —$NH_2$, —NH($C_1$-$C_6$ alkyl), —NH(($C_1$-$C_6$ alkylene)-OH), —NH(($C_1$-$C_6$ alkylene)N($C_1$-$C_6$ alkyl)$_2$), —N($C_1$-$C_6$ alkyl)(($C_1$-$C_6$ alkylene)-CN), —N($C_1$-$C_6$ alkyl)((($C_1$-$C_6$ alkylene)N($C_1$-$C_6$ alkyl)$_2$), —NH($C_1$-$C_6$ alkylene)-O—($C_1$-$C_6$ alkyl),

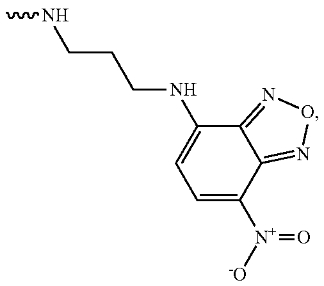
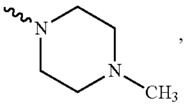,
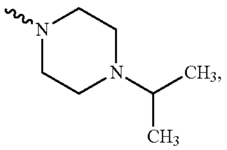
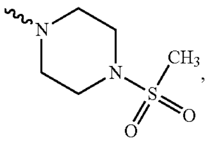,
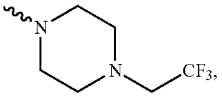
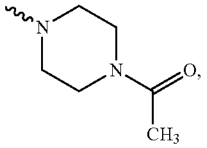
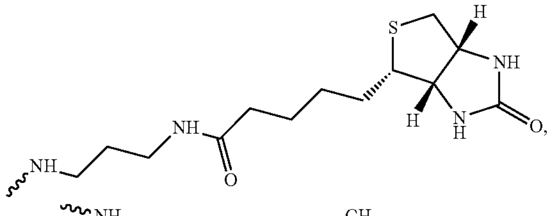
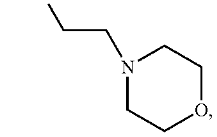
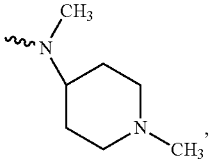,
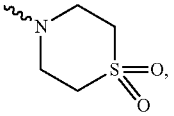
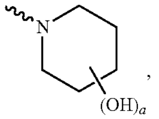,
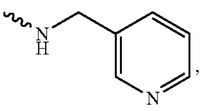,
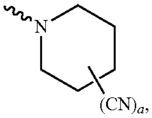
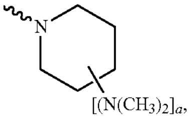

-continued

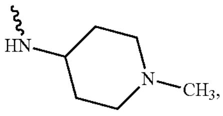, 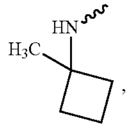, 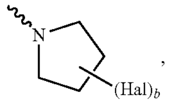, 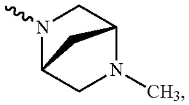, 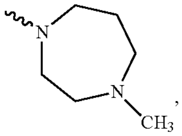, 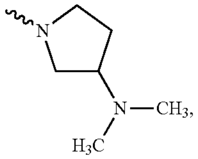, 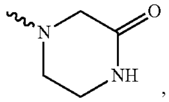, 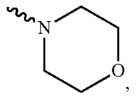, 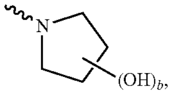 or 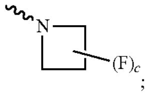;

a is an integer ranging from 0 to 10;

b is an integer ranging from 0 to 8;

c is an integer ranging from 0 to 6;

$R_5$ is

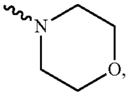, 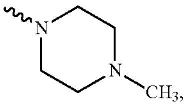, 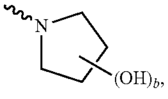 or 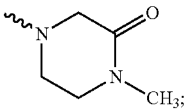;

and each $R_6$ and $R_7$ is independently —H or —I, wherein at least one of $R_6$ and $R_7$ is —I, and wherein when $R_3$ is —$C_1$-$C_3$ alkyl, then $R_7$ is —H;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of Compound 46, or a pharmaceutically acceptable salt thereof;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering, to a subject in need thereof an effective amount of a compound of Formula IV:

Formula IV

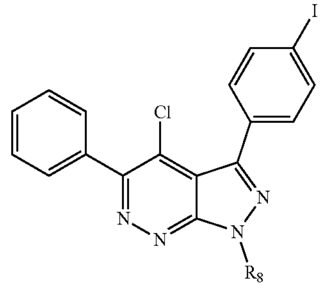

or a pharmaceutically acceptable salt thereof;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of a compound of Formula V:

Formula V

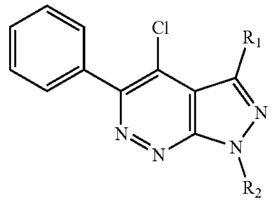

or a pharmaceutically acceptable salt thereof, wherein:

$R_1$ is:

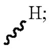; 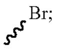; 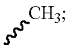; 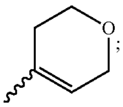; 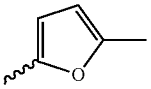; 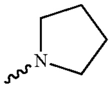; 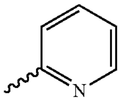; 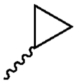; 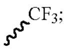; 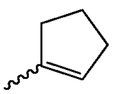; 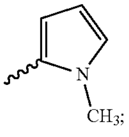; 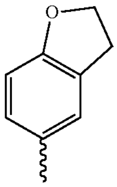; 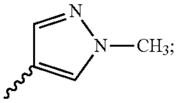; 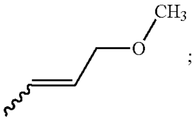; 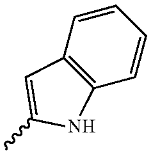; 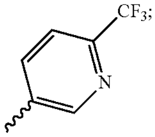; 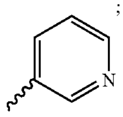; 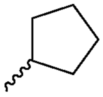

-continued

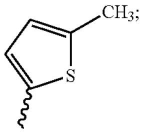
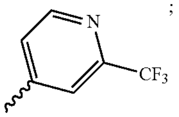
;

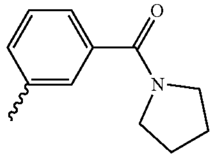
; or
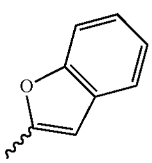
;

$R_2$ is:

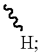
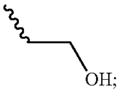
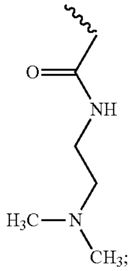

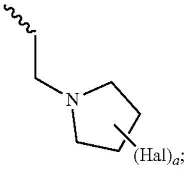
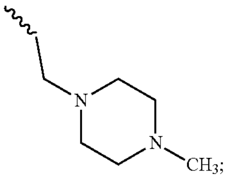

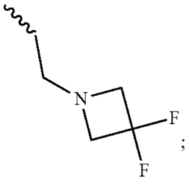
;
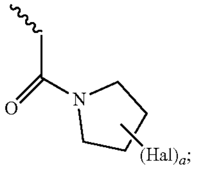
or

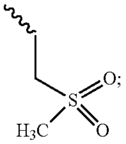

Hal is —Cl, —F, —I, or —Br; and a is 0, 1, or 2;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of a compound of Formula VI:

Formula VI

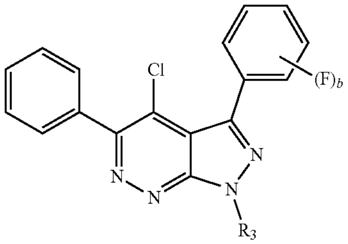

or a pharmaceutically acceptable salt thereof, wherein:

$R_3$ is:

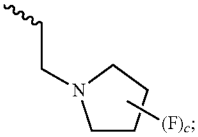
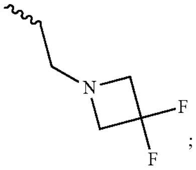

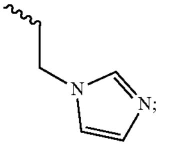
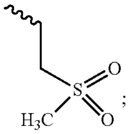
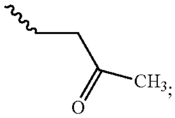

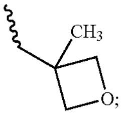
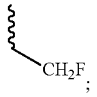
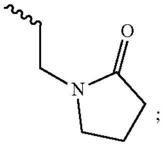
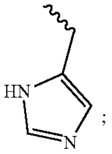

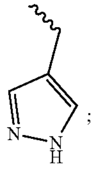
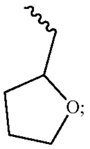
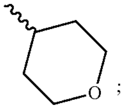
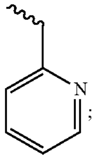

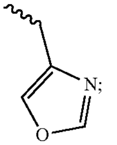
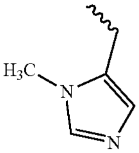
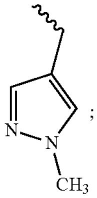
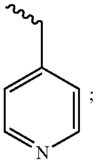

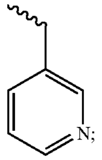
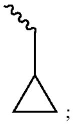
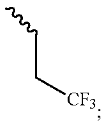
or
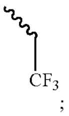

b is 0 or 1; and c is 1 or wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of a compound of Formula VII:

Formula VII

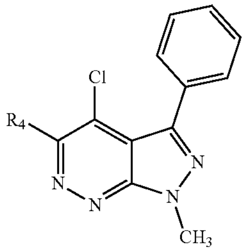

or a pharmaceutically acceptable salt thereof, wherein:

$R_4$ is —I;

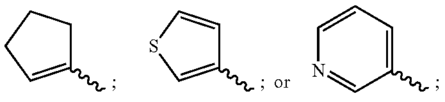

and wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of a compound of Formula XIII:

Formula XIII

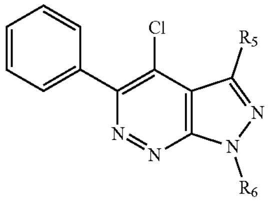

or a pharmaceutically acceptable salt thereof, wherein $R_5$ is:

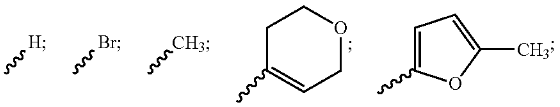

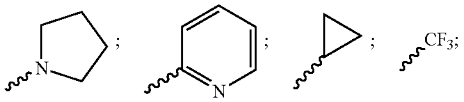

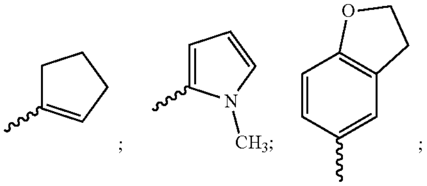

-continued

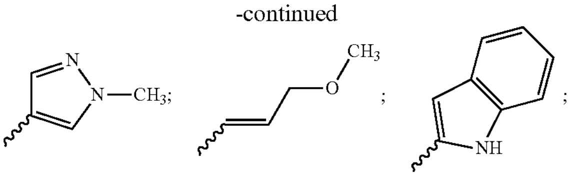

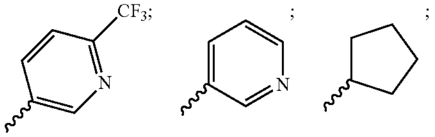

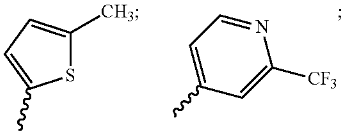

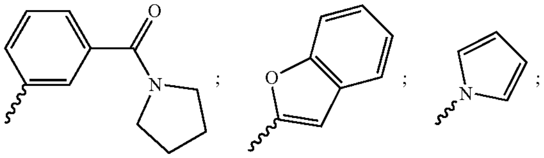

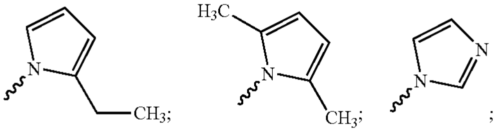

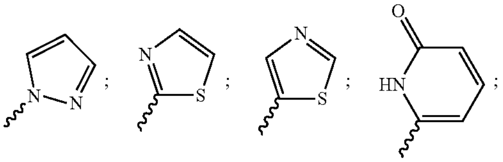

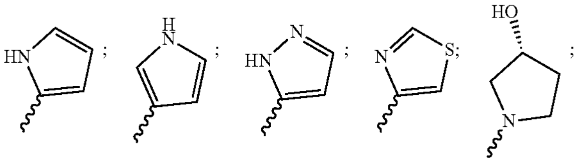

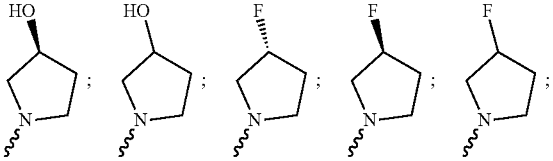

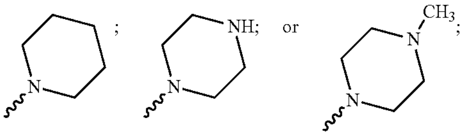

$R_6$ is:

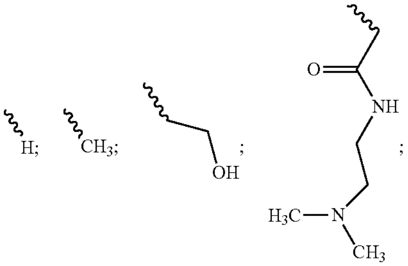

-continued

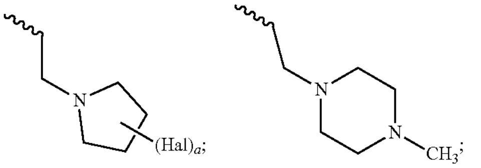

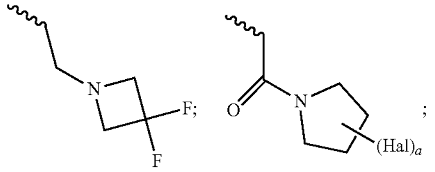

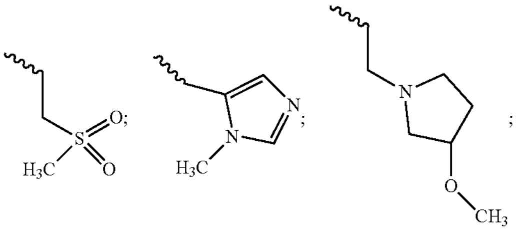

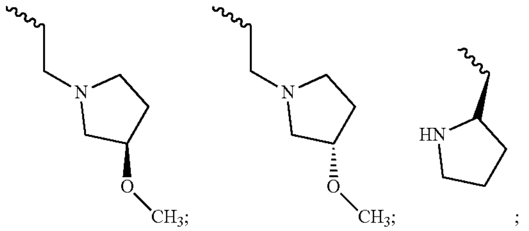

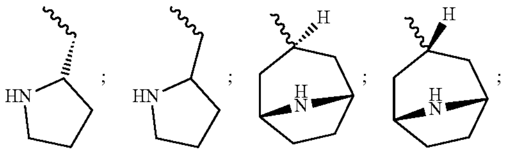

or

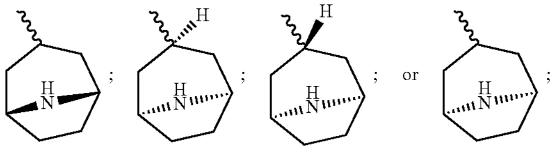

Hal is —Cl, —F, —I, or —Br, and a is 0, 1, or 2;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of a compound of Formula XIV:

Formula XIV

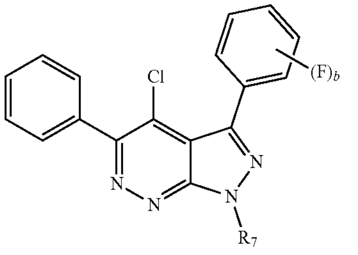

or a pharmaceutically acceptable salt thereof, wherein:

$R_7$ is:

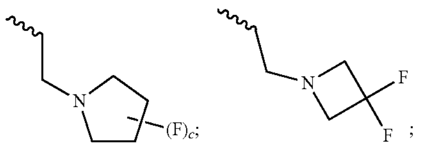

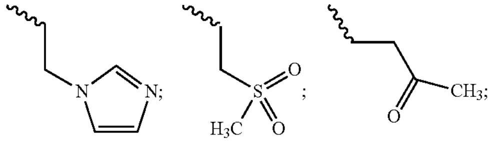

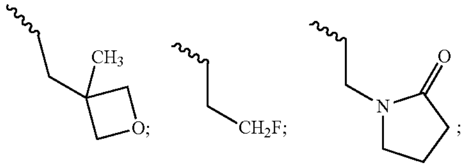

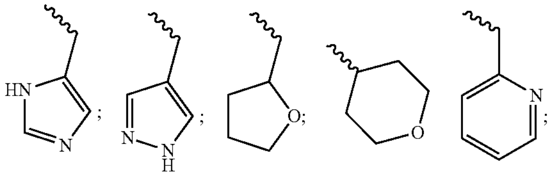

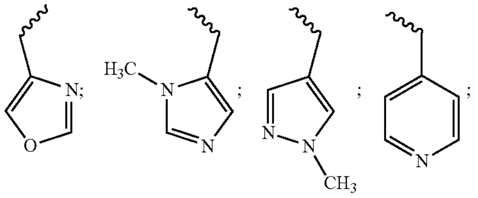

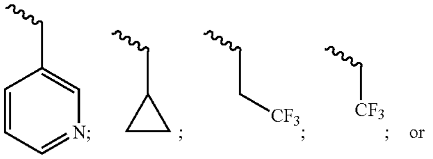

or

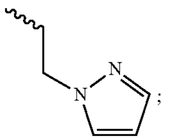

b is 0 or 1; and c is 1 or 2;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of a compound of Formula XV:

Formula XV

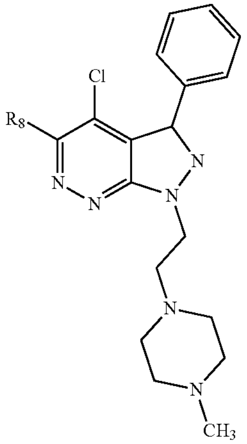

or a pharmaceutically acceptable salt thereof, wherein:

$R_8$ is:

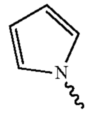 ; 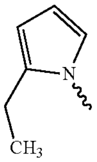 ; 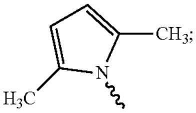 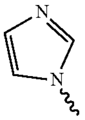 ;

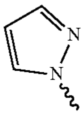 ;

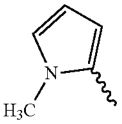 ; 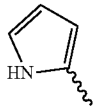 ; 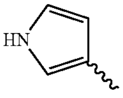 ; 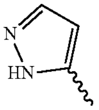 ;

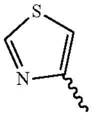 ; 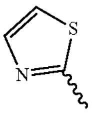 ; 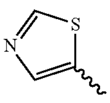 ; or

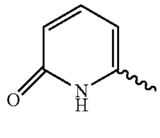 ;

and wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of any of Compounds 44, 112, 113, and 116-123, or a pharmaceutically acceptable salt thereof;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating cancer, preventing cancer, or reducing risk of developing cancer, comprising administering to a subject in need thereof an effective amount of Compound 114 or 115, or a pharmaceutically acceptable salt thereof;

wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

The invention provides methods for treating or preventing an inflammatory disease or an autoimmune disease, or reducing risk of developing an inflammatory disease or an autoimmune disease, comprising administering to a subject in need thereof an effective amount of a compound of Formula II:

Formula II

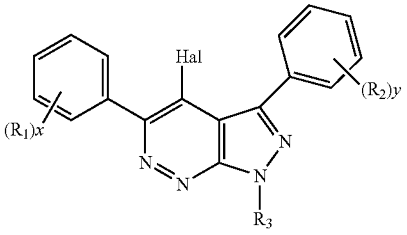

or a pharmaceutically acceptable salt thereof, wherein

Hal is —Cl, —F, —I, or —Br;

x is an integer ranging from 0 to 5;

each $R_1$ is independently —Cl, —F, —I, —Br, —$C_1$-$C_3$ alkyl, —O—$C_1$-$C_3$ alkyl, —CN, —$CF_3$, —C(O)NH($CH_3$), or —C≡$CCH_2OH$;

y is an integer ranging from 0 to 5;

each $R_2$ is independently —Cl, —F, —Br, —$C_1$-$C_3$alkyl, —O—$C_1$-$C_3$ alkyl, —CN, —$CF_3$, —C(O)NH($CH_3$), or —C≡$CCH_2OH$;

$R_3$ is —H, —$C_1$-$C_6$ alkyl, —($C_1$-$C_6$ alkylene)-OH, —($C_1$-$C_6$ alkylene)-phenyl, —($C_1$-$C_6$ alkylene)-O—($C_1$-$C_6$ alkyl), —$C_2$-$C_6$ alkenyl, —($C_1$-$C_6$ alkylene)-C(O)$R_4$, —($C_1$-$C_6$ alkylene)-$R_5$,

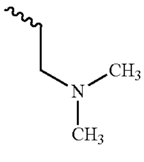 , 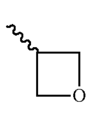 , or 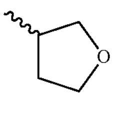 ;

$R_4$ is —OH, —O—($C_1$-$C_6$ alkyl), —$NH_2$, —NH($C_1$-$C_6$ alkyl), —NH(($C_1$-$C_6$ alkylene)-OH), —NH((—($C_1$-$C_6$ alkylene)N($C_1$-$C_6$ alkyl)$_2$), —N((—($C_1$-$C_6$ alkyl)(($C_1$-$C_6$ alkylene)-CN), —N(—($C_1$-$C_6$ alkyl)((—($C_1$-$C_6$ alkylene)N($C_1$-$C_6$ alkyl)$_2$), —NH(—($C_1$-$C_6$ alkylene)-O—($C_1$-$C_6$alkyl),

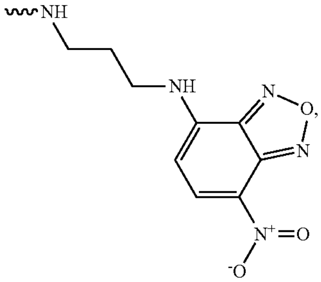

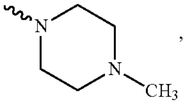

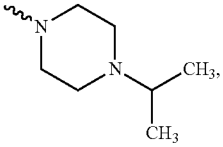

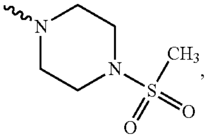

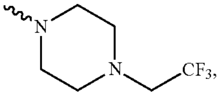

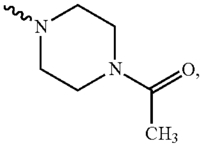

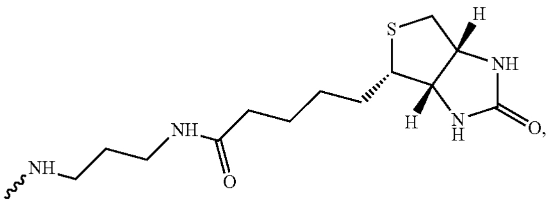

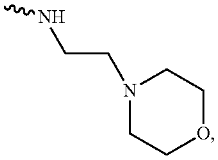

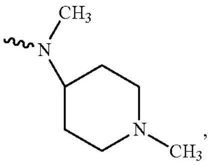

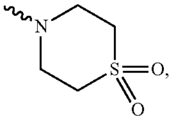

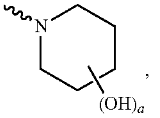

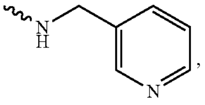

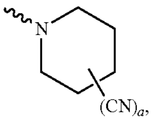

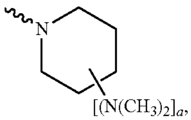

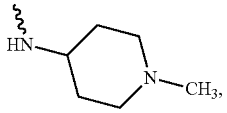

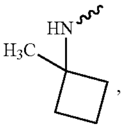

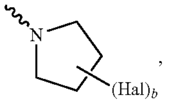

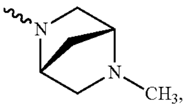

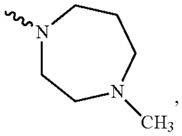

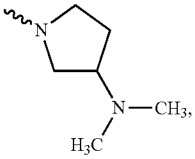

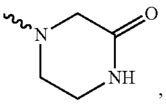

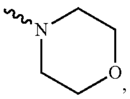

-continued

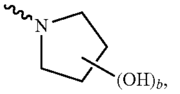

or

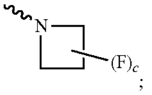

;

a is an integer ranging from 0 to 10;

b is an integer ranging from 0 to 8;

c is an integer ranging from 0 to 6; and $R_5$ is

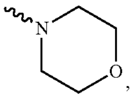

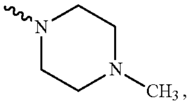

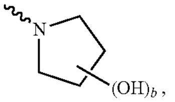

or

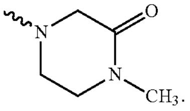

The invention provides methods for treating or preventing an inflammatory disease or an autoimmune disease, or reducing risk of developing an inflammatory disease or an autoimmune disease, comprising administering to a subject in need thereof an effective amount of a compound of Formula III:

Formula III

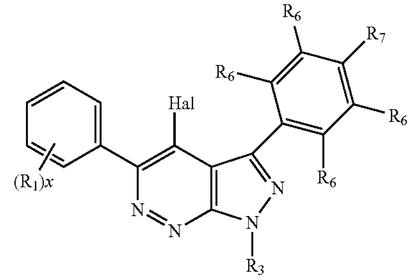

or a pharmaceutically acceptable salt thereof, wherein:

Hal is —Cl, —F, —I, or —Br;

x is an integer ranging from 0 to 5;

each $R_1$ is independently —Cl, —F, —I, —Br, —$C_1$-$C_3$ alkyl, —O—$C_1$-$C_3$ alkyl, —CN, —$CF_3$, —C(O)NH($CH_3$), or —C≡$CCH_2OH$;

$R_3$ is —H, —$C_1$-$C_6$ alkyl, —($C_1$-$C_6$ alkylene)-OH, —($C_1$-$C_6$ alkylene)-phenyl, —($C_1$-$C_6$ alkylene)-O—($C_1$-$C_6$ alkyl), —$C_2$-$C_6$ alkenyl, —($C_1$-$C_6$ alkylene)-C(O)$R_4$, —($C_1$-$C_6$ alkylene)-$R_5$,

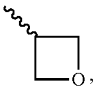

or

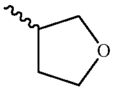

;

$R_4$ is —OH, —O—($C_1$-$C_6$ alkyl), —$NH_2$, —NH($C_1$-$C_6$ alkyl), —NH(($C_1$-$C_6$ alkylene)-OH), —NH(($C_1$-$C_6$ alkylene)N($C_1$-$C_6$ alkyl$)_2$), —N($C_1$-$C_6$ alkyl)(($C_1$-$C_6$ alkylene)-CN), —N($C_1$-$C_6$ alkyl)(($C_1$-$C_6$ alkylene)N($C_1$-$C_6$ alkyl$)_2$), —NH($C_1$-$C_6$ alkylene)-O—($C_1$-$C_6$ alkyl),

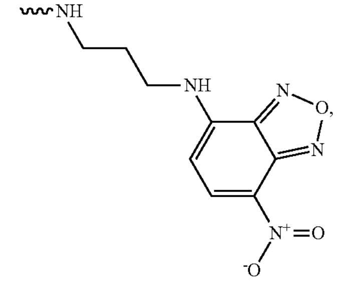 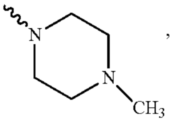 ,

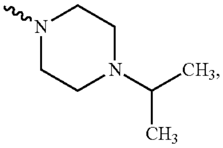 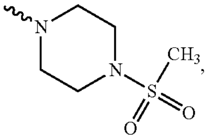

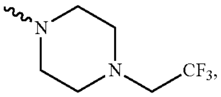 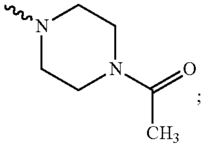 ;

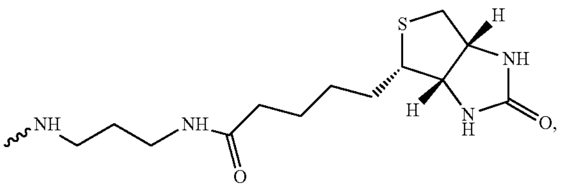

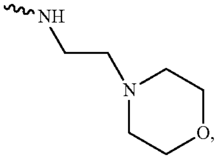 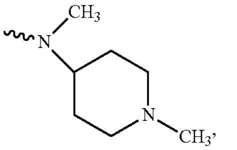

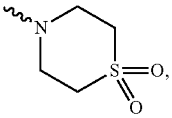 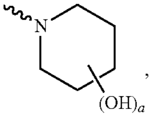 , 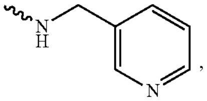 ,

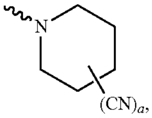 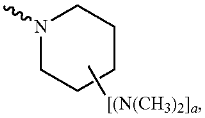

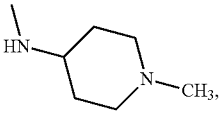 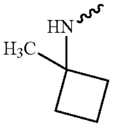 , 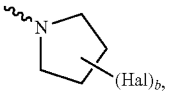

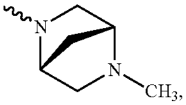 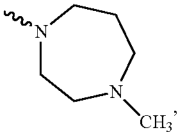

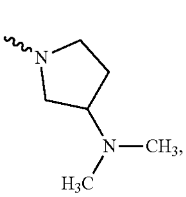 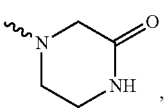 , 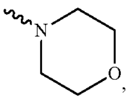

-continued

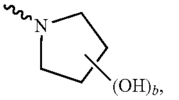 or 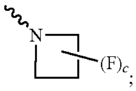 ;

a is an integer ranging from 0 to 10;
b is an integer ranging from 0 to 8;
c is an integer ranging from 0 to 6;
$R_5$ is

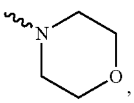 , 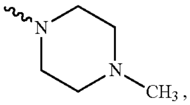 , 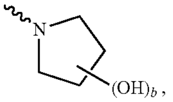 , or 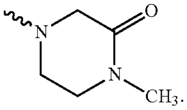

and each $R_6$ and $R_7$ is independently —H or —I, wherein at least one of $R_6$ and $R_7$ is —I, and wherein when $R_3$ is —$C_1$-$C_3$ alkyl, then $R_7$ is —H.

The invention provides methods for treating or preventing an inflammatory disease or an autoimmune disease, or reducing risk of developing an inflammatory or an autoimmune disease, comprising administering to a subject in need thereof an effective amount of Compound 46, or a pharmaceutically acceptable salt thereof.

The invention provides methods for treating or preventing an inflammatory or an autoimmune disease, or reducing risk of developing an inflammatory or an autoimmune disease, comprising administering to a subject in need thereof an effective amount of a compound of Formula IV:

Formula IV

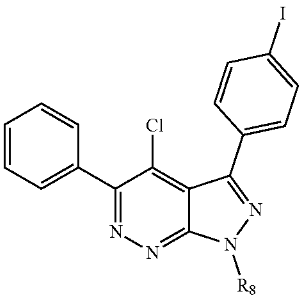

or a pharmaceutically acceptable salt thereof.

The invention provides methods for treating or preventing an inflammatory or an autoimmune disease, or reducing risk of developing an inflammatory or an autoimmune disease, comprising administering to a subject in need thereof an effective amount of a compound of Formula V:

Formula V

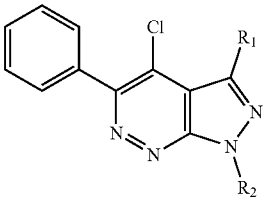

or a pharmaceutically acceptable salt thereof, wherein:

$R_1$ is:

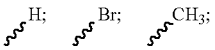 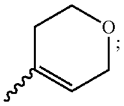 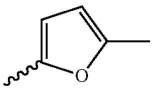 ;

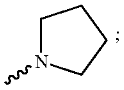 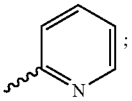 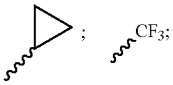

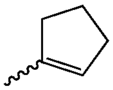 ; 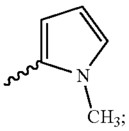 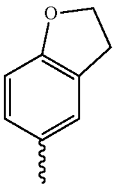 ;

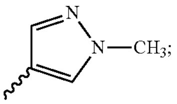 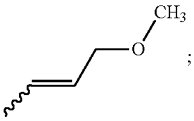 ; 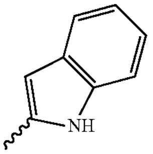 ;

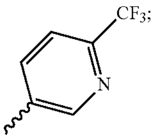 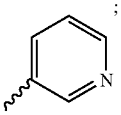 ; 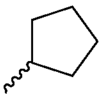 ;

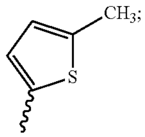 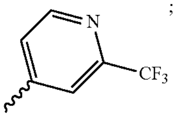 ;

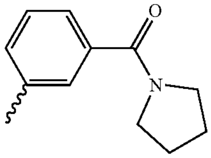 ; or 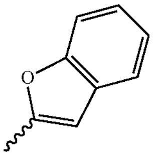 ;

$R_2$ is:

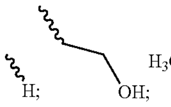 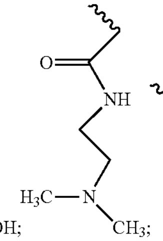 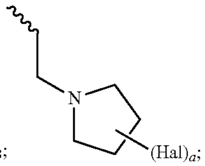

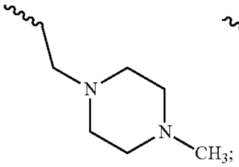 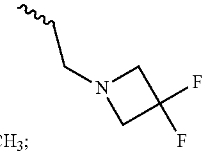 ;

-continued

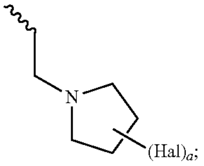 or 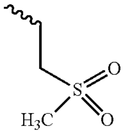 ;

Hal is —Cl, —F, —I, or —Br; and a is 0, 1, or 2.

The invention provides methods for treating or preventing an inflammatory or an autoimmune disease, or reducing risk of developing an inflammatory or an autoimmune disease, comprising administering to a subject in need thereof an effective amount of a compound of Formula VI:

Formula VI

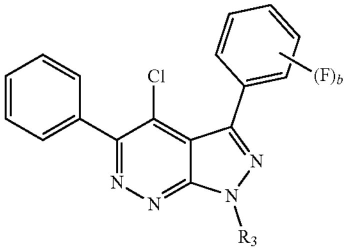

or a pharmaceutically acceptable salt thereof, wherein:

$R_3$ is:

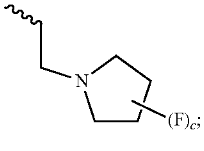 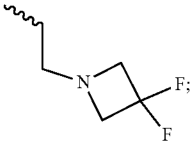

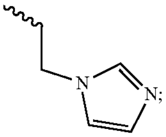 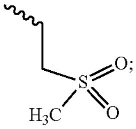 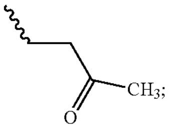

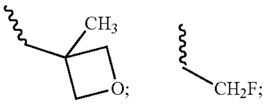 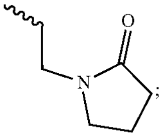

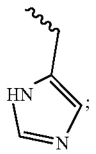 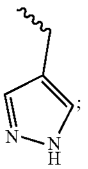 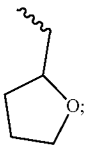

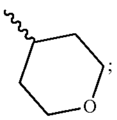 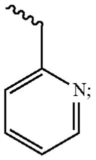 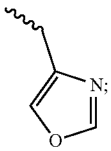

-continued

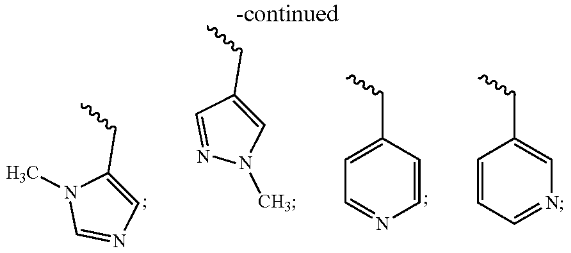

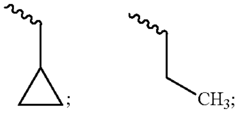

or

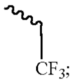

b is 0 or 1, and c is 1 or 2.

The invention provides methods for treating or preventing an inflammatory or an autoimmune disease, or reducing risk of developing an inflammatory or an autoimmune disease, comprising administering to a subject in need thereof an effective amount of a compound of Formula VII:

Formula VII

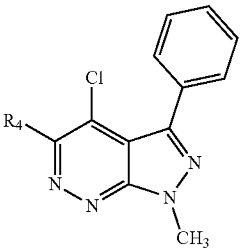

or a pharmaceutically acceptable salt thereof, wherein:

$R_4$ is —I;

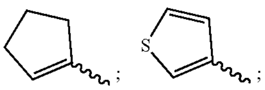

or

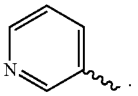

The invention provides methods for treating or preventing an inflammatory disease or an autoimmune disease, or reducing risk of developing an inflammatory disease or an autoimmune disease, comprising administering to a subject in need thereof an effective amount of a compound of Formula XIII:

Formula XIII

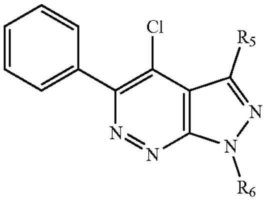

or a pharmaceutically acceptable salt thereof, wherein $R_5$ is:

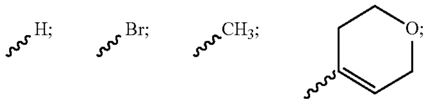

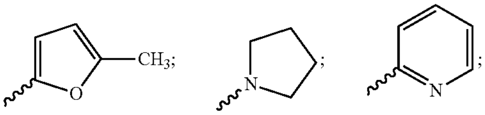

-continued

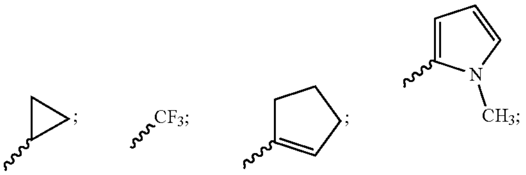

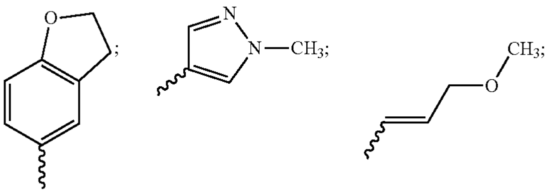

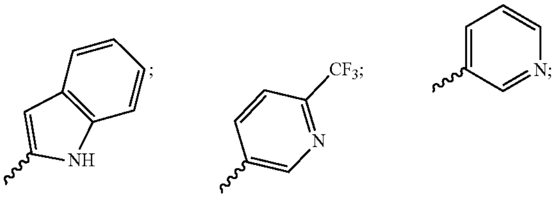

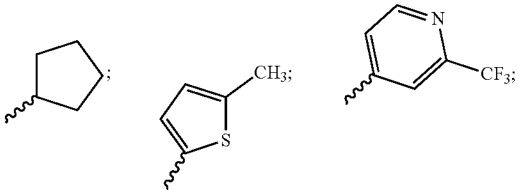

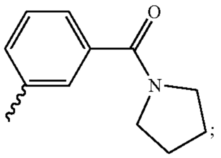

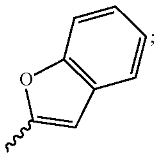

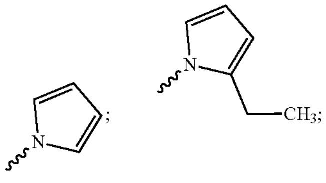

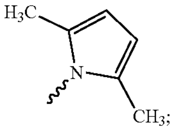

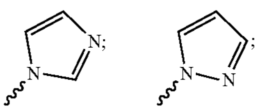

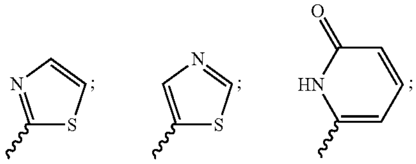

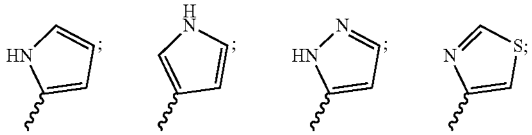

-continued

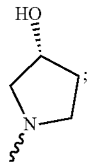 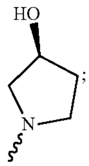 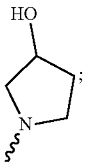 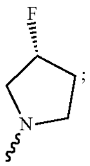

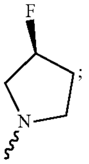 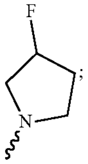 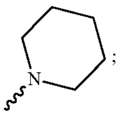 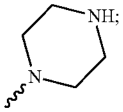

or

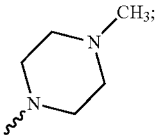

$R_6$ is:

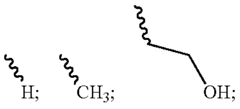 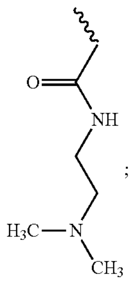

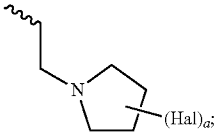 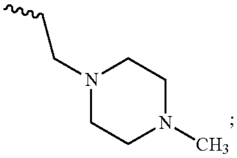

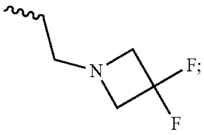 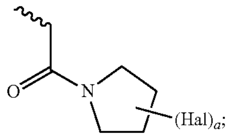

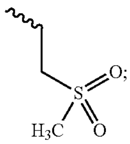 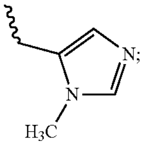 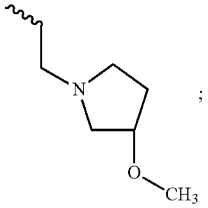

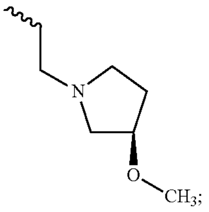 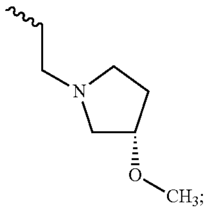 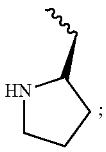

-continued

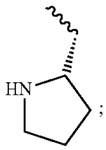 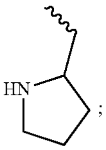 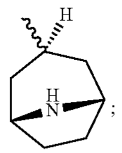 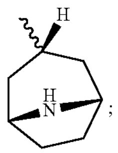

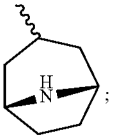 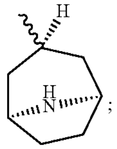 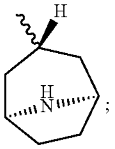 or 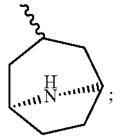

Hal is —Cl, —F, —I, or —Br; and a is 0, 1, or 2.

The invention provides methods for treating or preventing an inflammatory disease or an autoimmune disease, or reducing risk of developing an inflammatory disease or an autoimmune disease, comprising administering to a subject in need thereof an effective amount of a compound of Formula XIV:

Formula XIV

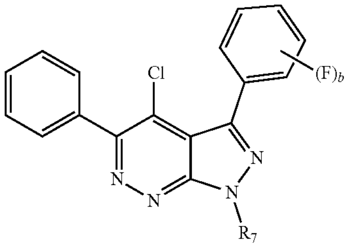

or a pharmaceutically acceptable salt thereof, wherein:

$R_7$ is:

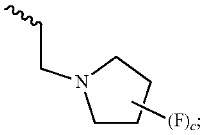 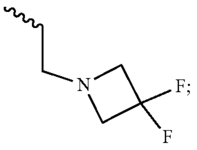

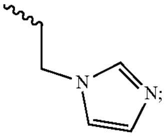 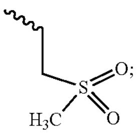 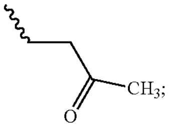

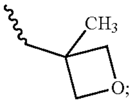 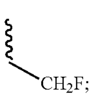 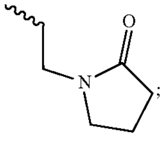

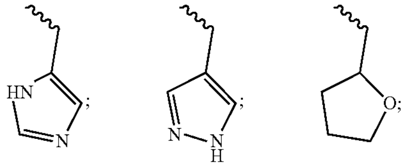

-continued

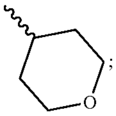
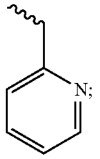
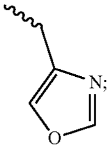
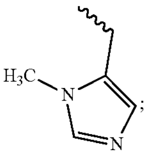
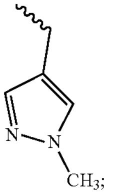
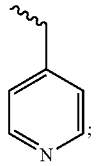
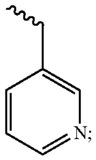
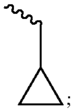
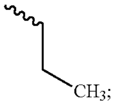
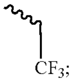
or
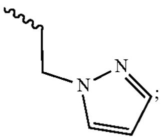

b is 0 or 1; and c is 1 or 2.

The invention provides methods for treating or preventing an inflammatory disease or an autoimmune disease, or reducing risk of developing an inflammatory disease or an autoimmune disease, comprising administering to a subject in need thereof an effective amount of a compound of Formula XV:

Formula XV

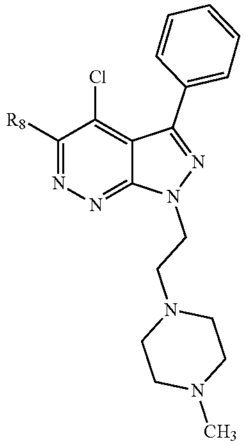

or a pharmaceutically acceptable salt thereof, wherein:

$R_8$ is:

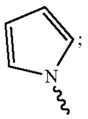
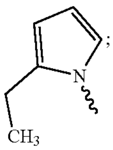
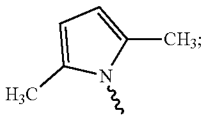

-continued

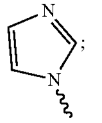
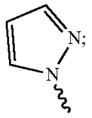
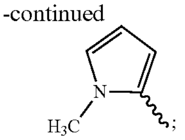
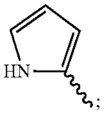
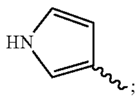
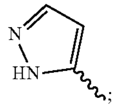
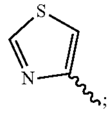
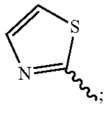
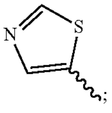
or
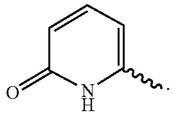

The invention provides methods for treating or preventing an inflammatory disease or an autoimmune disease, or reducing risk of developing an inflammatory or an autoimmune disease, comprising administering to a subject in need thereof an effective amount of any of Compounds 44, 112, 113, and 116-123, or a pharmaceutically acceptable salt thereof.

The invention provides methods for treating or preventing an inflammatory disease or an autoimmune disease, or reducing risk of developing an inflammatory disease or an autoimmune disease, comprising administering to a subject in need thereof an effective amount of Compound 114 or Compound 115, or a pharmaceutically acceptable salt thereof.

DETAILED DESCRIPTION OF THE INVENTION

In one embodiment, the invention provides methods for treating or preventing cancer, or reducing risk of developing cancer, comprising administering to a subject in need thereof an effective amount of a compound of the invention. In some embodiments, the compound of the invention is Compound 85 or a pharmaceutically acceptable salt thereof.

In one embodiment, the invention provides methods for treating or preventing an inflammatory disease or an autoimmune disease, or reducing risk of developing an inflammatory disease or an autoimmune disease, comprising administering to a subject in need thereof an effective amount of a compound of the invention. In some embodiments, the compound of the invention is Compound 85 or a pharmaceutically acceptable salt thereof.

Definitions

The term "alkyl" refers to a straight or branched saturated hydrocarbon group. Illustrative alkyl groups include $—CH_3$, $—CH_2CH_3$, $—CH_2CH_2CH_3—CH(CH_3)_2$, $—CH_2CH_2CH_2CH_3$, $—CH(CH_3)CH_2CH_3$, $—CH_2CH(CH_3)_2$, $—C(CH_3)_3$, $—CH_2CH_2CH_2CH_2CH_3$, $—CH(CH_3)CH_2CH_2CH_3$, $—CH_2CH_2CH(CH_3)_2$, $—CH_2C(CF_{13})_3$, $—CH_2CH_2CH_2CH_2CH_3$, $—CH(CH_3)CH_2CH_2CH_3$, $—CH_2CH_2CH(CH_3)_2$ and $—CH(CH_3)C(CH_3)_3$ groups.

The term "alkylene" refers to an alkyl group bonded to another atom or group. Illustrative alkylene groups include $—CH_2—$, $—CH_2CH_2—$, $—CH_2CH_2CH_2—$, $—C(CH_3)_2—$, $—CH(CH_3)$, $—CH_2CH_2CH_2CH_2—$, $—CH(CH_3)CH_2CH_2—$, $—CH_2C(CH_3)_2—$, $—C(CH_3)_2CH_2—$, $—CH_2CH_2CH_2CH_2CH_2—$, $—CH(CH_3)CH_2CH_2CH_2—$, $—CH_2CH_2C(CH_3)_2—$, $—CH_2CH(CH_3)CH_2CH_2$, $—CH_2CH_2CH(CH_3)CH_2—$, $—CH_2CH_2CH_2CH_2CH_2CH_2—$, $—CH(CH_3)CH_2CH_2CH_2CH_2—$, $—CH_2CH_2CH_2C(CH_3)_2—$, $—CH_2CH(CH_3)CH_2CH_2CH_2—$, $—CH_2CH_2CH_2CH(CH_3)CH_2—$ and $—C(CH_3)_2C(CH_3)_2—$ groups.

The term "alkenyl" refers to a straight or branched hydrocarbon group having one or more double bonds. Illustrative alkenyl groups include $—CH=CH_2$, $—CH_2CH=CH_2$, cis $—CH=CHCH_3$, trans $—CH=CHCH_3$, $—C(CH_3)=CH_2$, cis $—CH=CHCH_2CH_3$, trans $—CH=CHCH_2CH_3$, cis $—CH_2CH=CHCH_3$, trans $—CH_2CH=CHCH_3$, $—CH_2CH_2CH—CH_2$, cis $—CH—CHCH_2CH_2CH_3$, trans $—CH=CHCH_2CH_2CH_3$, cis $—CH_2CH_2CH=CHCH_3$, trans $—CH_2CH_2CH=CHCH_3$, $—CH_2CH_2CH_2CH=CH_2$, $—CH_2CH=C(CH_3)_2$, cis $—CH=CHCH_2CH_2CH_2CCH_3$, trans $—CH=CHCH_2CH_2CH_2CH_3$, cis $—CH_2CH_2CH_2CH=CHCH_3$, trans $—CH_2CH_2CH_2CH=CHCH_3$, $—CH_2CH_2CH_2CH_2CH=CH_2$, and $—CH_2CH_2CH=C(CH_3)_2$, groups.

The word "about" when immediately preceding a numerical value means a range of plus or minus 10% of that value, e.g., "about 100 mg" means 90 rig to 110 mg, "about 300 mg" means 270 mg to 330 mg, etc.

Abbreviations

DCM dichloromethane
DEAD diethyl azodicarboxylate
DIPEA diisopropylethylamine
DMF dimethylformamide
DMSO Dimethyl sulfoxide
ESI Electrospray ionization
ESI-TOF Electrospray ionization-Time-of-flight
HATU 2-(7-Aza-1H-benzotriazole-1-yl)-1,1,3,3-tetramethyluronium hexafluorophosphate
HPLC High-performance liquid chromatography
LCMS Liquid Chromatography-mass spectrometry
LDA lithium diisopropyl amide
m/z Mass-to-charge ratio
MS Mass spectrometry
Rt Retention time
TFA trifluoroacetic acid
THF tetrahydrofuran The term "effective amount" means an amount of a compound of the invention that is effective to treat or prevent cancer, an inflammatory disease or an autoimmune disease, or to lower risk of developing cancer, an inflammatory disease or an autoimmune disease. In some embodiments, where another therapeutic or prophylactic agent is administered prior to, subsequent to or concurrently with administration of a compound of the invention, the "effective amount" is the total amount of (i) the compound of the invention and (ii) the other therapeutic or prophylactic agent that is effective to treat or prevent cancer, an inflammatory disease or an autoimmune disease, or to lower risk developing of cancer, an inflammatory disease or an autoimmune disease.

A "subject" is a mammal, including a species-rich order, e.g., a primate, such as a human; a Rodentia species, such as a mouse, a rat or a guinea pig; a Carnivora species such as a *Canis* sp., e.g., a dog, *Felis* sp., e.g., a cat, weasel, bear or seal; a non-human primate, such as a monkey, chimpanzee, baboon or rhesus; a *Chiroptera* species, such as a bat; a *Soricomorpha* species, such as a shrew, mole or solenodon; and a *Cetartiodactyla* species, such as a whale. In one embodiment, the subject is a human. In another embodiment, the human is a human fetus.

Compounds of the Invention

Compounds of Formula I

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula I:

Formula I

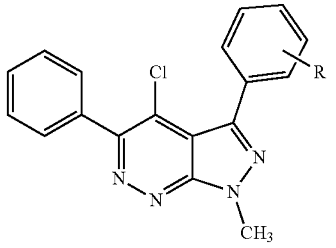

or a pharmaceutically acceptable salt thereof, wherein R is fluoro, chloro, iodo, methyl, methoxy, cyano, trifluoromethyl, or $—(CO)NH(CH_3)$.

In one embodiment, R of Formula I is in the para position relative to the pyrazolopyridazino ring system. In one embodiment. R of Formula I is in the meta position relative to the pyrazolopyridazino ring system. In one embodiment, R of Formula I is in the ortho position relative to the pyrazolopyridazino ring system.

Compounds of Formula II

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula II:

Formula II

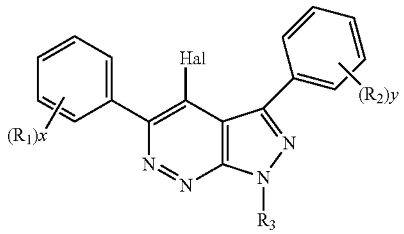

or a pharmaceutically acceptable salt thereof, wherein Hal is —Cl, —F, —I, or —Br;

x is an integer ranging from 0 to 5;

each $R_1$ is independently —Cl, —F, —I, —Br, $—C_1\text{-}C_3$alkyl, $—O—C_1\text{-}C_3$alkyl, —CN, $—CF_3$, $—C(O)NH(CH_3)$, or $—C≡CCH_2OH$;

y is an integer ranging from 0 to 5;

each $R_2$ is independently —Cl, —F, —Br, $—C_1\text{-}C_3$ alkyl, $—O—C_1\text{-}C_3$ alkyl, —CN, $CF_3$, $—C(O)NH(CH_3)$, or $—C≡CCH_2OH$;

$R_3$ is —H, $—C_1\text{-}C_6$ alkyl, $—(C_1\text{-}C_6$ alkylene)-OH, $—(C_1\text{-}C_6$alkylene)-phenyl, $—(C_1\text{-}C_6$alkylene)-O—$(C_1\text{-}C_6$ alkyl), $—C_2\text{-}C_6$ alkenyl, $—(C_1\text{-}C_6$alkylene)-$C(O)R_4$, $—(C_1\text{-}C_6$alkylene)-$R_5$,

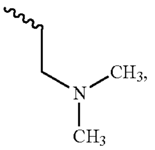, 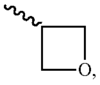, or 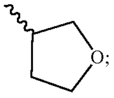;

$R_4$ is —OH, —O—($C_1$-$C_6$alkyl), —$NH_2$, —NH($C_1$-$C_6$ alkyl), —NH(($C_1$-$C_6$ alkylene)-OH), —NH(($C_1$-$C_6$alkylene)N($C_1$-$C_6$ alkyl)$_2$), —N($C_1$-$C_6$ alkyl)(($C_1$-$C_6$ alkylene)-CN), —N($C_1$-$C_6$ alkyl)(($C_1$-$C_6$ alkylene) N($C_1$-$C_6$ alkyl)$_2$), —NH($C_1$-$C_6$ alkylene)-O—($C_1$-$C_6$ alkyl),

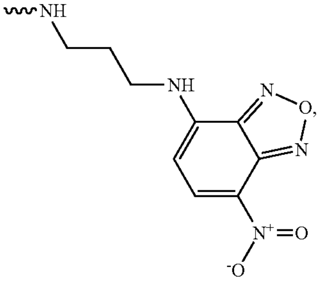, 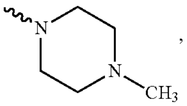,

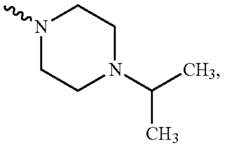, 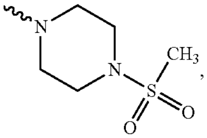,

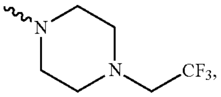, 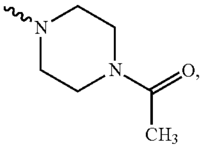,

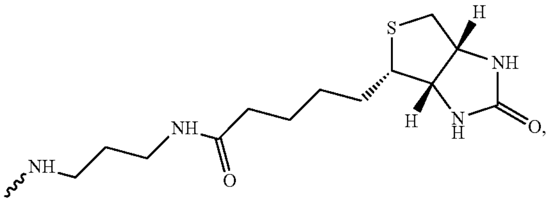,

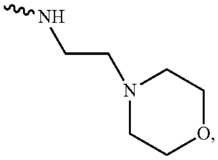, 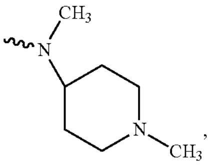,

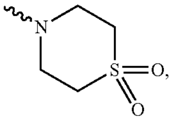, 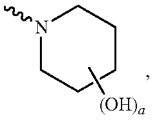, 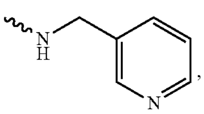,

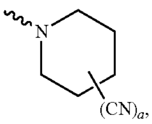, 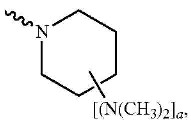,

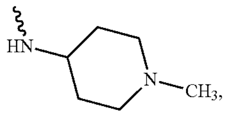, 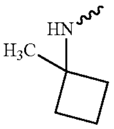, 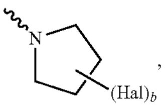,

-continued

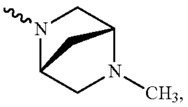, 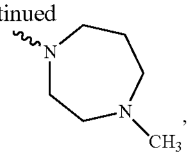,

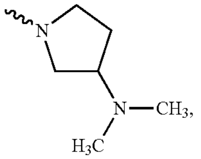, 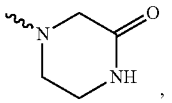, 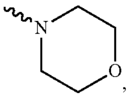,

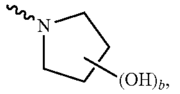 or 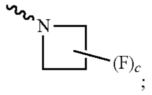;

a is an integer ranging from 0 to 10;
b is an integer ranging from 0 to 8;
c is an integer ranging from 0 to 6; and
$R_5$ is

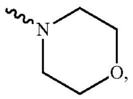, 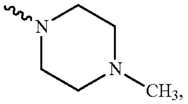, 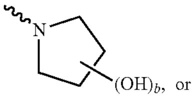 or

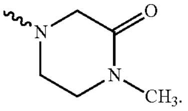.

In certain embodiments, Hal is —Cl. In yet another embodiment, x and y are 0.

In certain embodiments, x and y are 0, x is 0 and is 1, x is 1 and y is 2, x is 1 and y is 0, x is 1 and v is 1, x is 1 and y is 2, x is 2 and y is 0, x is 2 and y is 1, or x is 2 and y is 2.

In certain embodiments, Hal is —Cl and: x and y are 0, x is 0 and y is 1, x is 1 and y is 2, x is 1 and y is 0, x is 1 and Y is 1, x is 1 and Y is 2, x is 2 and y is 0, x is 2 and y is 1, or x is 2 and y is 2.

In particular embodiments, x is 1 and $R_1$ is in the ortho position relative to the pyrazolopyridazino ring system. In certain embodiments, x is 1 and $R_1$ is in the para position relative to the pyrazolopyridazino ring system. In further embodiments, x is 1 and $R_1$ is in the meta position relative to the pyrazolopyridazino ring system.

In particular embodiments, y is 1 and $R_2$ is in the ortho position relative to the pyrazolopyridazino ring system. In certain embodiments, y is 1 and $R_2$ is in the para position relative to the pyrazolopyridazino ring system. In further embodiments, y is 1 and $R_2$ is in the meta position relative to the pyrazolopyridazino ring system.

In particular embodiments, x is 2 and $R_1$ is in the ortho and meta position relative to the pyrazolopyridazino ring system. In certain embodiments, x is 2 and $R_1$ is in the ortho and para position relative to the pyrazolopyridazino ring system. In further embodiments, x is 2 and $R_1$ is in the para and meta position relative to the pyrazolopyridazino ring system.

In particular embodiments, y is 2 and $R_2$ is in the ortho and meta position relative to the pyrazolopyridazino ring system. In certain embodiments, y is 2 and $R_2$ is in the ortho and para position relative to the pyrazolopyridazino ring system. In further embodiments, y is 2 and $R_2$ is in the para and meta position relative to the pyrazolopyridazino ring system.

In yet other embodiments, $R_1$ is chloro. In certain embodiments, $R_1$ is fluoro. In certain embodiments, $R_1$ is iodo. In other embodiments, $R_1$ is —Br. In further embodiments, R is —$OCH_3$. In other embodiments, $R_1$ is —$CH_3$. In yet other embodiments. $R_1$ is —C(O)N(H)$CH_3$. In certain embodiments, R is —$CF_3$. In further embodiments, $R_1$ is —CN. In additional embodiments, $R_1$ is —C≡C$CH_2$OH.

In yet other embodiments, x is 1 or 2, and $R_1$ is —Cl, —F, —Br, —$OCH_3$, —$CH_3$, —C(O)N(H)$CH_3$, —$CF_3$, —CN or —C≡C$CH_2$OH.

In yet other embodiments, Hal is —Cl, x is 1 or 2, and $R_1$ is —F, —Br, —$OCH_3$, —$CH_3$, —C(O)N(H)$CH_3$, —$CF_3$, —CN or —C≡C$CH_2$OH.

In yet other embodiments, $R_2$ is —Cl. In certain embodiments, $R_2$ is —F. In other embodiments, $R_2$ is —Br. In further embodiments, $R_2$ is —$OCH_3$. In other embodiments, $R_2$ is —$CH_3$. In yet other embodiments, $R_2$ is —C(O)N(H) $CH_3$. In certain embodiments, $R_2$ is —$CF_3$. In further embodiments, $R_2$ is —CN. In additional embodiments, $R_2$ is —C≡C$CH_2$OH.

In yet other embodiments, y is 1 or 2, and $R_2$ is —Cl, —F, —Br, —$OCH_3$, —$CH_3$, —C(O)N(H)$CH_3$, —$CF_3$, —CN or —C≡C$CH_2$OH.

In yet other embodiments, Hal is —Cl, y is 1 or 2, and $R_2$ is —Cl, —F, —Br, —$OCH_3$, —$CH_3$, —C(O)N(H)$CH_3$, —$CF_3$, —CN or —C≡C$CH_2$OH.

In particular embodiments. $R_3$ is —H. In certain embodiments, $R_3$ is —$CH_3$. In further embodiments, $R_3$ is —$CH_2CH_3$. In still further embodiments, $R_3$ is —$CHCH_2$. In other embodiments, $R_3$ is —$CH_2CH_2$OH. In particular embodiments. $R_3$ is —$(CH_2)_2C_6H_5$. In other embodiments, $R_3$ is —$CH_2$C(O)OH. In yet other embodiments, $R_3$ is —$CH_2$C(O)N(H)$CH_3$. In certain embodiments, $R_3$ is —$CH_2$C(O)N(H)($(CH_2)_2$N$(CH_3)_2$).

In yet other embodiments, $R_3$ is —$CH_2$C(O)N(H)($(CH_2)_3$ N$(CH_3)_2$). In other embodiments, $R_3$ is —$CH_2$C(O)N($CH_3$) $CH_2$CN. In particular embodiments, $R_3$ is —$CH_2$C(O)$NH_2$. In certain embodiments, $R_3$ is —$CH_2$C(O)N(H)($(CH_2)_2$OH). In other embodiments, $R_3$ is —$CH_2$C(O)N(H)($(CH_2)_2$ $OCH_3$). In still further embodiments, $R_3$ is —$CH_2C(CH_3)_2$ OH. In yet other embodiments, $R_3$ is —$CH_2$C(O)$OCH_3$. In further embodiments, $R_3$ is —$CH_2$CH(OH)$CH_3$. In still further embodiments, $R_3$ is —$CH_2CH_2$OH. In particular embodiments, $R_3$ is —CH($CH_3$)$CH_2$OH.

In further embodiments, $R_1$ is —$CH_2$C(O)$R_4$ and $R_4$ is

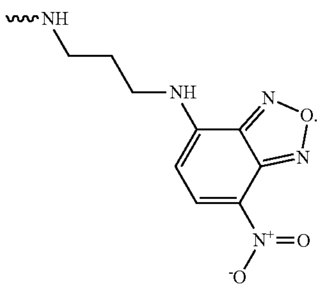

In other embodiments. $R_3$ is —$CH_2$C(O)$R_4$ and $R_4$ is

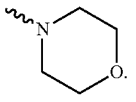

In particular embodiments, $R_3$ is —$CH_2$C(O)$R_4$ and $R_4$ is

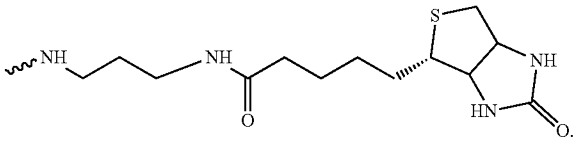

In yet other embodiments, $R_3$ is —$CH_2$C(O)$R_4$ and $R_4$ is

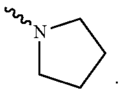

In certain embodiments, $R_3$ is —$CH_2$C(O)$R_4$ and $R_4$ is

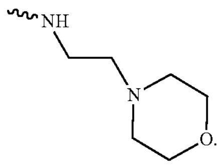

In other embodiments, $R_3$ is —$CH_2$C(O)$R_4$ and $R_4$ is

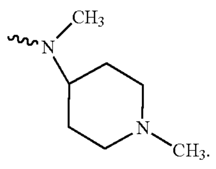

In particular embodiments, $R_3$ is —$CH_2$C(O)$R_4$ and $R_4$ is

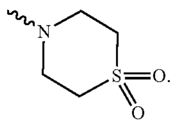

In yet other embodiments, $R_3$ is —$CH_2$C(O)$R_4$ and $R_4$ is

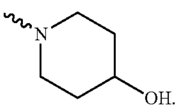

In certain embodiments, $R_3$ is $—CH_2C(O)R_4$ and $R_4$ is

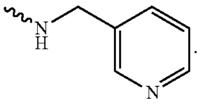

In other embodiments, $R_3$ is $—CH_2C(O)R_4$ and $R_4$ is

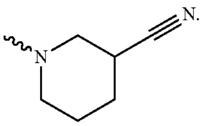

In particular embodiments, $R_3$ is $—CH_2C(O)R_4$ and $R_4$ is

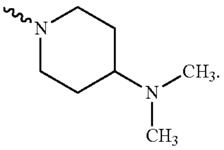

In yet other embodiments, $R_3$ is $—CH_2C(O)R_4$ and $R_4$ is

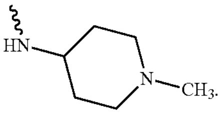

In certain embodiments, $R_3$ is $—CH_2C(O)R_4$ and $R_4$ is

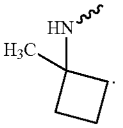

In other embodiments, $R_3$ is $—CH_2C(O)R_4$ and $R_4$ is

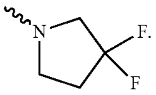

In particular embodiments, $R_3$ is $—CH_2C(O)R_4$ and $R_4$ is

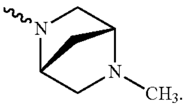

In yet other embodiments, $R_3$ is, $—CH_2C(O)R_4$ and $R_4$ is

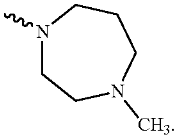

In certain embodiments, $R_3$ is $—CH_2C(O)R_4$ and $R_4$ is

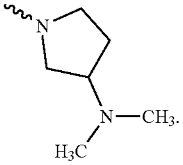

In other embodiments, $R_3$ is $—CH_2C(O)R_4$ and $R_4$ is

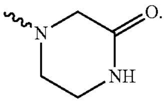

In particular embodiments, $R_3$ is $—CH_2C(O)R_4$ and $R_4$ is

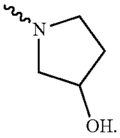

In yet other embodiments, $R_3$ is $—CH_2C(O)R_4$ and $R_4$ is

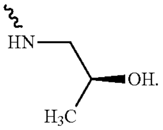

In certain embodiments, $R_3$ is $—CH_2C(O)R_4$ and $R_4$ is

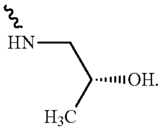

In other embodiments, $R_3$ is $—CH_2C(O)R_4$ and $R_4$ is

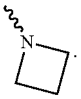

In particular embodiments, $R_3$ is —$CH_2C(O)R_4$ and $R_4$ is

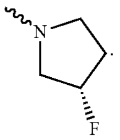

In yet other embodiments, $R_3$ is —$CH_2C(O)R_4$ and $R_4$ is

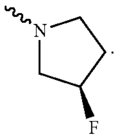

In certain embodiments, $R_3$ is —$CH_2C(O)R_4$ and $R_4$ is

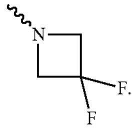

In other embodiments, $R_3$ is —$CH_2C(O)R_4$ and $R_4$ is

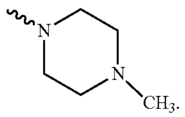

In further embodiments of the invention, $R_3$ is —$CH_2C(O)R_4$ and $R_4$ is

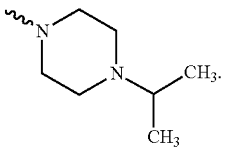

In certain embodiments of the invention, $R_3$ is —$CH_2C(O)R_4$ and $R_4$ is

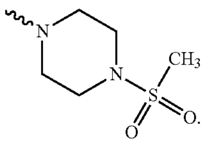

In other embodiments, $R_3$ is —$CH_2C(O)R_4$ and $R_4$ is

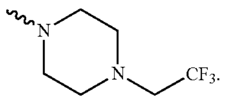

In further embodiments, $R_3$ is —$CH_2C(O)R_4$ and $R_4$ is

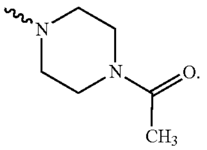

In further embodiments, $R_3$ is —$CH_2C(O)R_4$ and $R_4$ is

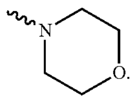

In particular embodiments, $R_3$ is —$(CH_2)_2R_5$ and $R_5$ is

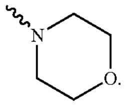

In yet other embodiments, $R_3$ is —$(CH_2)_2R_5$ and $R_5$ is

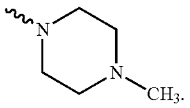

In certain embodiments, $R_3$ is —$(CH_2)_2R_5$ and $R_5$ is

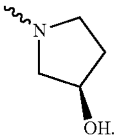

In other embodiments, invention, $R_3$ is —$(CH_2)_2R_5$ and $R_5$ is

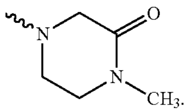

In some embodiments, a is an integer ranging from 0 to 5. In some embodiments, b is an integer ranging from 0 to 4. In some embodiments, c is an integer ranging from 0 to 6.

Illustrative Compounds of Formula II
In certain embodiments the compound of Formula II has the structure:
1
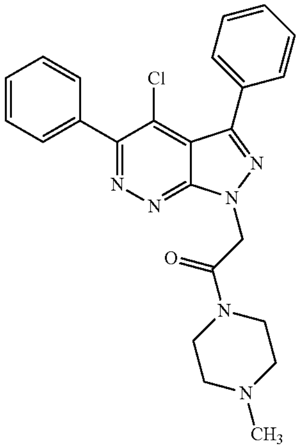
;
2
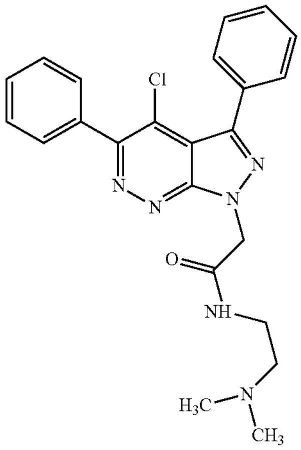
4
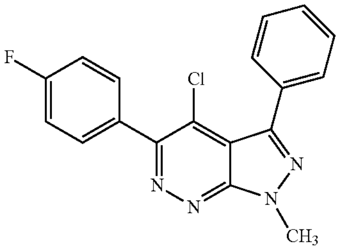
;
5
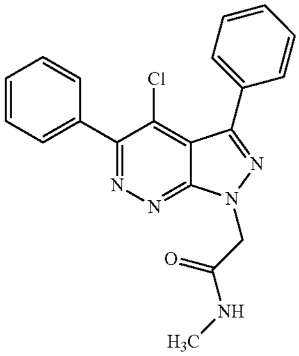
;
-continued
6
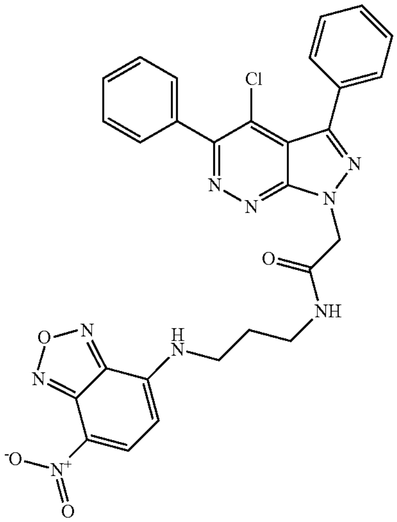
;
7
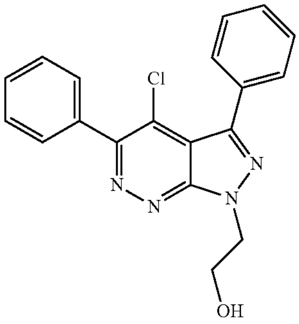
;
8
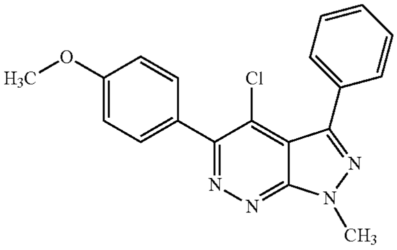
;
9
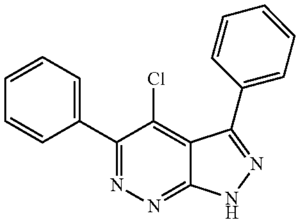
;
10
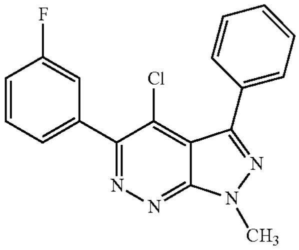
;

-continued
11
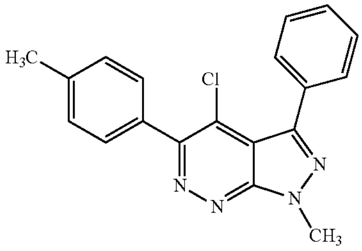
;
12
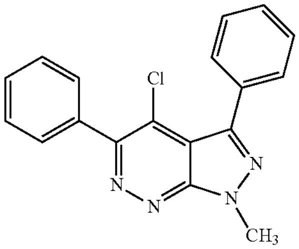
;
13
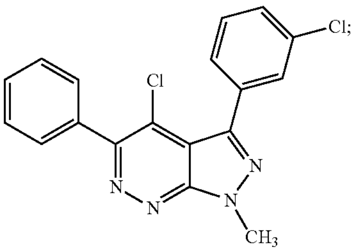
14
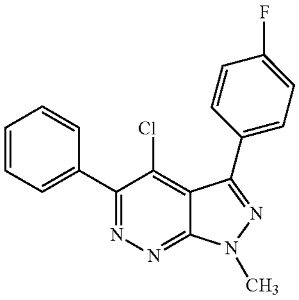
;
15
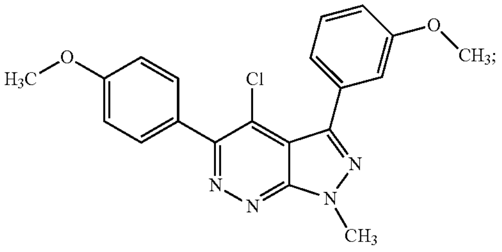
16
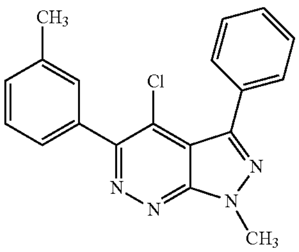
;
-continued
17
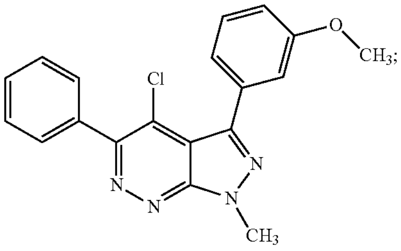
18
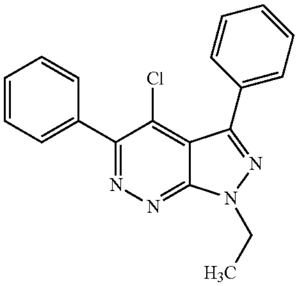
;
19
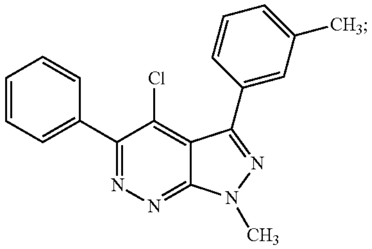
20
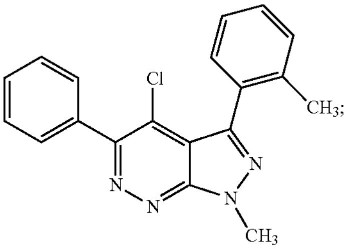
21
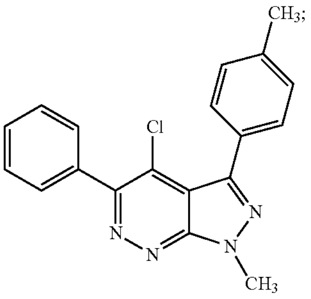
22
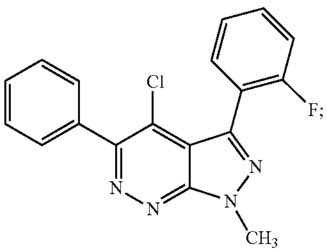

-continued
23
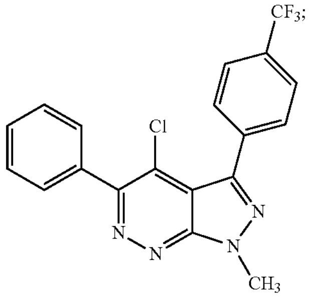
24
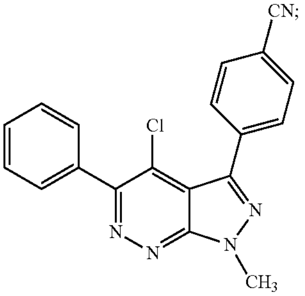
25
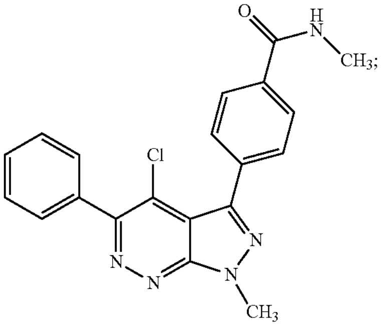
26
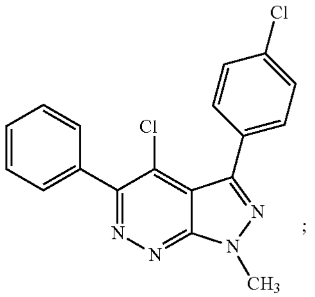
27
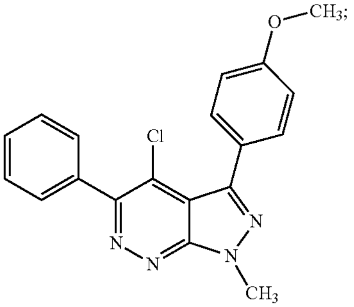
-continued
28
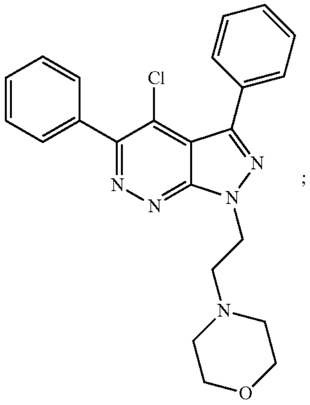
29
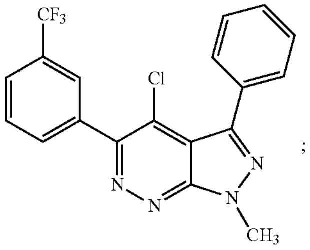
30
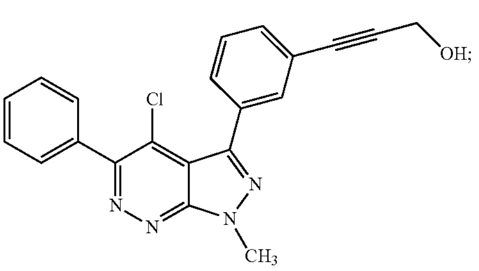
31
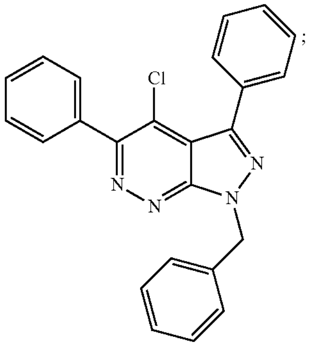
32
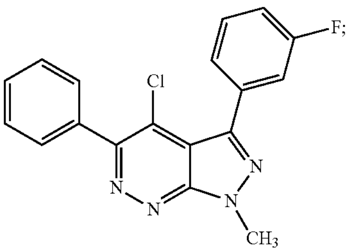

-continued
33
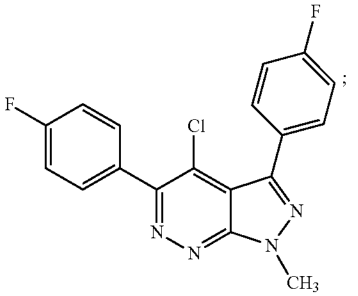
34
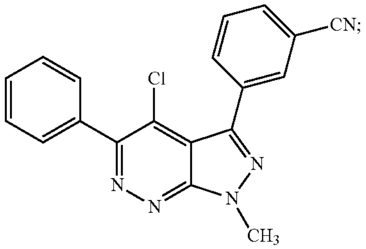
35
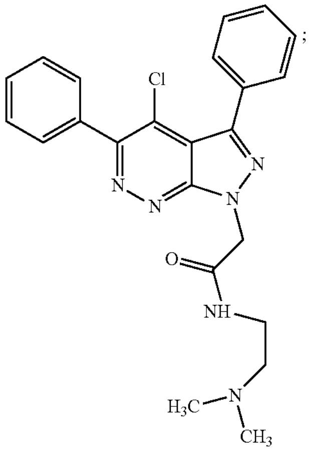
37
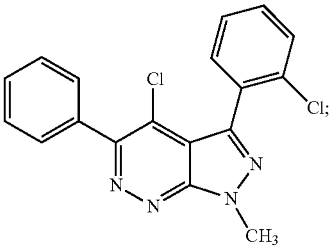
-continued
38
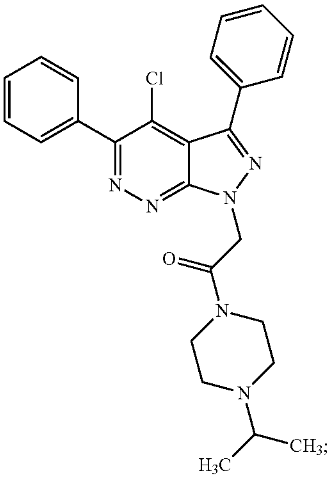
39
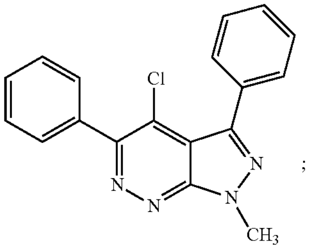
42
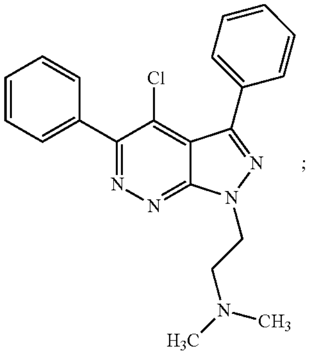
45
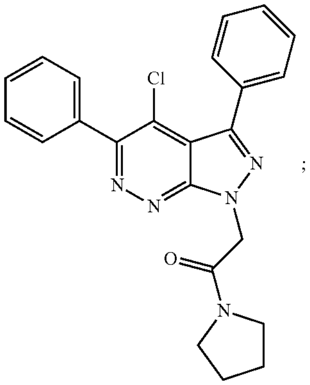

-continued
47
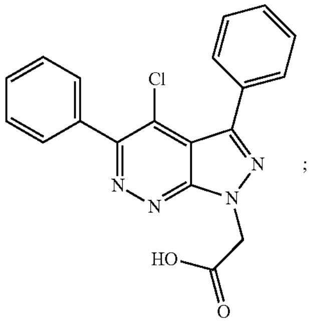
48
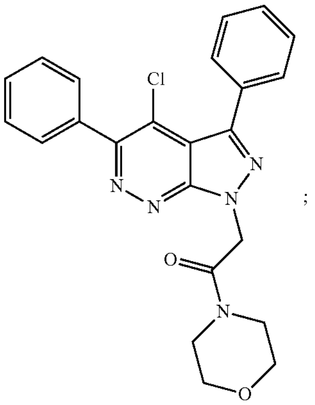
49
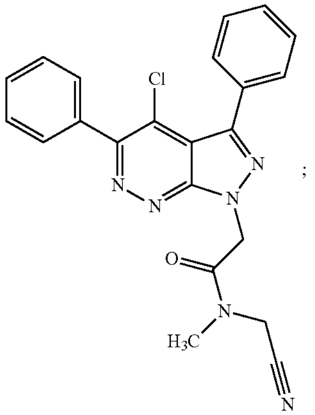
50
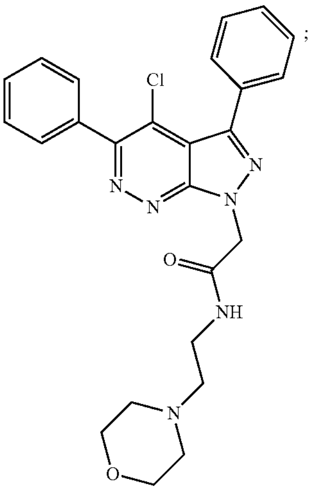
-continued
51
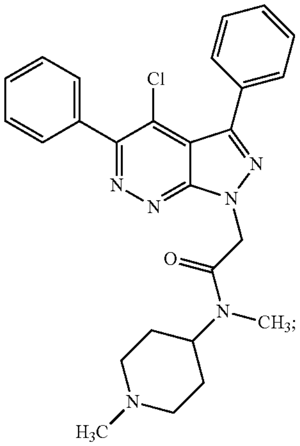
52
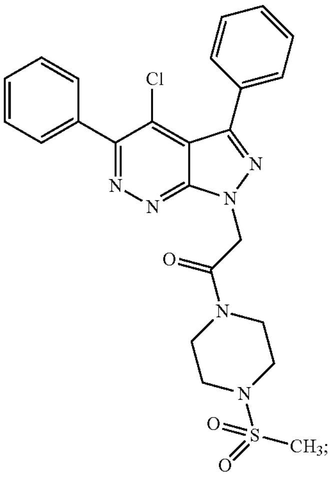
53
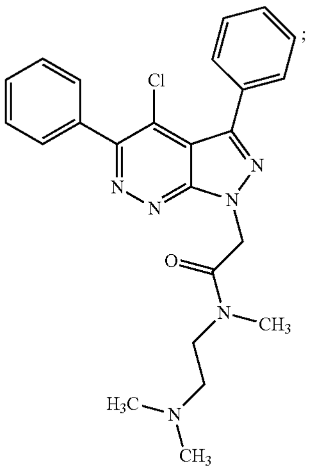

54
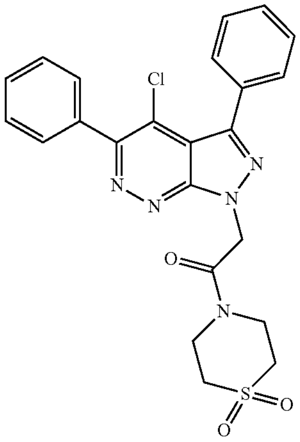
;
55
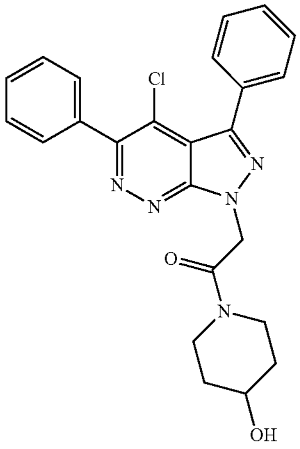
;
56
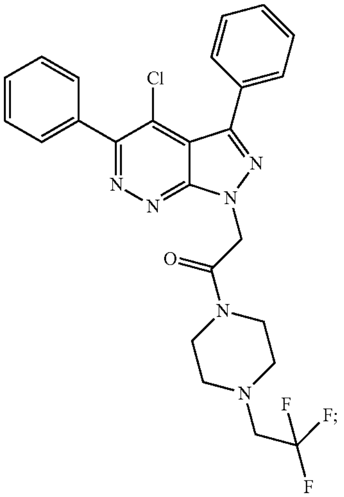
;
57
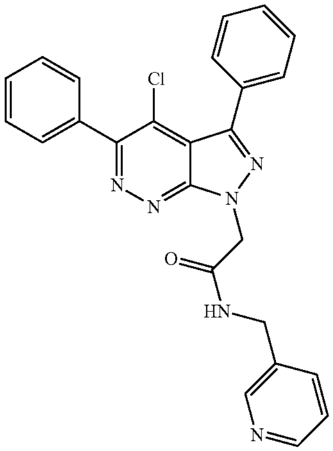
;
58
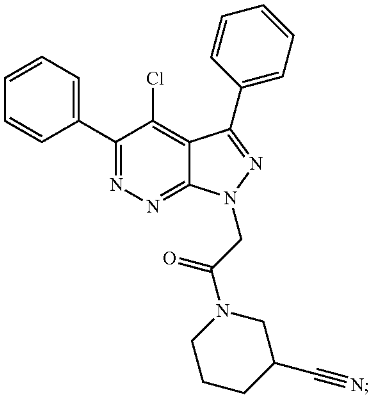
;
59
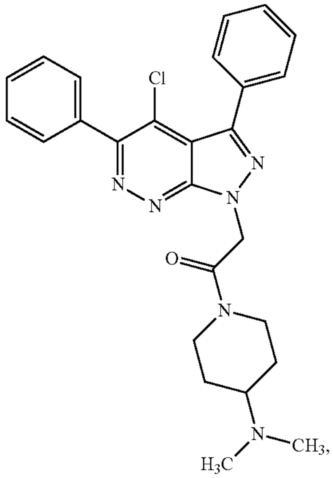
, -continued
60
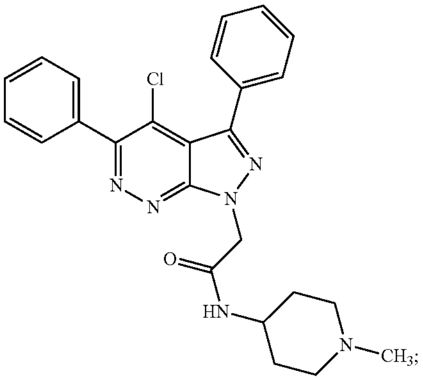
61
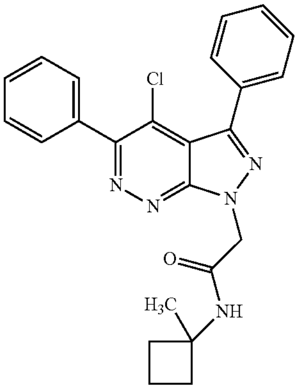
;
62
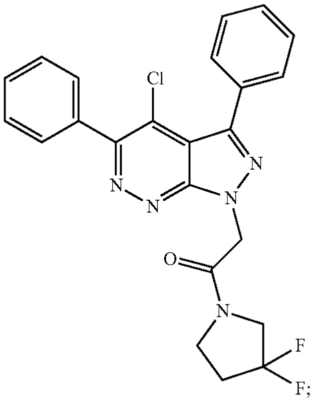
63
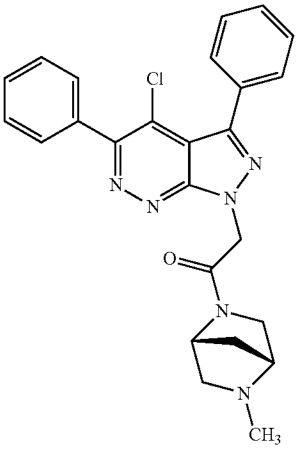
;
-continued
64
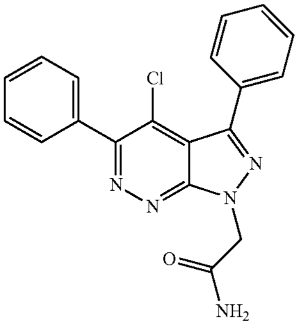
;
65
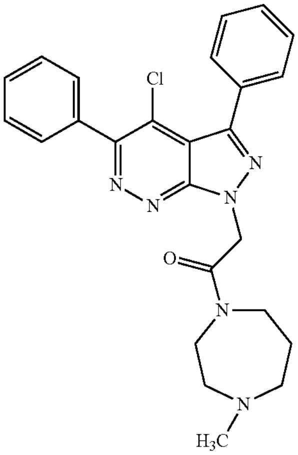
;
66
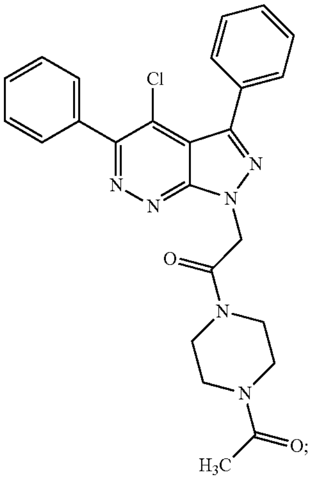

-continued
67
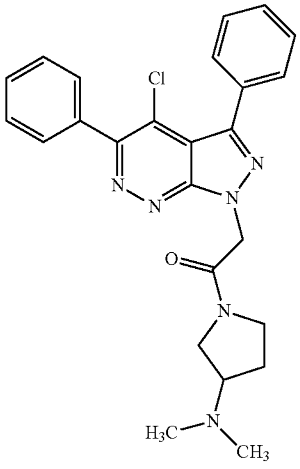
;
68
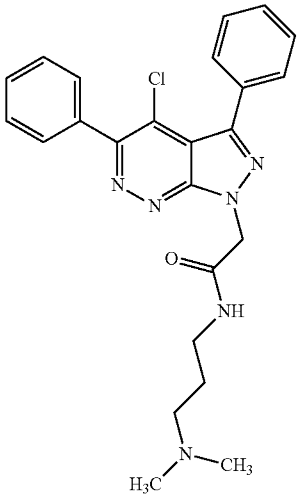
;
69
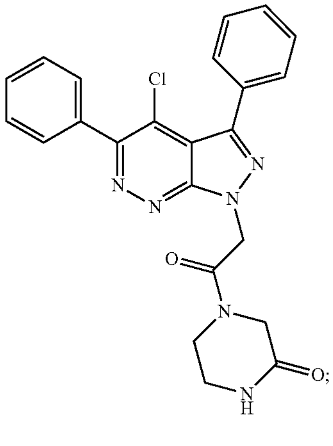
-continued
70
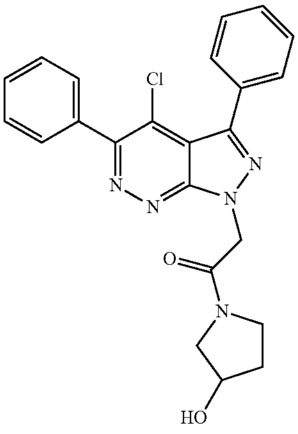
;
71
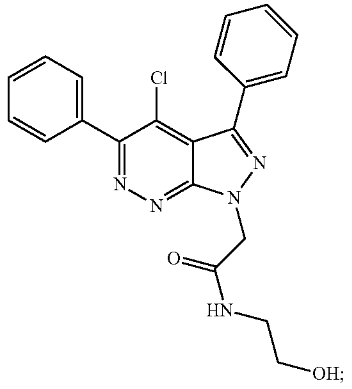
72
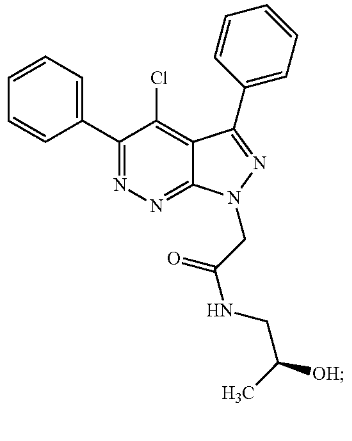

-continued
73
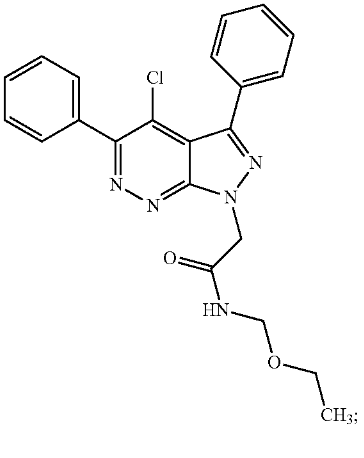
74
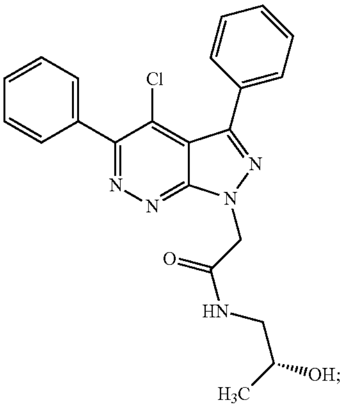
75
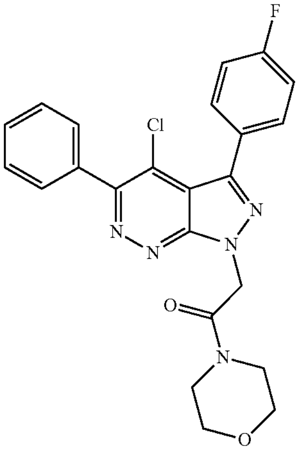
;
-continued
76
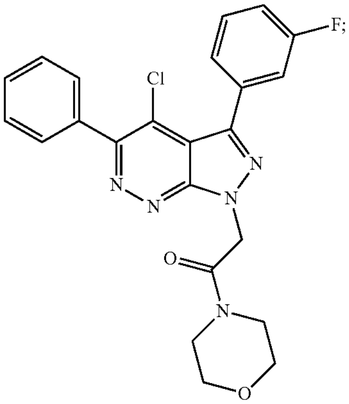
77
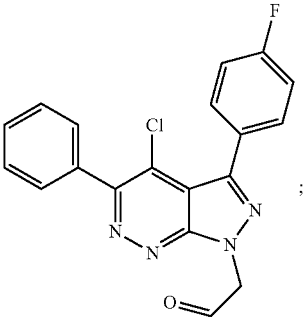
;
78
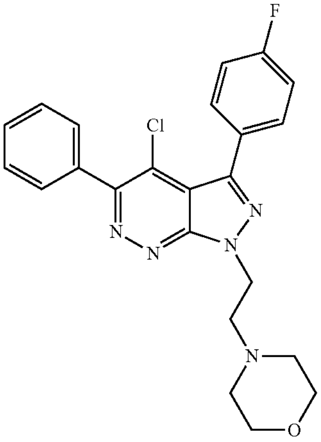
;
79
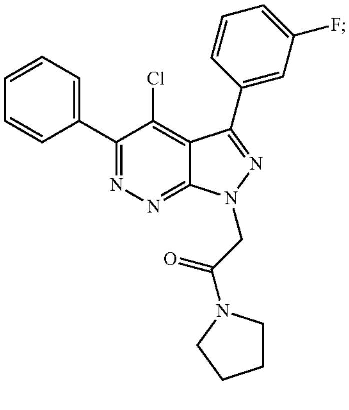

80
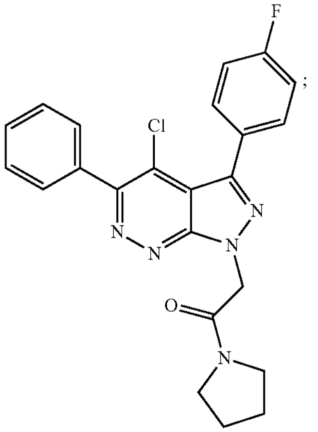
81
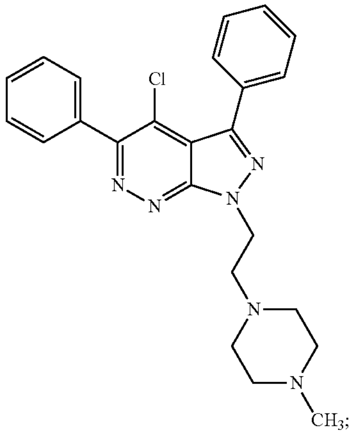
82
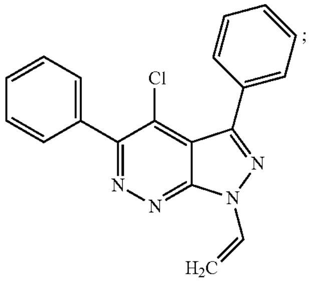
83
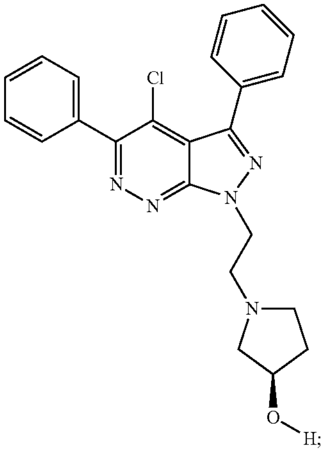
84
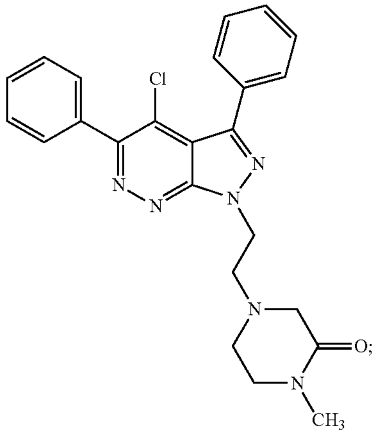
85
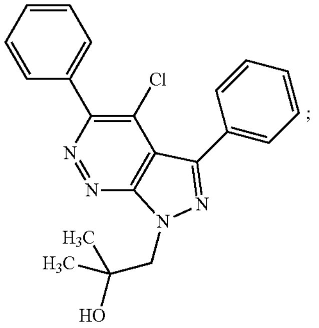
86
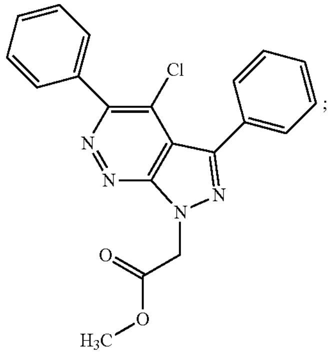
87
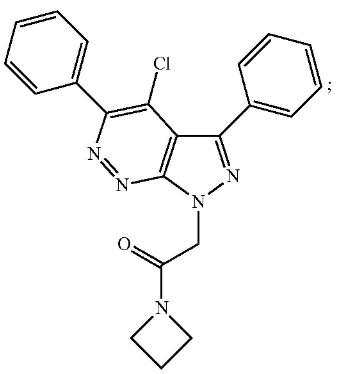

-continued
88
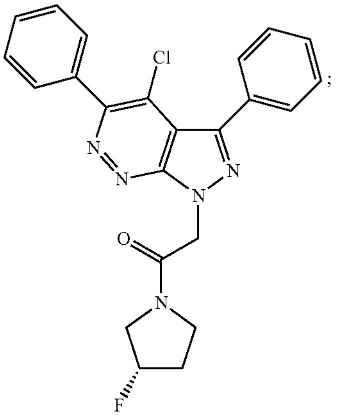
89
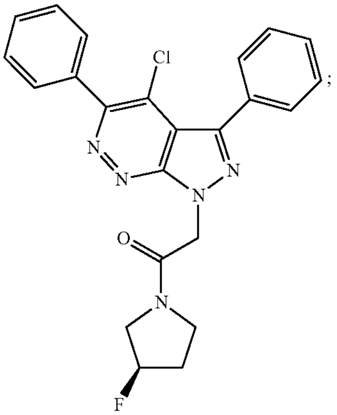
90
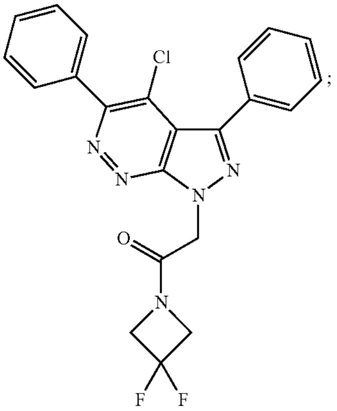
91
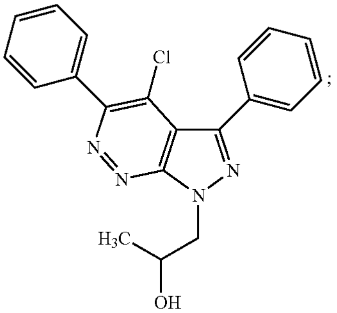
-continued
92
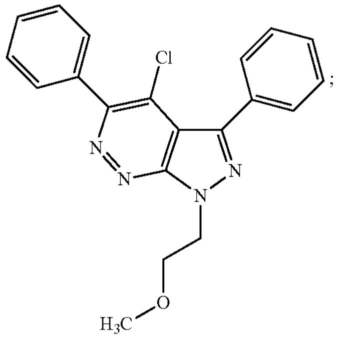
93
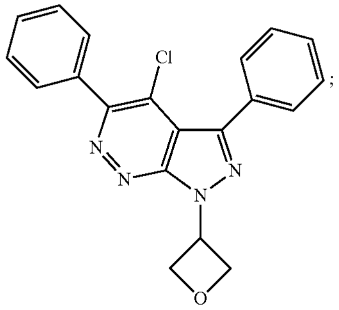
94
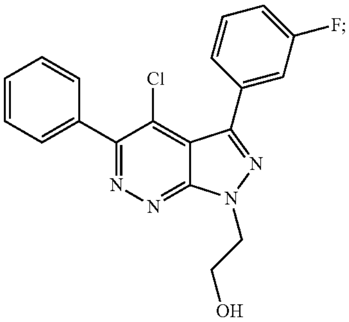
95
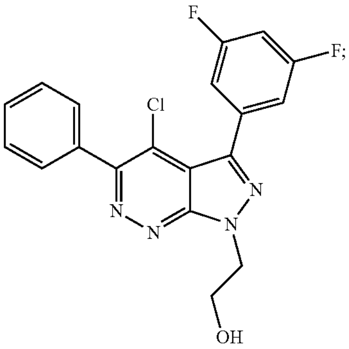

-continued
96
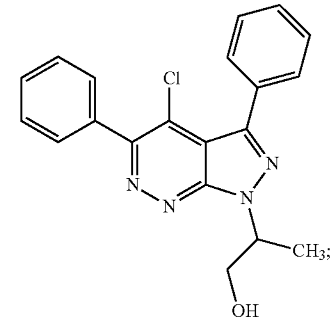
97
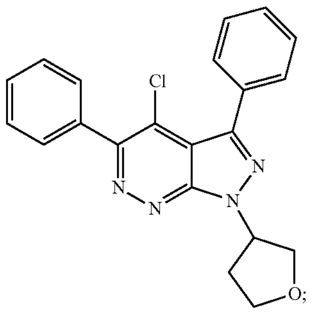
98
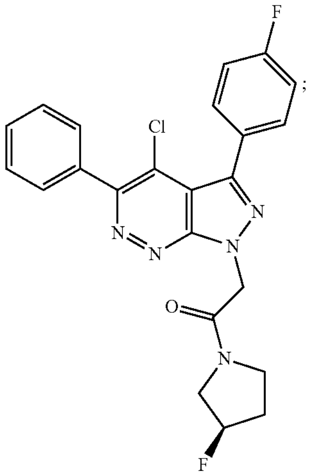
99
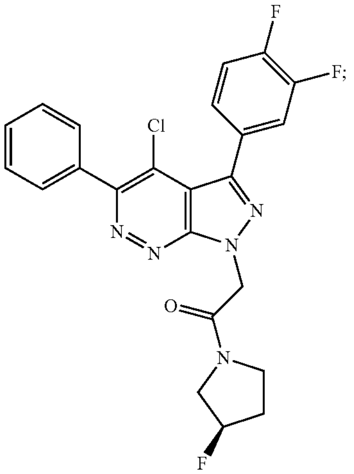
-continued
100
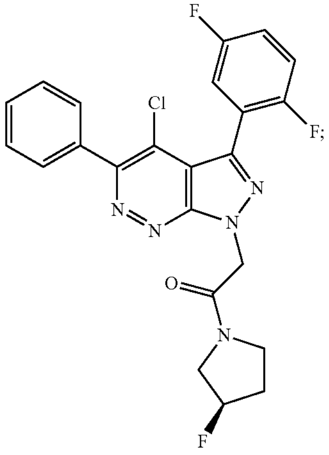
101
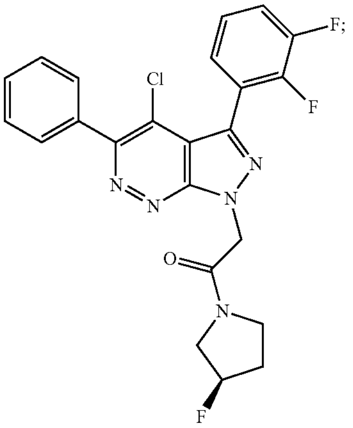
102
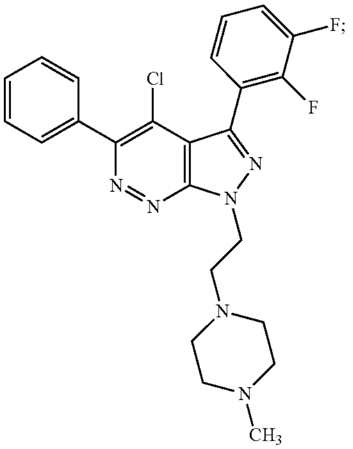

-continued
103
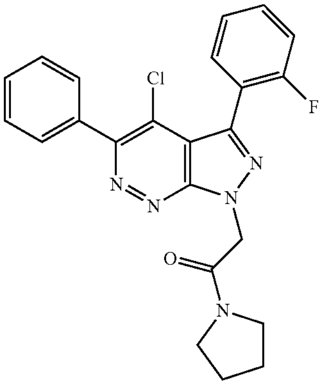
104
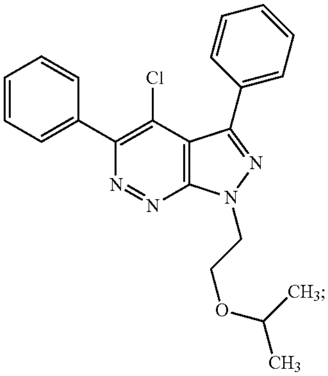
105
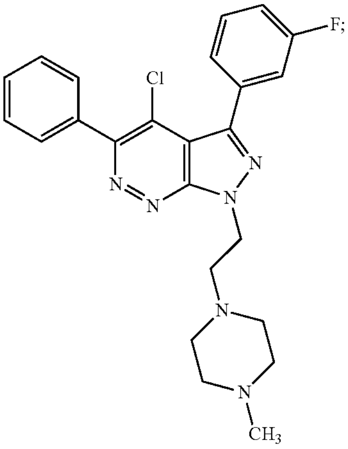
106
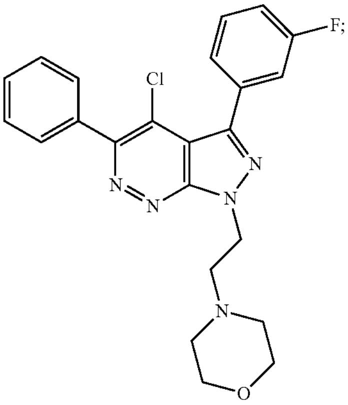
-continued
107
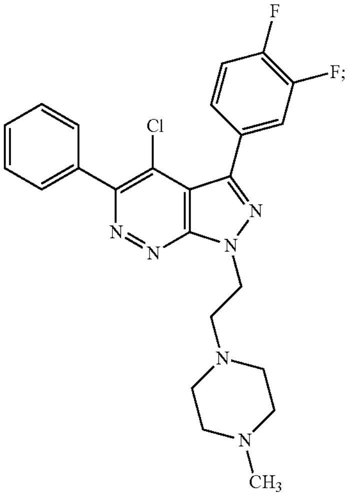
108
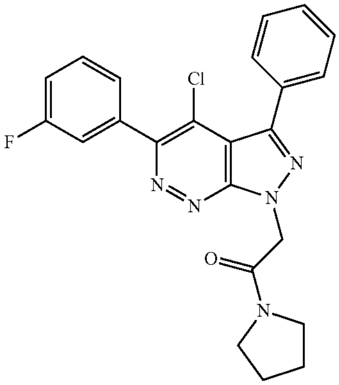
;
109
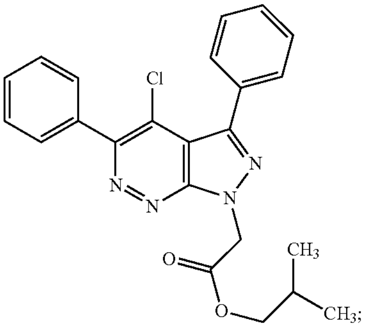
110
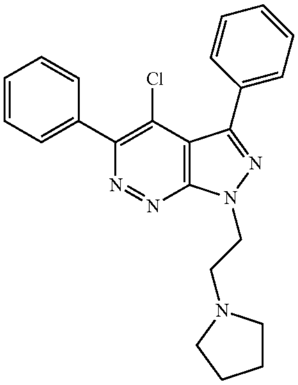
; or -continued

111

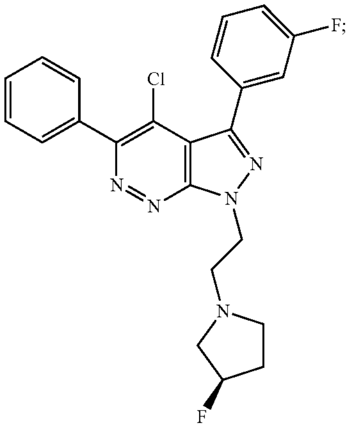

or a pharmaceutically acceptable salt thereof.

In some embodiments, the compound of the invention is Compound 85 or a pharmaceutically acceptable salt thereof.

Compounds of Formula III

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula III:

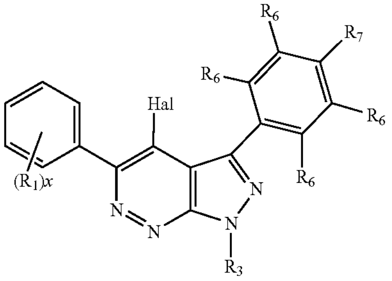

or a pharmaceutically acceptable salt thereof, wherein Hal is —Cl, —F, —I, or —Br, x is an integer ranging from 0 to 5;

each $R_1$ is independently —Cl, —F, —I, —Br, —$C_1$-$C_3$ alkyl, —O—$C_1$-$C_3$ alkyl; —CN; —$CF_3$. —C(O)NH($CH_3$), or —C≡$CCH_2$OH;

$R_3$ is —H, —$C_1$-$C_6$ alkyl, —($C_1$-$C_6$ alkylene)-OH, —($C_1$-$C_6$ alkylene)-phenyl, —($C_1$-$C_6$ alkylene)-O—($C_1$-$C_6$alkyl), —$C_2$-$C_6$ alkenyl, —($C_1$-$C_6$ alkylene)-C(O)$R_4$, —($C_1$-$C_6$ alkylene)-$R_5$,

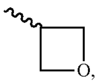

or

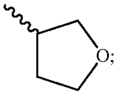

$R_4$ is —OH, —O—($C_1$-$C_6$ alkyl), —$NH_2$, —NH($C_1$-$C_6$ alkyl, —NH(—($C_1$-$C_6$ alkylene)-OH), —NH(—($C_1$-$C_6$ alkylene)N($C_1$-$C_6$ alkyl)$_2$), —N—($C_1$-$C_6$ alkyl)(($C_1$-$C_6$ alkylene)-CN), —N—($C_1$-$C_6$ alkyl)(($C_1$-$C_6$ alkylene)N($C_1$-$C_6$ alkyl)$_2$), —NH—($C_1$-$C_6$ alkylene)-O—($C_1$-$C_6$ alkyl),

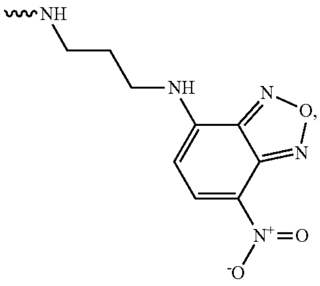

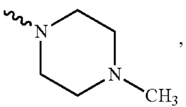

,

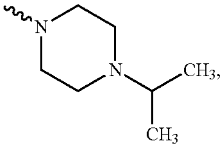

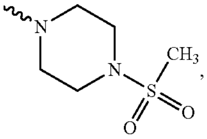

,

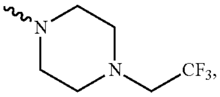

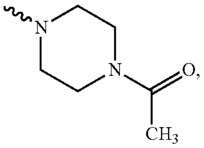

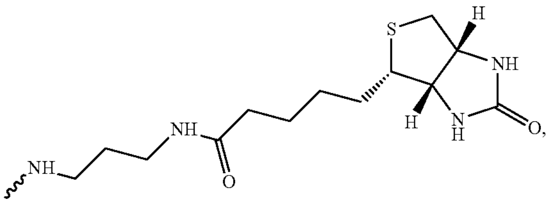

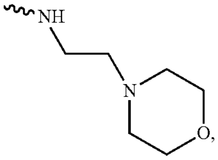

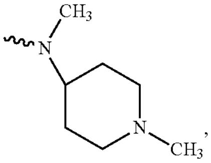

,

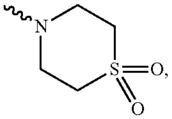

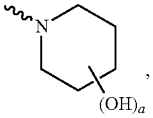

,

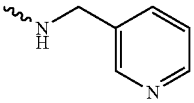

,

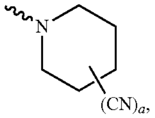

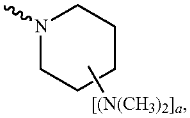

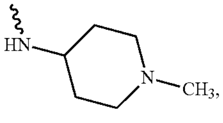

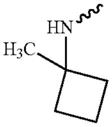

,

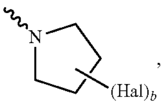

,

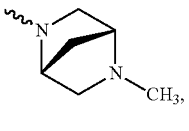

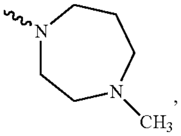

,

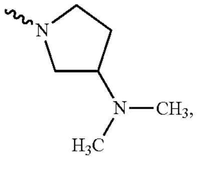

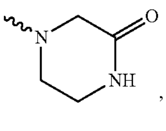

,

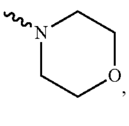

-continued

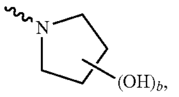 or 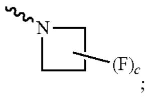 ;

a is an integer ranging from 0 to 10;
b is an integer ranging from 0 to 8;
c is an integer ranging from 0 to 6;
$R_5$ is

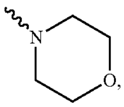 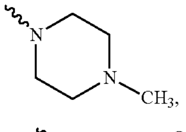

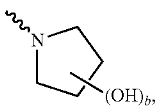 or 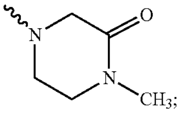

wherein each $R_6$ and $R_7$ is independently —H or —I, wherein at least one of $R_6$ and $R_7$ is —I, and wherein when $R_3$ is —$C_1$-$C_3$ alkyl, $R_7$ is —H.

In certain embodiments, one $R_6$ in the ortho position relative to the pyrazolopyridazino ring system is iodo and the remaining $R_6$ and $R_7$ groups are hydrogen. In other embodiments, one $R_6$ in the para position relative to the pyrazolopyridazino ring system is iodo and the remaining $R_6$ and $R_7$ groups are hydrogen. In further embodiments, one $R_6$ in the ortho position relative to the pyrazolopyridazino ring system and one $R_6$ in the para position relative to the pyrazolopyridazino ring system are iodo and the remaining $R_6$ and $R_7$ groups are hydrogen. In further embodiments, the two $R_6$ groups in the ortho positions relative to the pyrazolopyridazino ring system and one $R_6$ in the para position relative to the pyrazolopyridazino ring system are iodo and the remaining $R_6$ and $R_7$ groups are hydrogen. In further embodiments, the two $R_6$ groups in the para positions relative to the pyrazolopyridazino ring system and one $R_6$ in the ortho position relative to the pyrazolopyridazino ring system are iodo and the remaining $R_6$ and $R_7$ are hydrogen. In certain embodiments, all $R_6$ groups are iodo and $R_7$ is hydrogen. In yet further embodiments, $R_7$ is iodo and the $R_6$ groups are hydrogen.

In a particular embodiment, one $R_6$ in the para position relative to the pyrazolopyridazino ring system is iodo and $R_3$ is —$CH_3$.

In certain embodiments, Hal is —Cl. In yet another embodiment, x is 0. In another embodiment, x is 1. In a certain embodiments, x is 2.

In particular embodiments, x is 1 and $R_1$ is in the ortho position relative to the pyrazolopyridazino ring system. In certain embodiments, x is 1 and $R_1$ is in the para position relative to the pyrazolopyridazino ring system. In further embodiments, x is 1 and $R_1$ is in the meta position relative to the pyrazolopyridazino ring system.

In particular embodiments, x is 2 and $R_1$ is in the ortho and meta position relative to the pyrazolopyridazino ring system. In certain embodiments, x is 2 and $R_1$ is in the ortho and para position relative to the pyrazolopyridazino ring system. In further embodiments, x is 2 and $R_1$ is in the para and meta position relative to the pyrazolopyridazino ring system.

In yet other embodiments, $R_1$ is —Cl. In certain embodiments, $R_1$ is —F. In certain embodiments. $R_1$ is —I. In further embodiments, $R_1$ is —$OCH_3$. In other embodiments, $R_1$ is —$CH_3$. In yet other embodiments, $R_1$ is —C(O)N(H)$CH_3$. In certain embodiments, $R_1$ is —$CF_3$. In further embodiments, $R_1$ is —CN. In additional embodiments, $R_1$ is —C═C$CH_2$OH.

In yet other embodiments, x is 1 or 2, and $R_1$ is —Cl, —F, —Br, —I, —$OCH_3$, —$CH_3$, —C(O)N(H)$CH_3$, —$CF_3$, —CN or —C≡C$CH_2$OH.

In yet other embodiments, Hal is x is 1 or 2, and $R_1$ is —Cl, —F, —Br, —I, —$OCH_3$, —$CH_3$, —C(O)N(H)$CH_3$, —$CF_3$, —CN or In particular embodiments. $R_3$ is —H. In certain embodiments, $R_3$ is —$CH_3$. In further embodiments, $R_3$ is —$CH_2CH_3$. In still further embodiments. $R_3$ is —$CHCH_2$. In other embodiments, $R_3$ is —$CH_2CH_2OH$. In particular embodiments. $R_3$ is —$(CH_2)_2C_6H_5$. In other embodiments, $R_3$ is —$CH_2$C(O)OH. In yet other embodiments. $R_3$ is —$CH_2$C(O)N(H)$CH_3$. In certain embodiments, $R_3$ is —$CH_2$C(O)N(H)(($CH_2)_2$N($CH_3)_2$). In yet other embodiments, $R_3$ is —$CH_2$C(O)N(H)(($CH_2)_3$N($CH_3)_2$). In other embodiments, $R_3$ is —$CH_2$C(O)N($CH_3$)$CH_2$CN. In particular embodiments. $R_3$ is —$CH_2$C(O)$NH_2$. In certain embodiments, $R_3$ is —$CH_2$C(O)N(H)(($CH_2)_2$OH). In other embodiments, $R_3$ is —$CH_2$C(O)N(H)(($CH_2)_2OCH_3$). In still further embodiments, $R_3$ is —$CH_2C(CH_3)_2OH$. In yet other embodiments, $R_3$ is —$CH_2$C(O)$OCH_3$. In further embodiments, $R_3$ is —$CH_2$CH(OH)$CH_3$. In still further embodiments, $R_3$ is —$CH_2CH_2OH$. In particular embodiments, $R_3$ is —CF($CH_3$)$CH_2$OH.

In further embodiments, $R_3$ is —$CH_2$C(O)$R_4$ and $R_4$ is

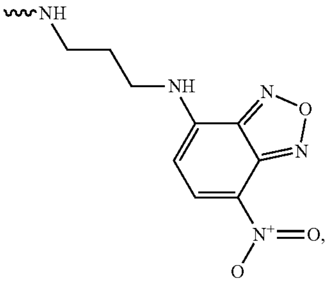

In other embodiments, $R_3$ is —$CH_2$C(O)$R_4$ and $R_4$ is

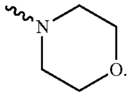

In particular embodiments, $R_3$ is —$CH_2$C(O)$R_4$ and $R_4$ is

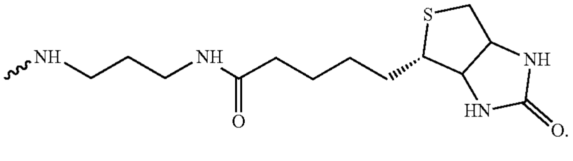

In yet other embodiments, $R_3$ is —$CH_2C(O)R_4$ and $R_4$ is

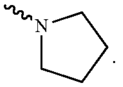

In certain embodiments, $R_3$ is —$CH_2C(O)R_1$ and $R_4$ is

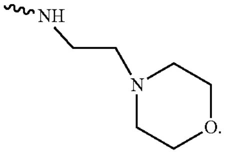

In other embodiments, $R_3$ is —$CH_2C(O)R_4$ and $R_4$ is

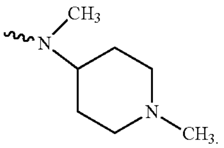

In particular embodiments, $R_3$ is —$CH_2C(O)R_4$ and $R_4$ is

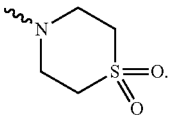

In yet other embodiments, $R_3$ is —$CH_2C(O)R_4$ and $R_4$ is

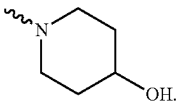

In certain embodiments, $R_3$ is —$CH_2C(O)R_4$ and $R_4$ is

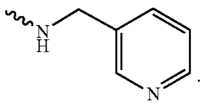

In other embodiments, $R_3$ is —$CH_2C(O)R_4$ and $R_4$ is

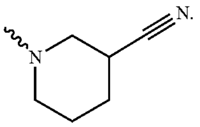

In particular embodiments, $R_3$ is —$CH_2C(O)R_4$ and $R_4$ is

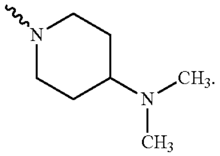

In yet other embodiments, $R_3$ is —$CH_2C(O)R_4$ and $R_4$ is

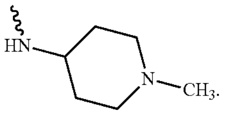

In certain embodiments, $R_3$ is —$CH_2C(O)R_4$ and $R_4$ is

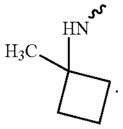

In certain embodiments, $R_3$ is —$CH_2C(O)R_4$ and $R_4$ is

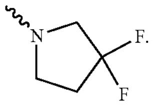

In particular embodiments, $R_3$ is —$CH_2C(O)R_4$ and $R_4$ is

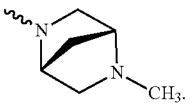

In yet other embodiments, $R_3$ is —$CH_2C(O)R_4$ and $R_4$ is

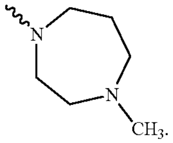

In certain embodiments, $R_3$ is —$CH_2C(O)R_4$ and $R_4$ is

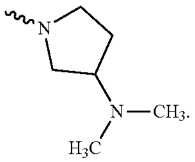

In other embodiments, $R_3$ is —$CH_2C(O)R_4$ and $R_4$ is

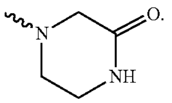

In particular embodiments, $R_3$ is —$CH_2C(O)R_4$ and $R_4$ is

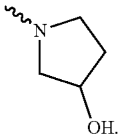

In yet other embodiments, $R_3$ is —$CH_2C(O)R_4$ and $R_4$ is

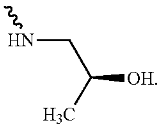

In certain embodiments, $R_3$ is —$CH_2C(O)R_4$ and $R_4$ is

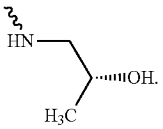

In other embodiments, $R_3$ is —$CH_2C(O)R_4$ and $R_4$ is

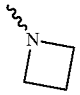

In particular embodiments, $R_3$ is —$CH_2C(O)R_4$ and $R_4$ is

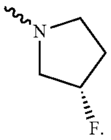

In yet other embodiments, $R_3$ is —$CH_2C(O)R_4$ and $R_4$ is

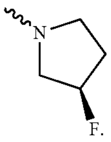

In certain embodiments, $R_3$ is —$CH_2C(O)R_4$ and $R_4$ is

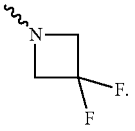

In other embodiments, $R_3$ is —$CH_2C(O)R_4$ and $R_4$ is

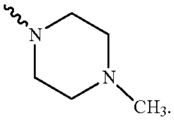

In further embodiments of the invention, $R_3$ is —$CH_2C(O)R_4$ and $R_4$ is

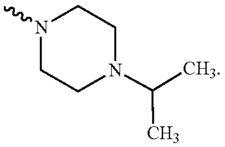

In certain embodiments of the invention, $R_3$ is —$CH_2C(O)R_4$ and $R_4$ is

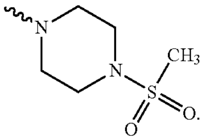

In other embodiments of the invention, $R_3$ is —$CH_2C(O)R_4$ and $R_4$ is

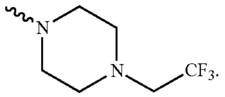

In further embodiments, $R_3$ is —$CH_2C(O)R_4$ and $R_4$ is

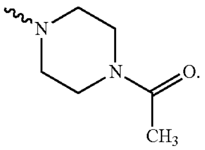

In further embodiments, $R_3$ is —$CH_2C(O)R_4$ and $R_4$ is

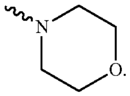

In particular embodiments, $R_3$ is $-(CH_2)_2R_5$ and $R_5$ is

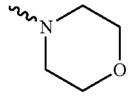

In yet other embodiments, $R_3$ is $-(CH_2)_2R_5$ and $R_5$ is

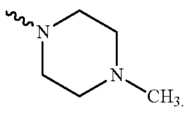

In certain embodiments, $R_3$ is $-(CH_2)_2R_5$ and $R_5$ is

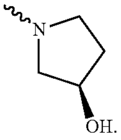

In other embodiments, invention, $R_3$ is $-(CH_2)_2R_5$ and $R_5$ is

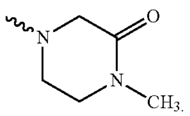

In some embodiments, a is an integer ranging from 0 to 5. In some embodiments, b is an integer ranging from 0 to 4. In some embodiments, c is an integer ranging from 0 to 6.

In certain embodiments, the compound of Formula III is Compound 3, which has the structure:

3

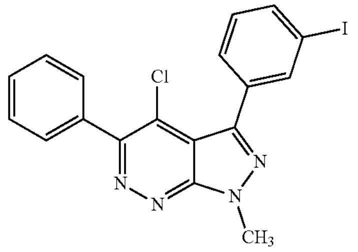

or a pharmaceutically acceptable salt thereof.

Compounds of Formula IV

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula IV:

Formula IV

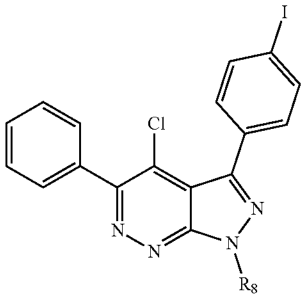

or a pharmaceutically acceptable salt thereof, wherein $R_8$ is $-C_1$-$C_3$ alkyl.

In certain embodiments of the invention, $R_8$ is $-CH_3$, in yet further embodiments of the invention, $R_8$ is $-CH_2CH_3$. In other embodiments of the invention, $R_8$ is $CH_2CH_2CH_3$. In other embodiments of the invention. $R_8$ is $-CH(CH_3)_2$.

In certain embodiments, the compound of Formula IV is Compound 43, which has the structure:

43

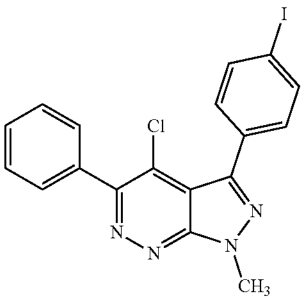

or a pharmaceutically acceptable salt thereof.

Compounds of Formula V

In one embodiment, the invention provides methods for treating or preventing cancer, an inflammatory disease or an autoimmune disease, or for reducing, risk of developing cancer, an inflammatory disease or an autoimmune disease, comprising administering to a subject in need thereof an effective amount of a compound of Formula V:

Formula V

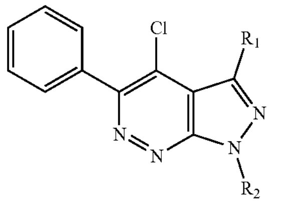

or a pharmaceutically acceptable salt thereof, wherein $R_1$ is:

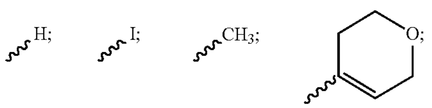

-continued
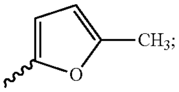
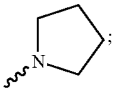
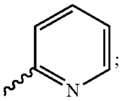
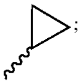
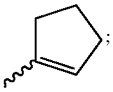
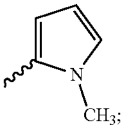
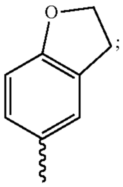
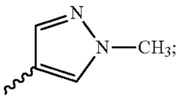
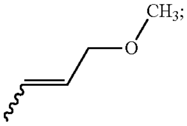
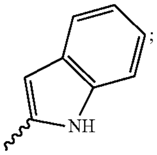
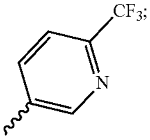
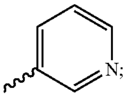
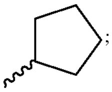
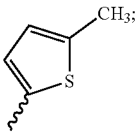
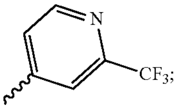
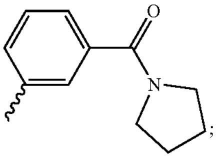
or
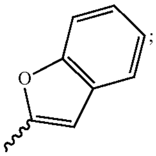
$R_2$ is:
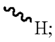
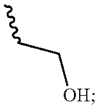
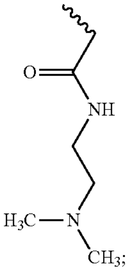
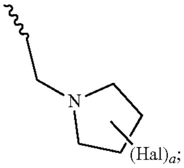
-continued
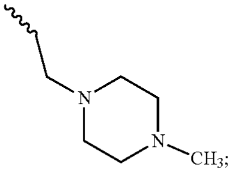
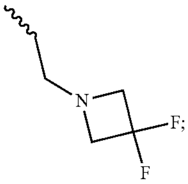
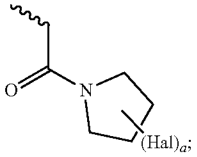
or
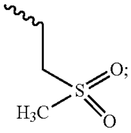
Hal is —Cl, —F, —I, or —Br; and
a is 0, 1, or 2.
In particular embodiments, $R_1$ is —I. In other embodiments, $R_1$ is —H. In yet other embodiments, $R_1$ is —$CH_3$. In certain embodiments, $R_1$ is —$CF_3$.
In yet other embodiments, $R_1$ is
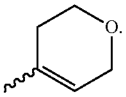
In certain embodiments, $R_1$ is
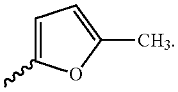
In still further embodiments, $R_1$ is
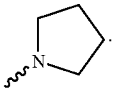
In particular embodiments, $R_1$ is
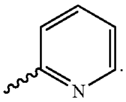
In other embodiments, $R_1$ is
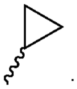

In yet other embodiments, $R_1$ is

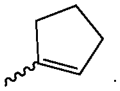

In certain embodiments, $R_1$ is

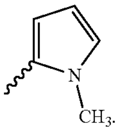

In particular embodiments, $R_1$ is

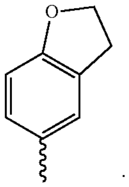

In certain embodiments, $R_1$ is

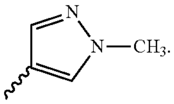

In still further embodiments, $R_1$ is

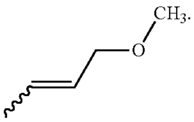

In other embodiments, $R_1$ is

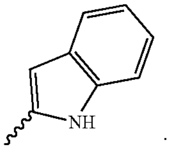

In yet other embodiments, $R_1$ is

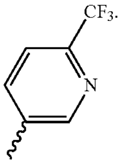

In certain embodiments, $R_1$ is

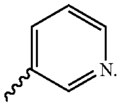

In still further embodiments, $R_1$ is

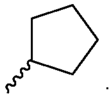

In other embodiments, $R_1$ is

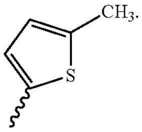

In particular embodiments, $R_1$ is

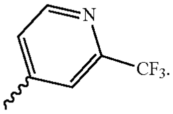

In further embodiments, $R_1$ is

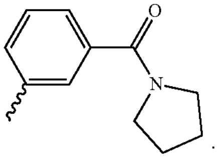

In still further embodiments, $R_1$ is

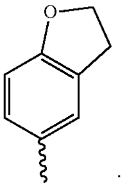

In certain embodiments, $R_2$ is —H. In yet other embodiments, $R_2$ is

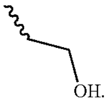

In particular embodiments, $R_2$ is

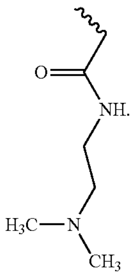

In yet other embodiments, $R_2$ is

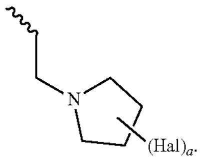

In further embodiments, $R_2$ is

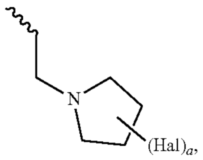

a=1, and Hal is —F.

In certain embodiments, $R_2$ is

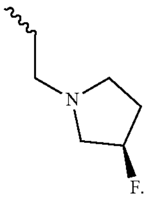

In still further embodiments, $R_2$ is

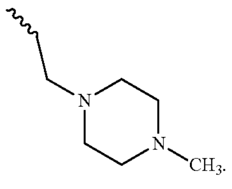

In particular embodiments, $R_2$ is

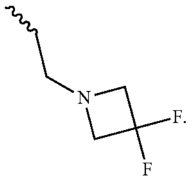

In other embodiments, $R_2$ is

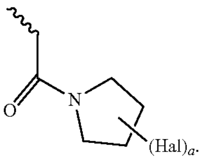

In yet other embodiments, $R_2$ is

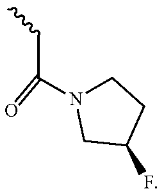

In certain embodiments, $R_2$ is

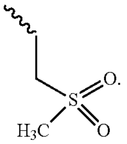

In further embodiments, when a is 2, each Hal is the same or different.

In certain embodiments the compound of Formula V has the structure:

Va

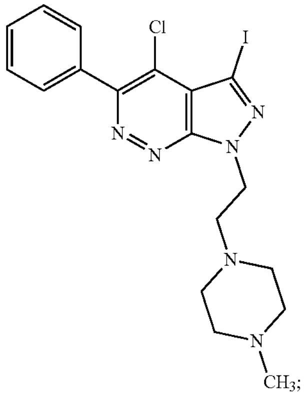

-continued
Vb
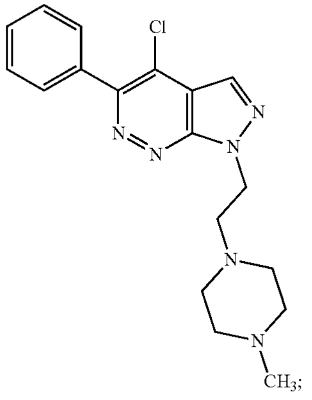
Vc
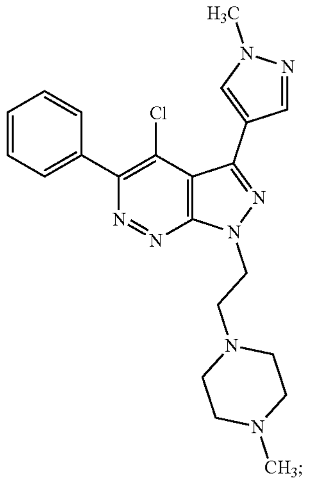
Vd
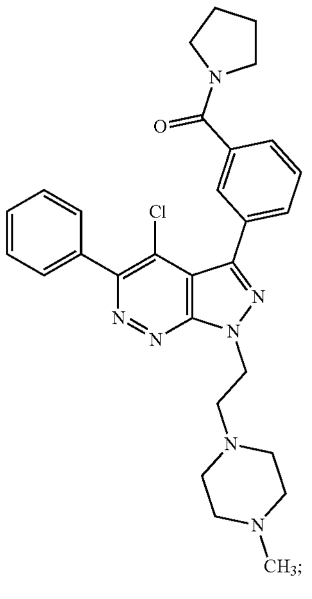
-continued
Ve
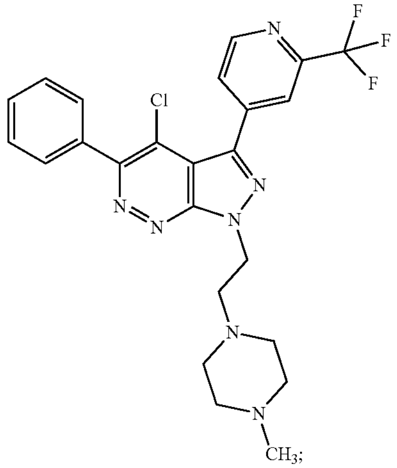
Vf
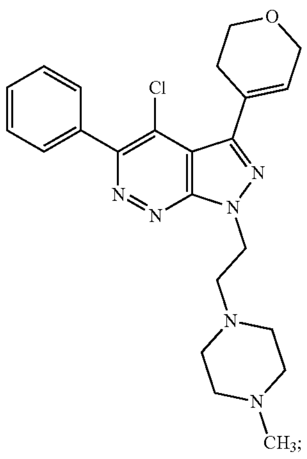
Vg
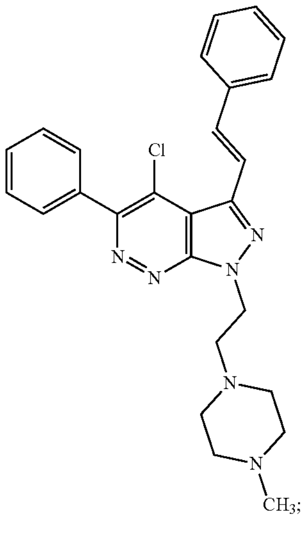

-continued
Vh
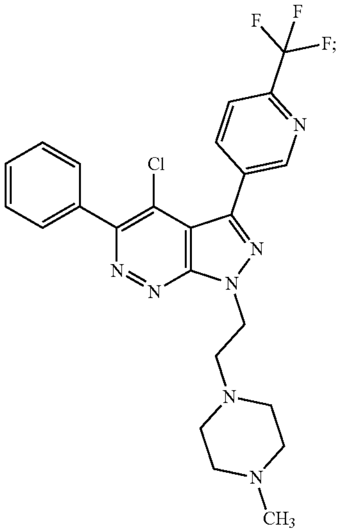
Vi
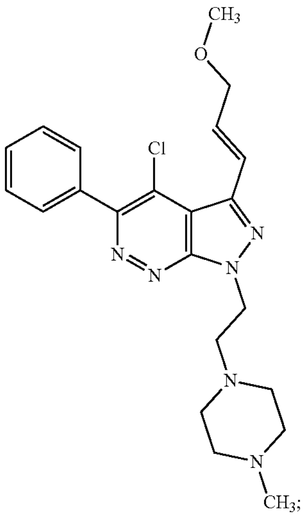
Vj
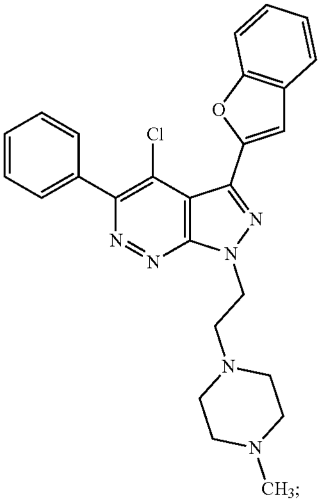
-continued
Vk
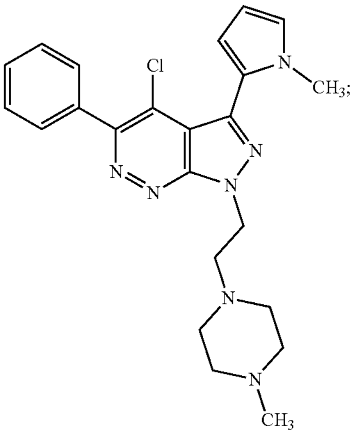
Vl
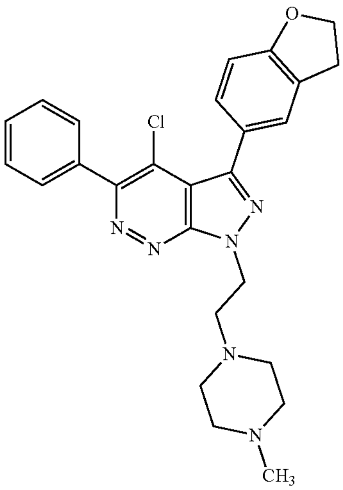
;
Vm
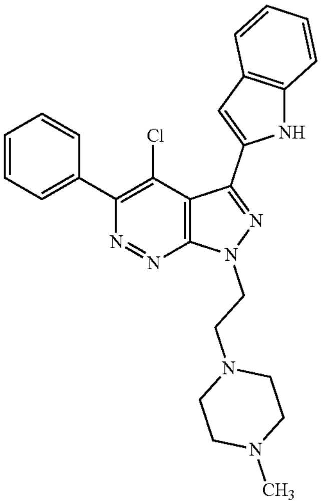
;

-continued
Vn
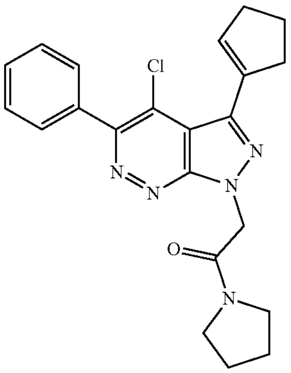
;
Vo
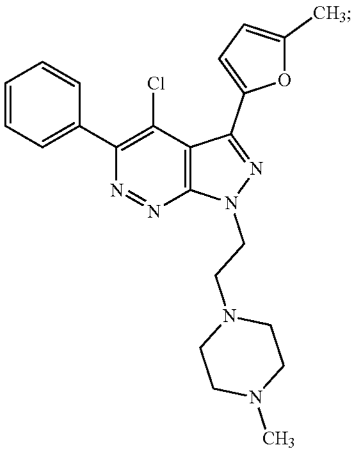
Vp
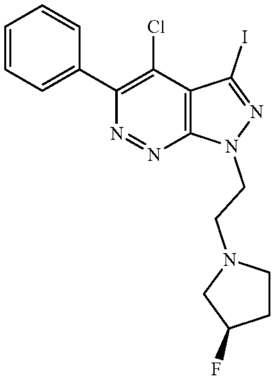
;
Vq
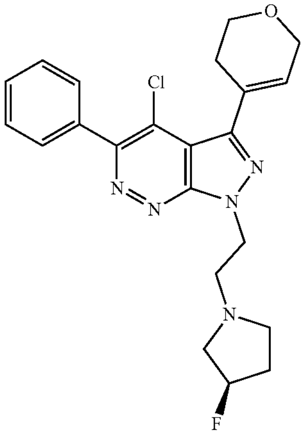
;
-continued
Vr
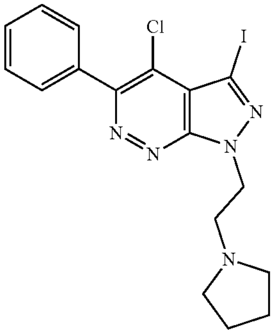
;
Vs
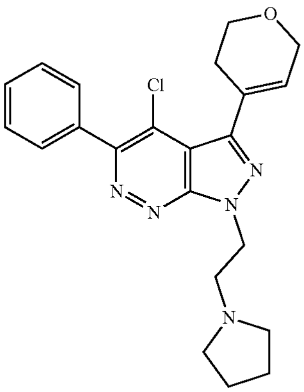
;
Vt
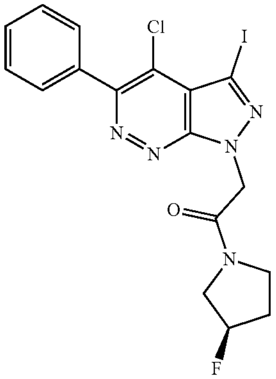
;
Vu
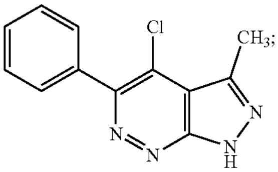

Vv
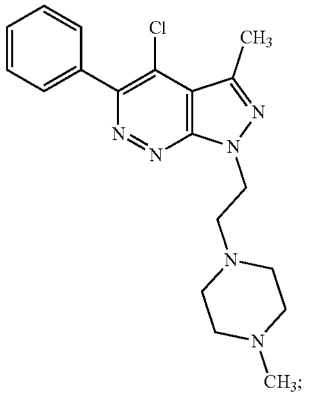
Vw
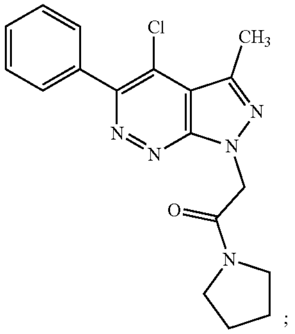
Vx
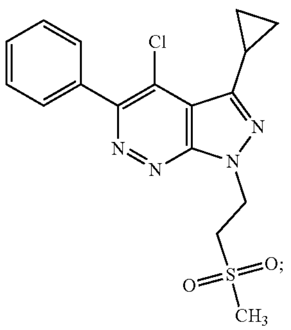
Vy
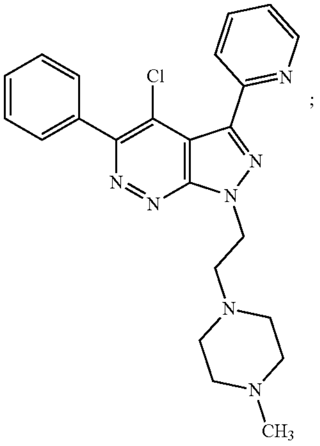
Vz
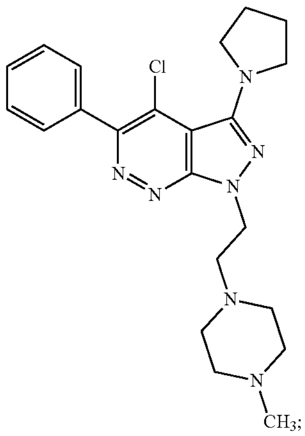
Vaa
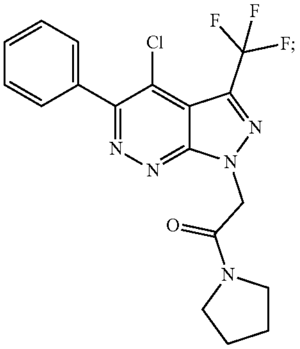
Vbb
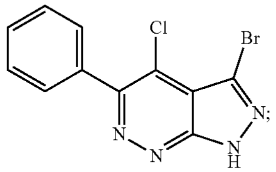
Vcc
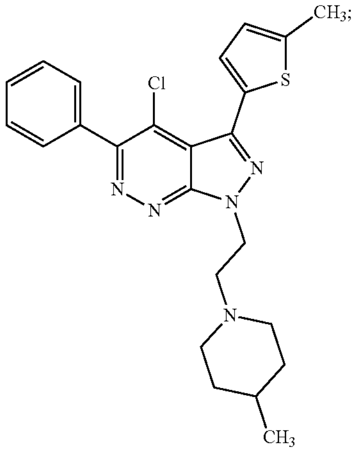
Vdd
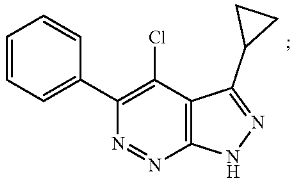

-continued

Vee

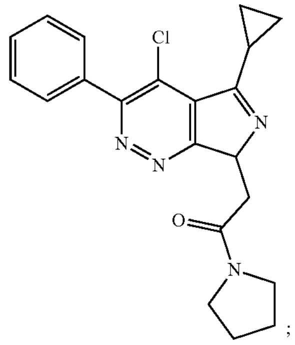

Vff

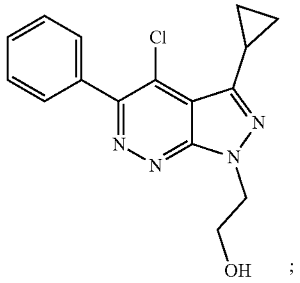

Vgg

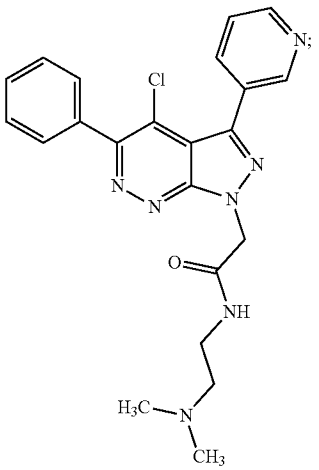

Vhh

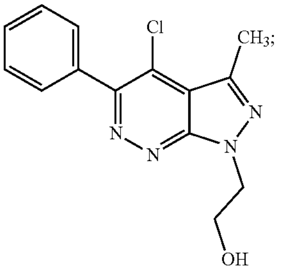

or

-continued

Vii

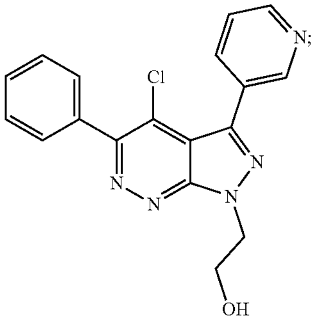

or a pharmaceutically acceptable salt thereof.

Compounds of Formula VI

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula VI:

Formula VI

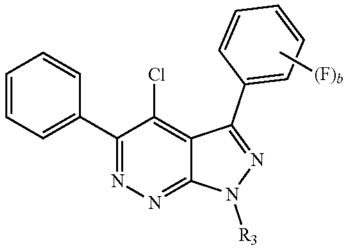

or a pharmaceutically acceptable salt thereof, wherein $R_3$ is:

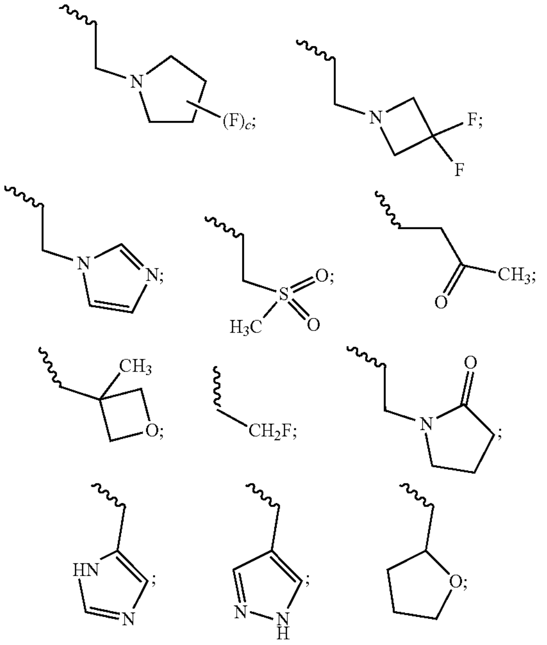

-continued

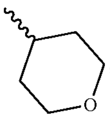;
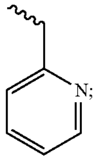;
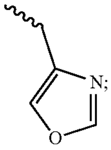;

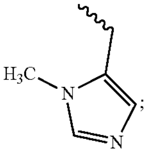;
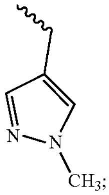;
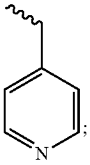;
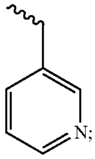;

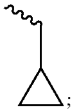;
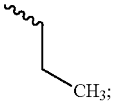;
or
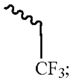;

b is 0 or 1; and c is 1 or 2.

In particular embodiments, b is 0. In other embodiments b is 1 and the —F is in the meta position relative to the pyrazolopyridazino ring system. In yet other embodiments b is 1 and the —F is in the para position relative to the pyrazolopyridazino ring system.

In particular embodiments $R_3$ is —$CF_3$. In certain embodiments $R_3$ is

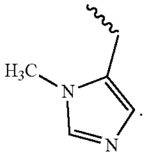

In other embodiments $R_3$ is

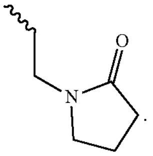

In yet other embodiments $R_3$ is

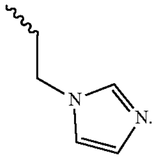

In further embodiments $R_3$ is

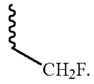

In still further embodiments $R_3$ is

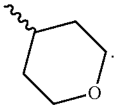

In particular embodiments $R_3$ is

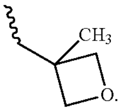

In other embodiments $R_3$ is

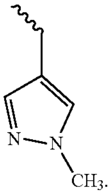

In yet other embodiments $R_3$ is

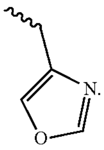

In certain embodiments $R_3$ is

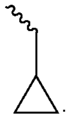

In further embodiments $R_3$ is

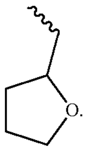

In further embodiments $R_3$ is

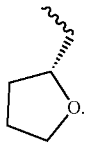

In certain embodiments $R_3$ is

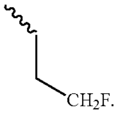

In other embodiments $R_3$ is

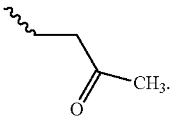

In yet other embodiments $R_3$ is

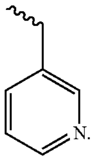

In further embodiments $R_3$ is

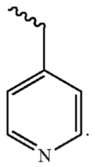

In still further embodiments $R_3$ is

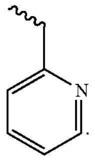

In particular embodiments $R_3$ is

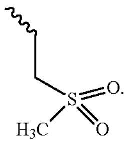

In certain embodiments $R_3$ is

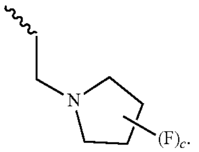

In further embodiments $R_3$ is

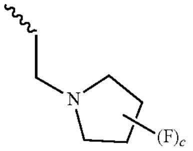

and c=1. In still further embodiments $R_3$ is

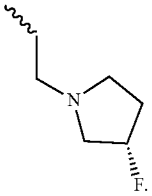

In particular embodiments $R_3$ is

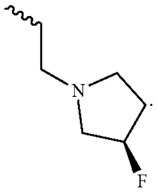

In other embodiments $R_3$ is

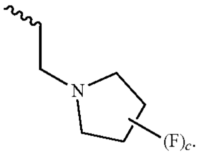

and c=2. In yet other embodiments $R_3$ is

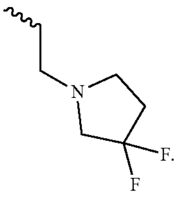

In certain embodiments $R_3$ is
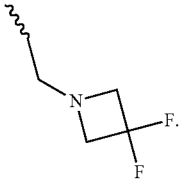
In other embodiments $R_3$ is
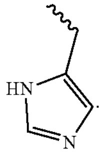
In yet other embodiments $R_3$ is
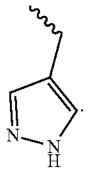
In certain embodiments the compound of Formula VI has the structure:
VIa
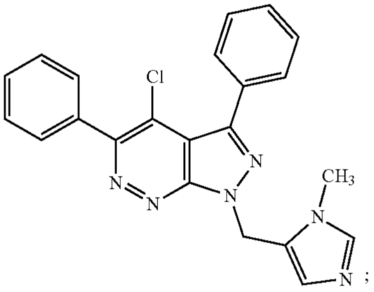
VIb
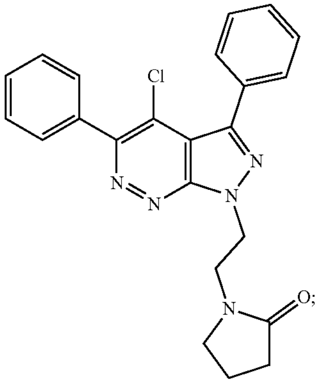
-continued
VIc
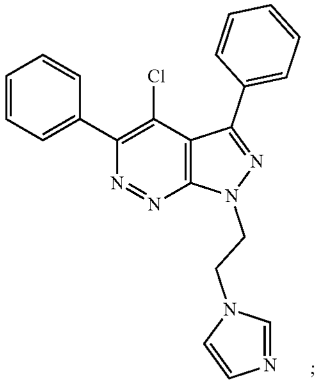
VId
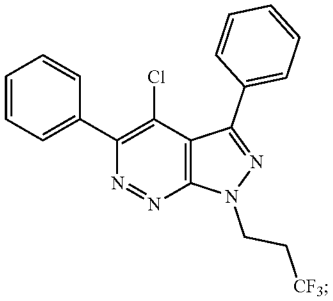
VIe
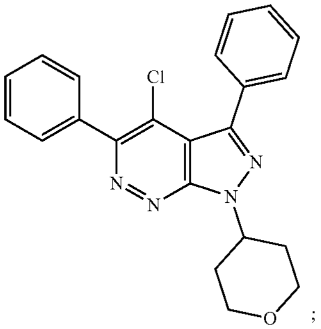
VIf
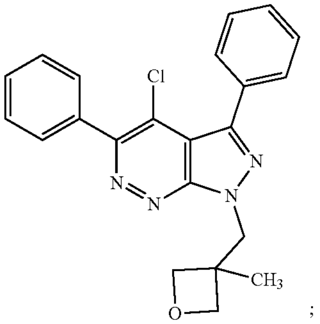

-continued
VIg
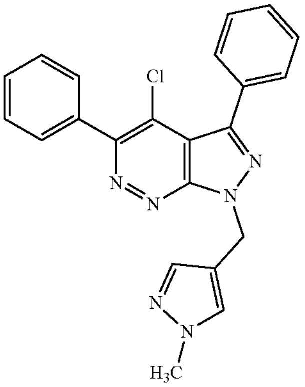
;
VIh
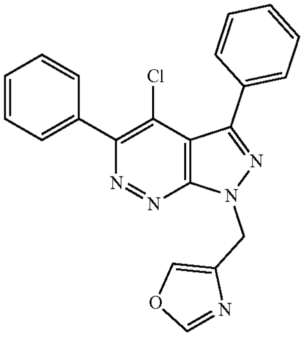
;
VIi
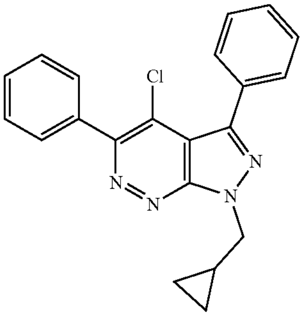
;
VIj
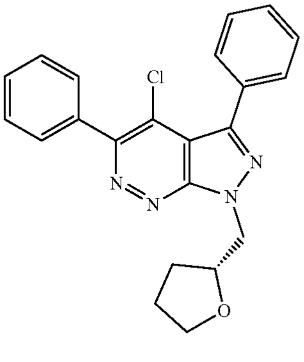
;
-continued
VIk
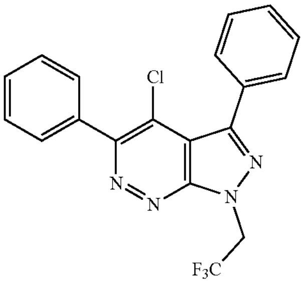
;
VIl
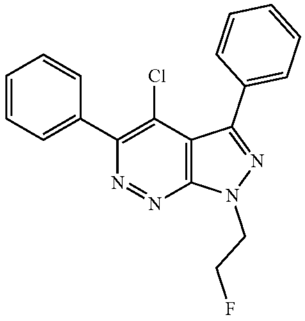
;
VIm
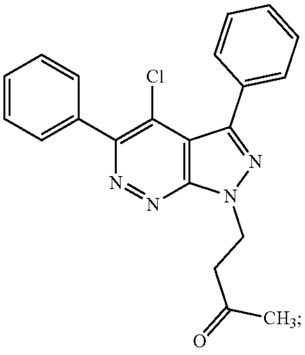
VIn
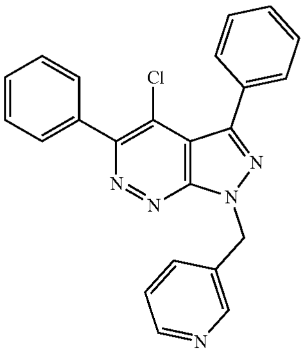
;

-continued
VIo
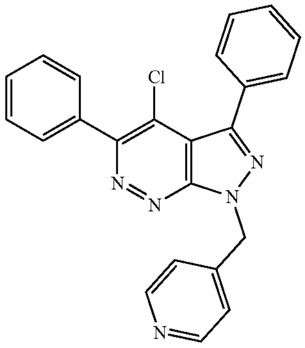
;
VIp
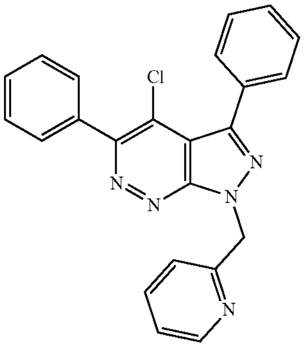
;
VIq
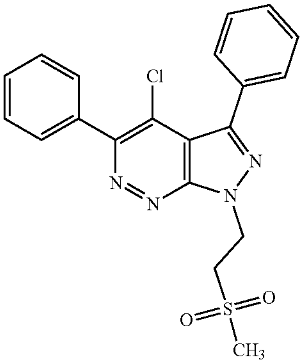
;
VIr
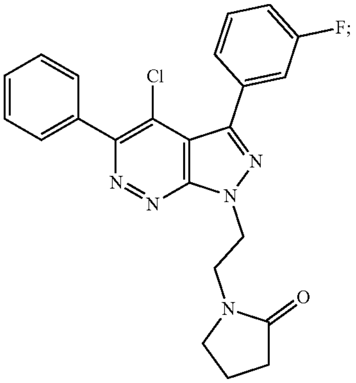
-continued
VIs
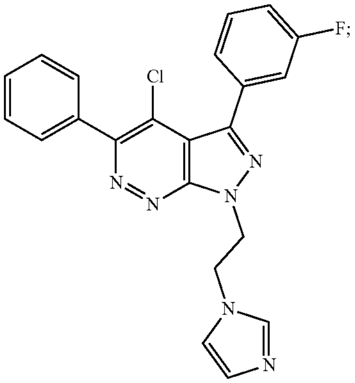
VIt
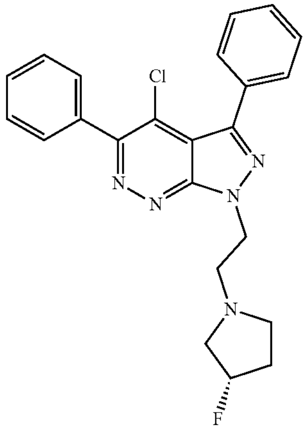
;
VIu
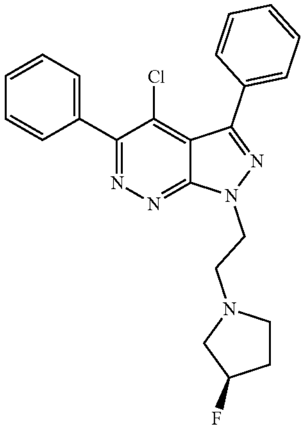
;

-continued

VIv

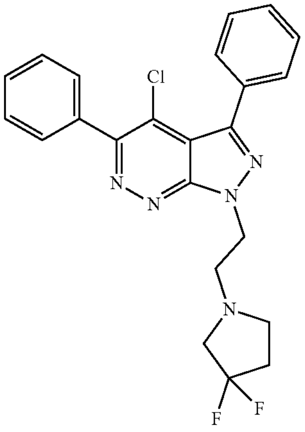

;

VIw

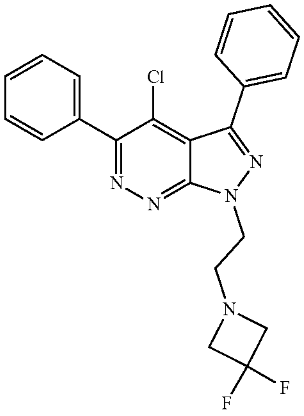

;

VIx

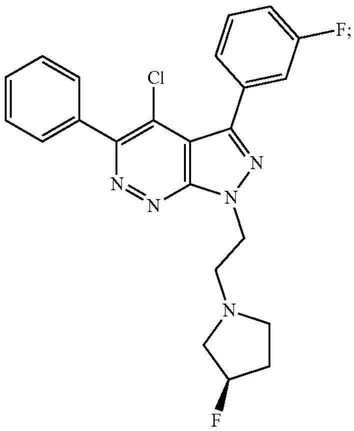

; or

-continued

VIy

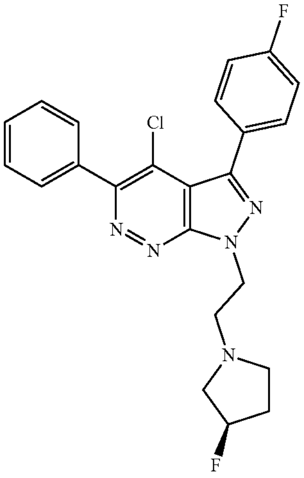

;

or a pharmaceutically acceptable salt thereof.

Compounds of Formula VII

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula VII:

Formula VII

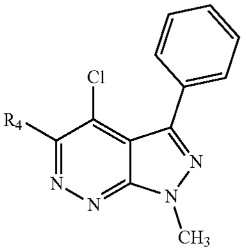

or a pharmaceutically acceptable salt thereof, wherein $R_4$ is —I;

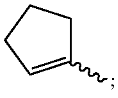 ; 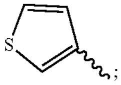 ; or 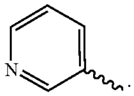 .

In certain embodiments $R_4$ is —I (iodo). In particular embodiments $R_4$ is

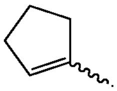 .

In other embodiments $R_4$ is

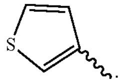

In yet other embodiments $R_4$ is

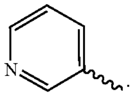

In certain embodiments the compound of Formula VII has the structure:

VIIa

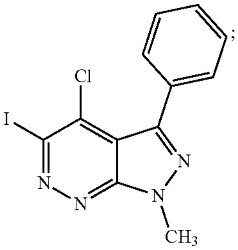

VIIb

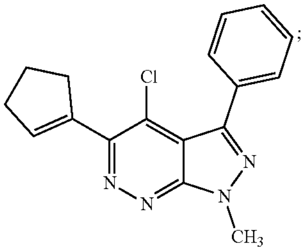

VIIc

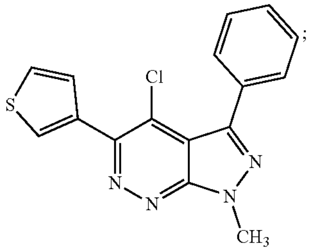

or

VIId

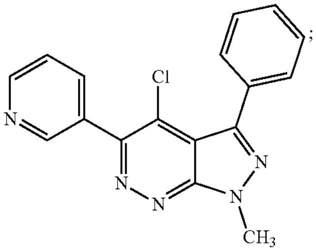

or a pharmaceutically acceptable salt thereof.

Compounds of Formula XIII

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula XIII:

Formula XIII

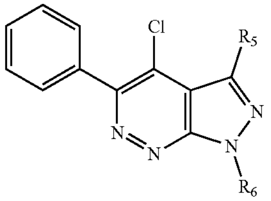

or a pharmaceutically acceptable salt thereof, wherein $R_5$ is:

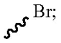
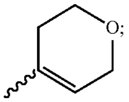
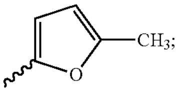
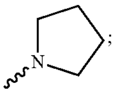
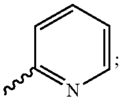
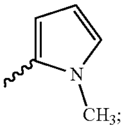
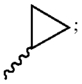
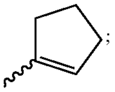
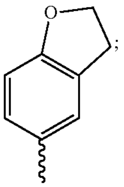
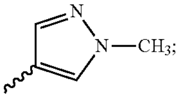
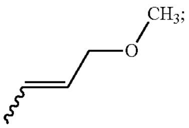
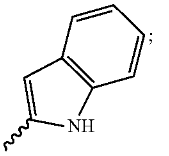
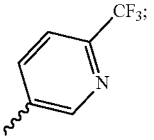
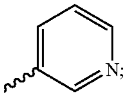
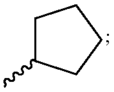
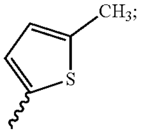
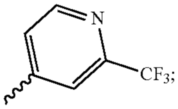
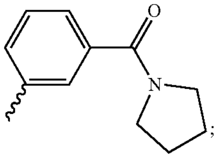
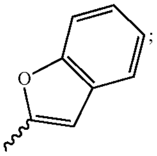

-continued
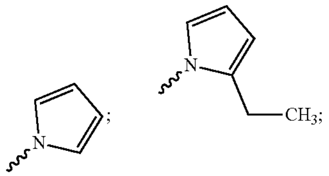
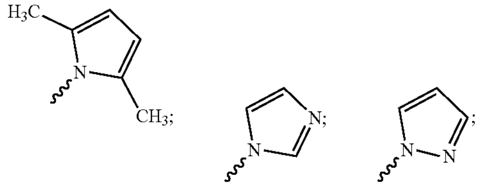
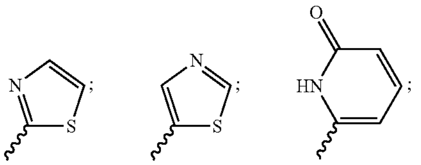
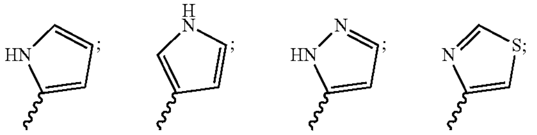
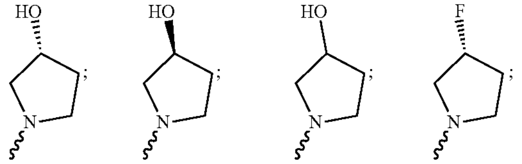
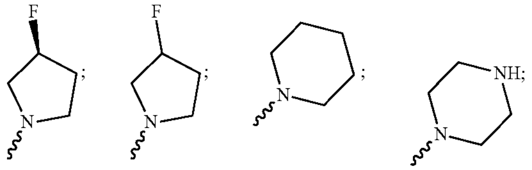
or
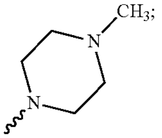
$R_6$ is:
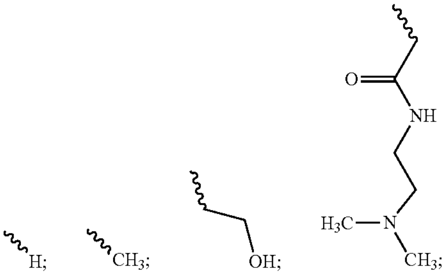
-continued
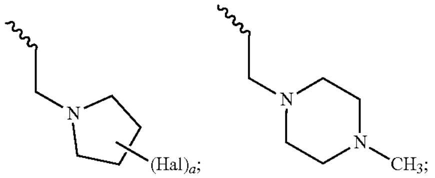
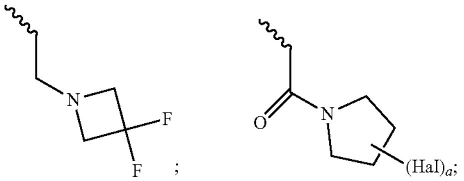
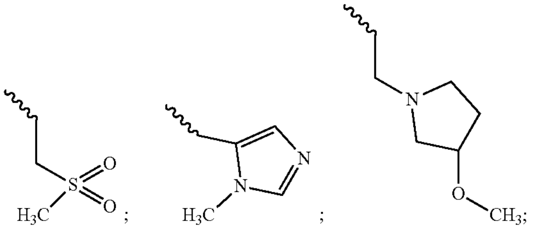
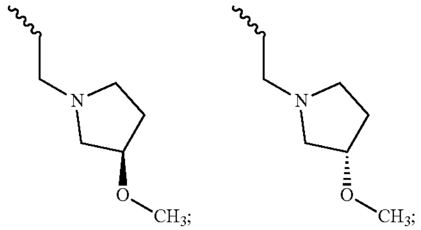
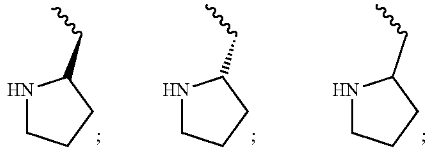
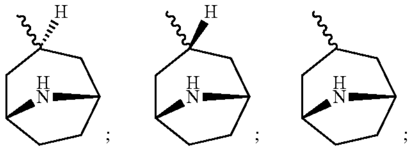
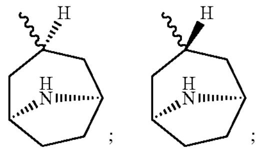
or
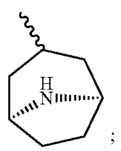
Hal is —Cl, —F, —I, or —Br; and
a is 0, 1, or 2.
In particular embodiments, $R_5$ is —I. In other embodiments, $R_5$ is —H. In yet other embodiments, $R_5$ is —$CH_3$. In certain embodiments, $R_5$ is —$CF_3$.
In yet other embodiments, $R_5$ is
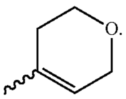

In certain embodiments, $R_5$ is

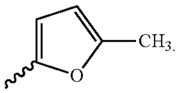

In still further embodiments, $R_5$ is

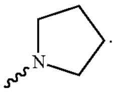

In particular embodiments, $R_5$ is

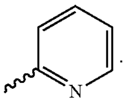

In other embodiments, $R_5$ is

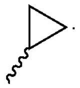

In yet other embodiments, $R_5$ is

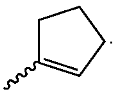

In certain embodiments, $R_5$ is

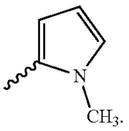

In particular embodiments, $R_5$ is

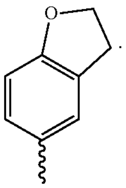

In certain embodiments, $R_5$ is

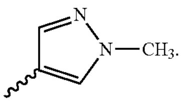

In still further embodiments, $R_5$ is

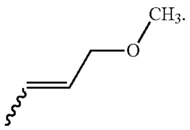

In other embodiments, $R_5$ is

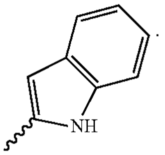

In yet other embodiments, $R_5$ is

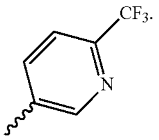

In certain embodiments, $R_5$ is

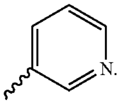

In still further embodiments, $R_5$ is

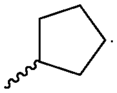

In other embodiments, $R_5$ is

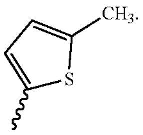

In particular embodiments, $R_5$ is

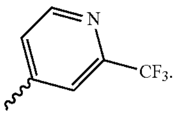

In further embodiments, $R_5$ is

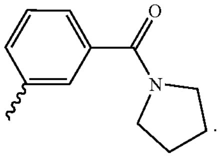

In still further embodiments, $R_5$ is

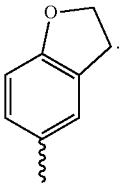

In certain embodiments, $R_5$ is

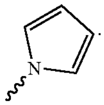

In further embodiments, $R_5$ is

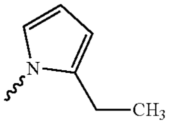

In further embodiments, $R_5$ is

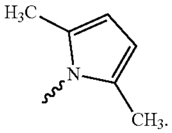

In other embodiments, $R_5$ is

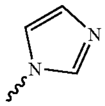

In yet other embodiments, $R_5$ is

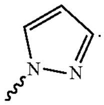

In particular embodiments, $R_5$ is

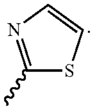

In further embodiments, $R_5$ is

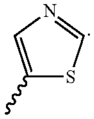

In still further embodiments, $R_5$ is

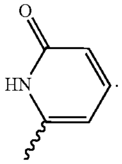

In certain embodiments, $R_5$ is

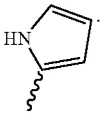

In other embodiments, $R_5$ is

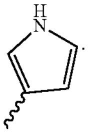

In yet other embodiments, $R_5$ is

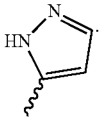

In particular embodiments, $R_5$ is

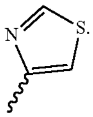

In further embodiments, $R_5$ is

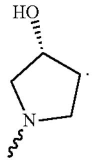

In still further embodiments, $R_5$ is

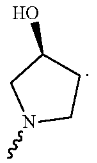

In certain embodiments, $R_5$ is

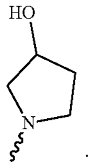

In other embodiments, $R_5$ is

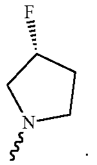

In yet other embodiments, $R_5$ is

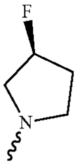

In particular embodiments, $R_5$ is

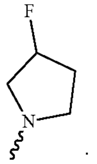

In further embodiments, $R_5$ is

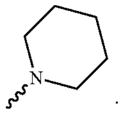

In still further embodiments, $R_5$ is

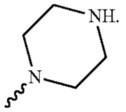

In certain embodiments, $R_5$ is

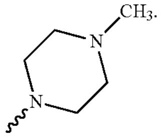

In certain embodiments, $R_6$ is

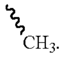

In further embodiments, $R_6$ is

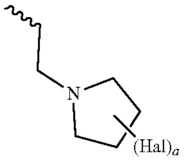

and a=0. In other embodiments, the compound of Formula XIII is a pharmaceutically acceptable salt and $R_6$ is

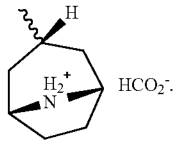

In yet other embodiments, the compound of Formula XIII is a pharmaceutically acceptable salt and $R_6$ is

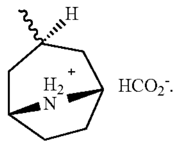

In particular embodiments, the compound of Formula XIII is a pharmaceutically acceptable salt and $R_6$ is

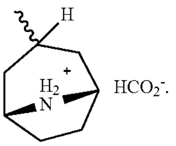

In certain embodiments, the compound of Formula XIII is a pharmaceutically acceptable salt and $R_6$ is

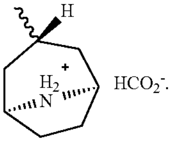

In further embodiments, the compound of Formula XIII is a pharmaceutically acceptable salt and $R_6$ is

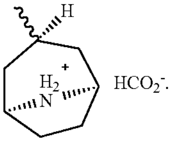

In other embodiments, the compound of Formula XIII s a pharmaceutically acceptable salt and $R_6$ is

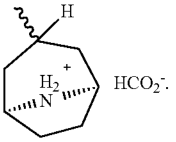

In certain embodiments, $R_6$ is

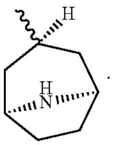

In further embodiments, $R_6$ is

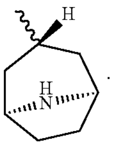

In particular embodiments, $R_6$ is

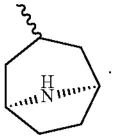

In further embodiments, $R_6$ is

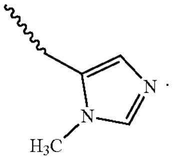

In still further embodiments, $R_6$ is

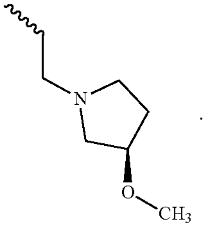

In other embodiments, $R_6$ is

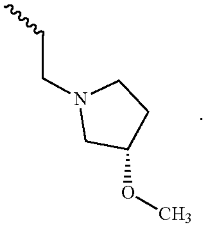

In certain embodiments, $R_6$ is

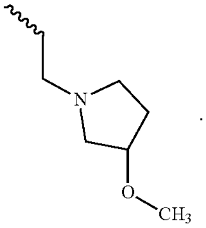

In yet other embodiments, $R_6$ is
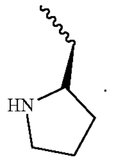
In particular embodiments, $R_6$ is
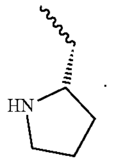
In further embodiments, $R_6$ is
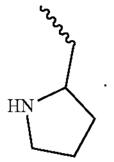
In still further embodiments, $R_6$ is
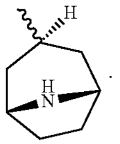
In certain embodiments, $R_6$ is
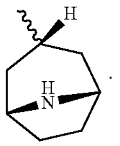
In other embodiments, $R_6$ is
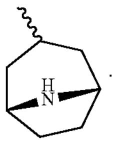
In further embodiments, when a is 2, each Hal is the same or different.
In certain embodiments the compound of Formula XIII has the structure:
XIIIb
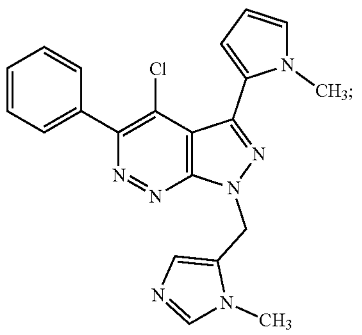
XIIIc
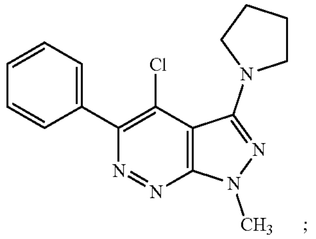
XIIId
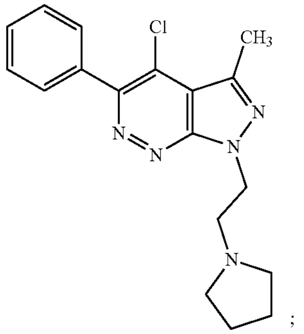
XIIIe
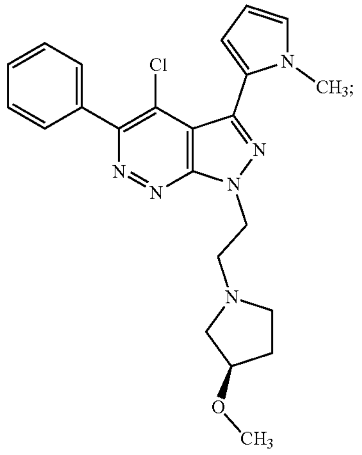

-continued
XIIIf
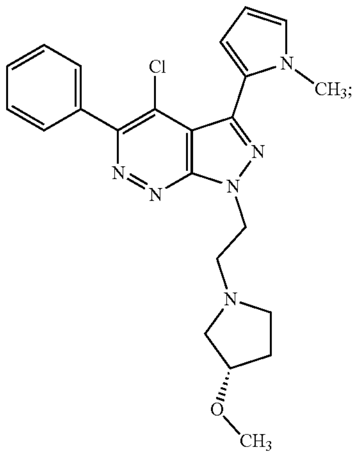
XIIIg
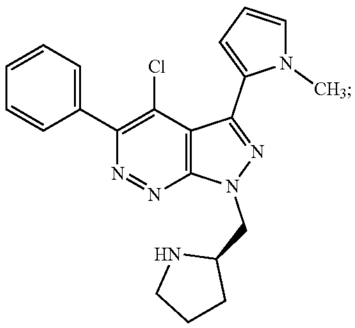
XIIIh
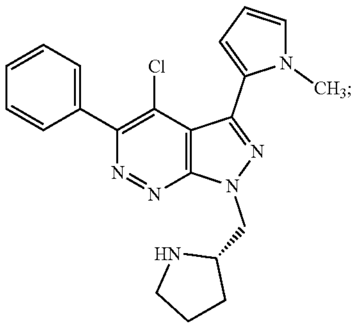
XIIIi
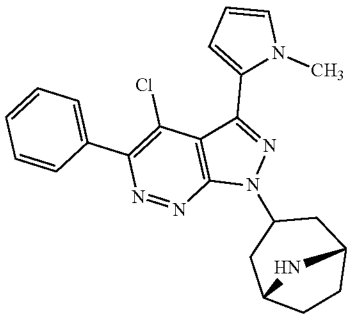
;
-continued
XIIIj
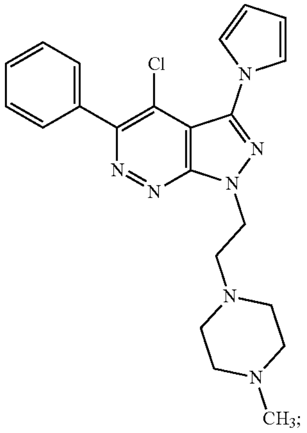
XIIIk
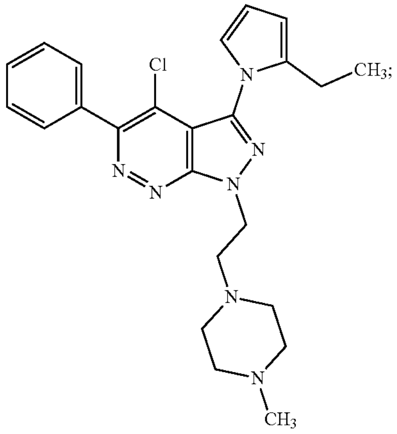
XIIIl
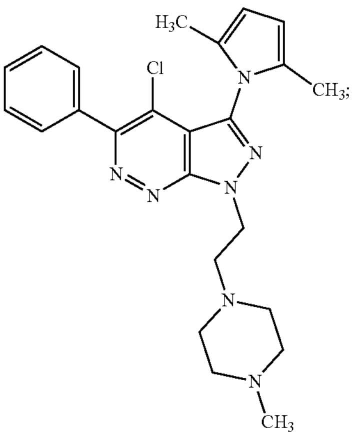

-continued
XIIIm
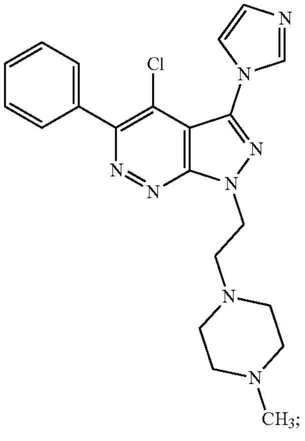
XIIIn
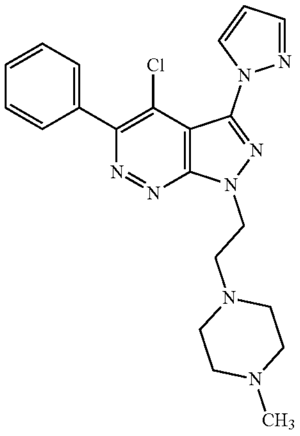
XIIIo
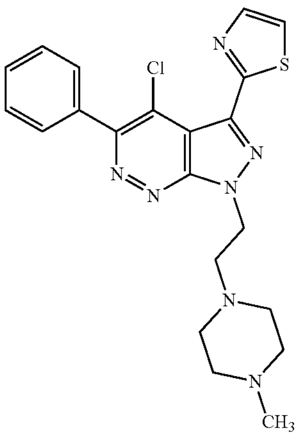
-continued
XIIIp
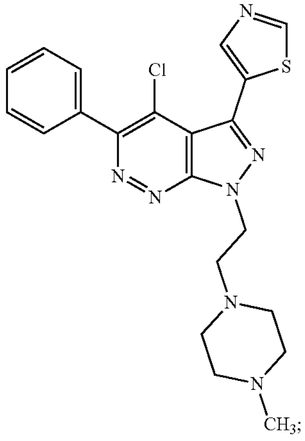
XIIIq
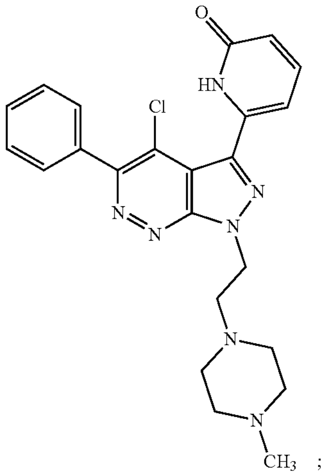
XIIIr
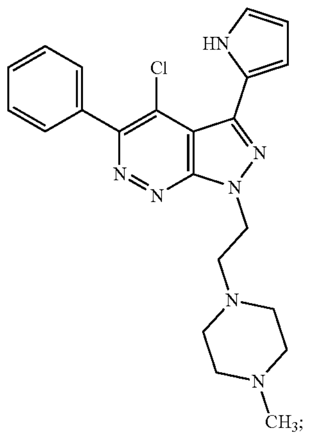

-continued
XIIIs
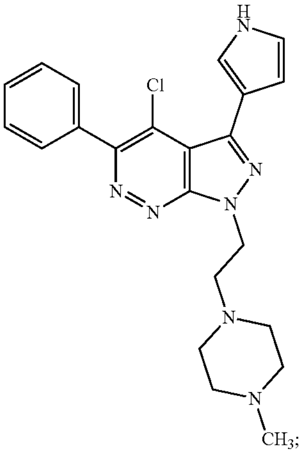
XIIIt
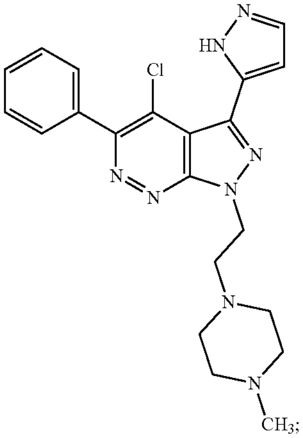
XIIIu
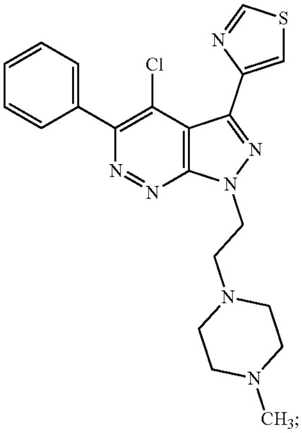
-continued
XIIIv
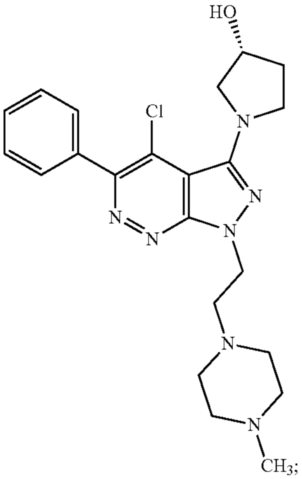
XIIIw
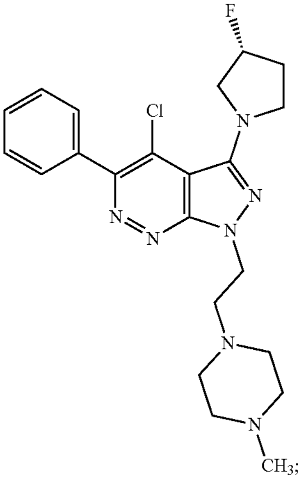
XIIIx
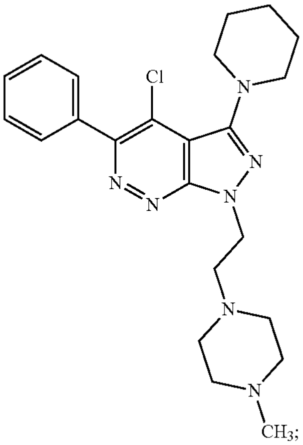

-continued

XIIIy

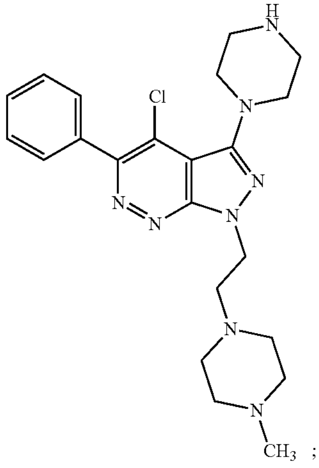

or

XIIIz

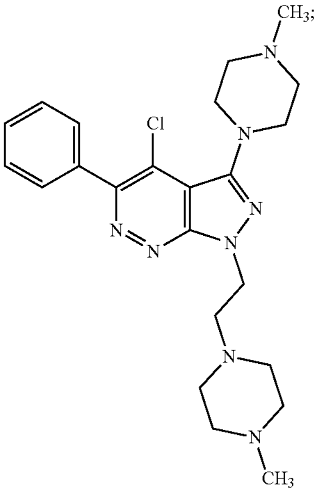

or a pharmaceutically acceptable salt thereof.

In other embodiments, the compound of Formula XIII is a pharmaceutically acceptable salt and has the structure:

XIIIa

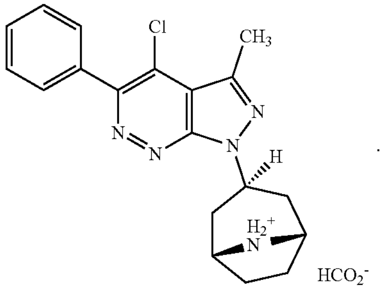

Compounds of Formula XIV

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula XIV:

Formula XIV

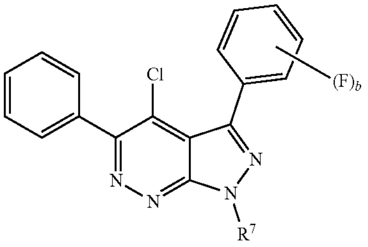

or a pharmaceutically acceptable salt thereof, wherein $R_7$ is:

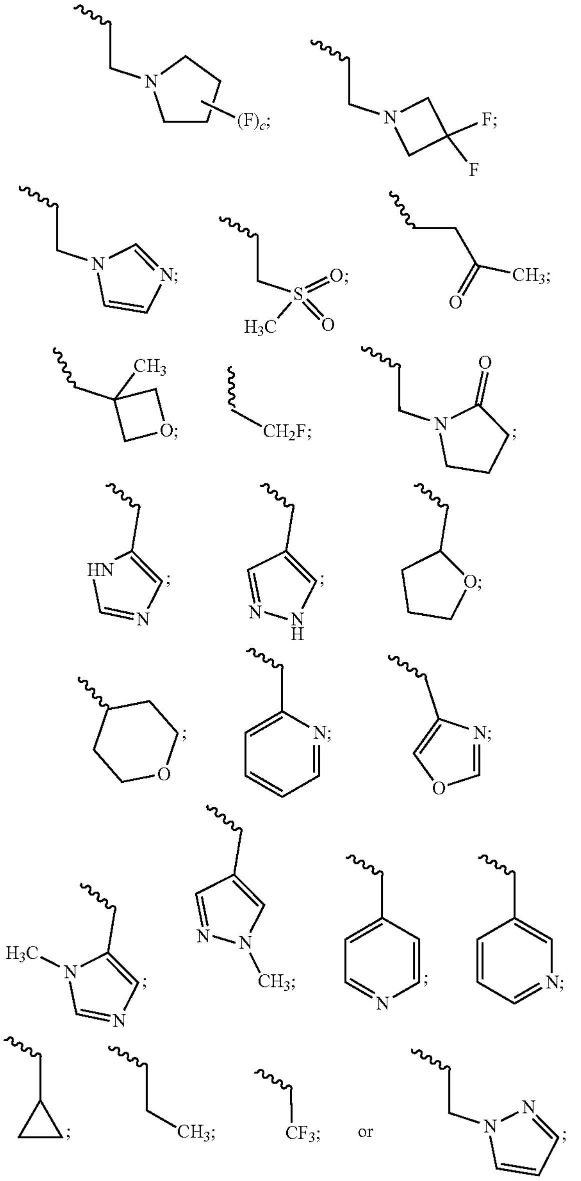

or b is 0 or 1; and c is 1 or 2.

In particular embodiments, b is 0. In other embodiments b is 1 and the —F is in the meta position relative to the pyrazolopyridazino ring system. In yet other embodiments b is 1 and the —F is in the para position relative to the pyrazolopyridazino ring system.

In particular embodiments $R_7$ is $—CF_3$. In certain embodiments $R_7$ is

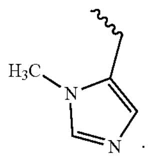

In other embodiments $R_7$ is

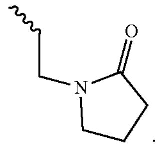

In yet other embodiments $R_7$ is

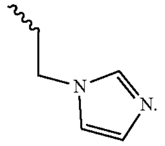

In further embodiments $R_7$ is

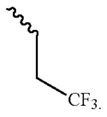

In still further embodiments $R_7$ is

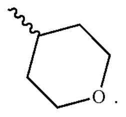

In particular embodiments $R_7$ is

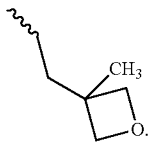

In other embodiments $R_7$ is

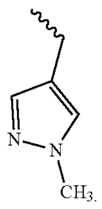

In yet other embodiments $R_7$ is

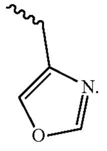

In certain embodiments $R_7$ is

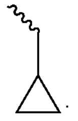

In further embodiments $R_7$ is

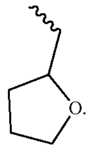

In further embodiments $R_7$ is

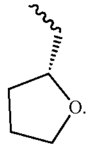

In certain embodiments $R_7$ is

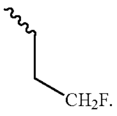

In other embodiments $R_7$ is

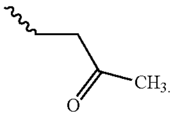

In yet other embodiments $R_7$ is

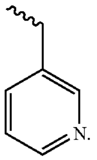

In further embodiments $R_7$ is

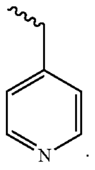

In still further embodiments $R_7$ is

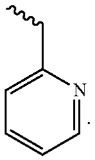

In particular embodiments $R_7$ is

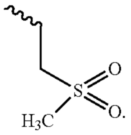

in certain embodiments $R_7$ is

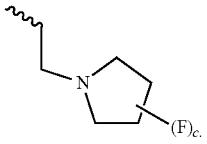

In further embodiments $R_7$ is

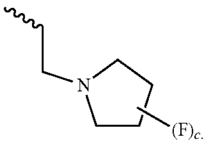

and c=1. In still further embodiments $R_7$ is

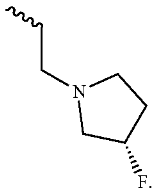

In particular embodiments $R_7$ is

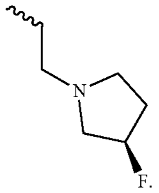

In other embodiments $R_7$ is

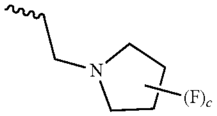

and c=2. In yet other embodiments $R_7$ is

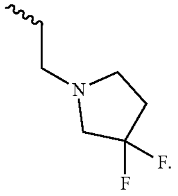

In certain embodiments $R_7$ is

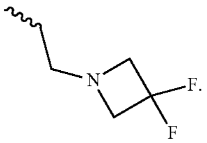

In other embodiments $R_7$ is

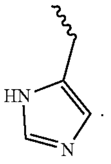

In yet other embodiments $R_7$ is

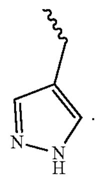

In yet other embodiments $R_7$ is

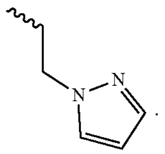

In certain embodiments the compound of Formula XIV has the structure:

XIVa

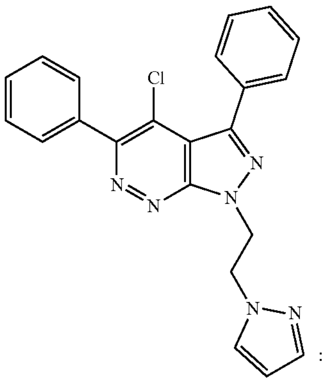

or a pharmaceutically acceptable salt thereof.

Compounds of Formula XV

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound of Formula XV:

Fomula XV

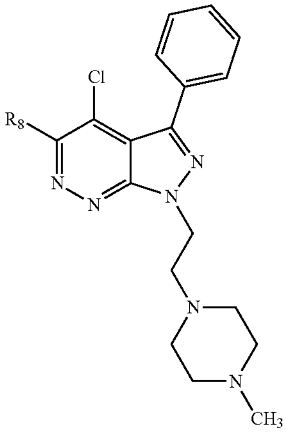

or a pharmaceutically acceptable salt thereof, wherein $R_8$ is:

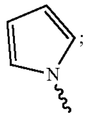 ; 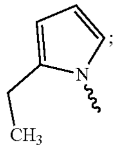 ; 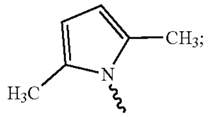 ;

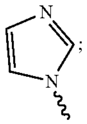 ; 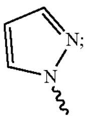 ; 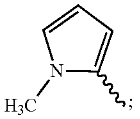 ; 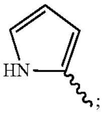 ;

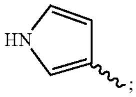 ; 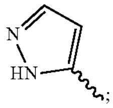 ; 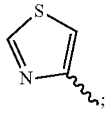 ;

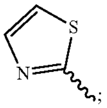 ; 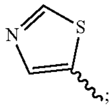 ; or 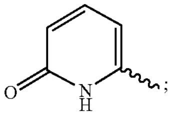 ;

In particular embodiments $R_8$ is

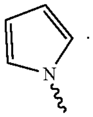

In certain embodiments $R_8$ is

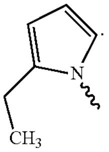

In other embodiments $R_8$ is

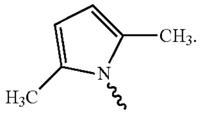

In yet other embodiments $R_8$ is

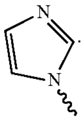

In further embodiments $R_8$ is

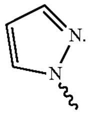

In still further embodiments $R_8$ is

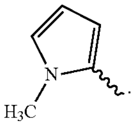

In particular embodiments $R_8$ is

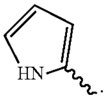

In particular embodiments $R_8$ is

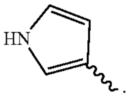

In certain embodiments $R_8$ is

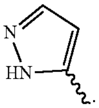

In other embodiments $R_8$ is

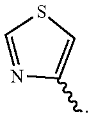

In yet other embodiments $R_8$ is

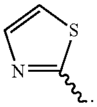

In further embodiments $R_8$ is

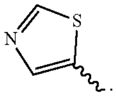

In still further embodiments $R_8$ is

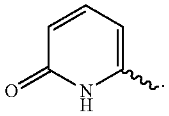

In certain embodiments the compound of Formula XV has the structure:

XVa

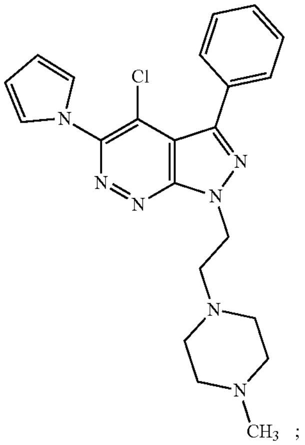

-continued
XVb
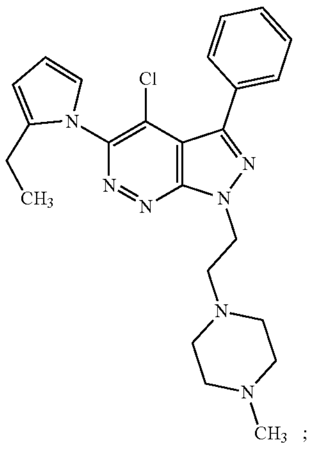
XVc
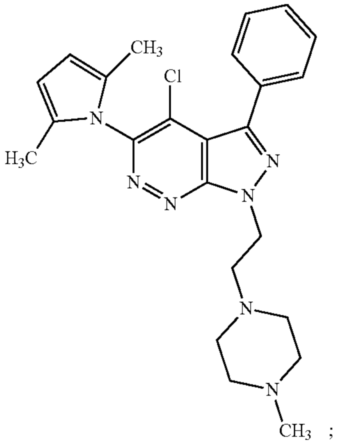
XVd
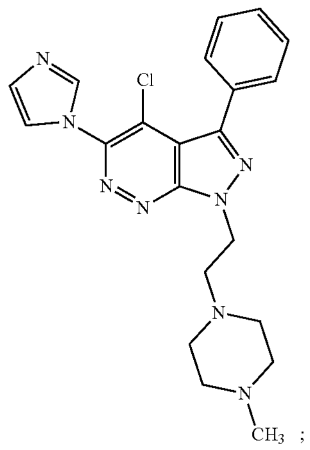
XVe
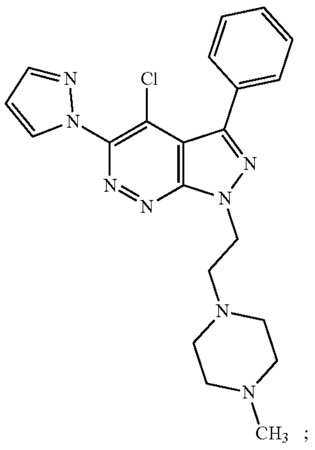
XVf
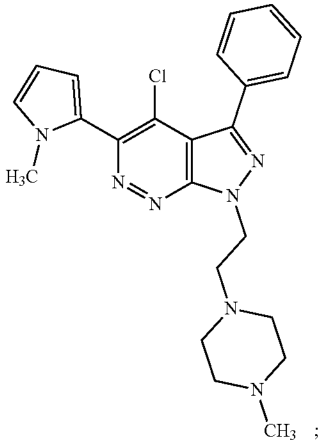
XVg
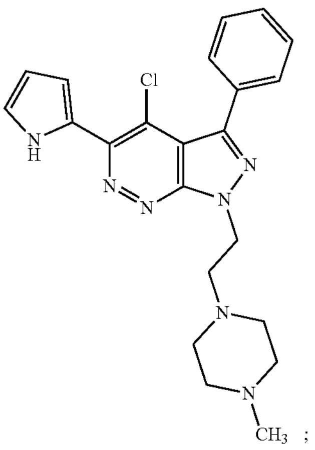

-continued

XVh

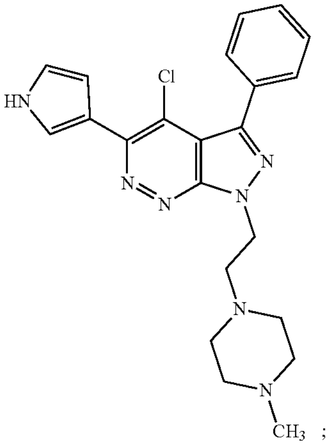

XVi

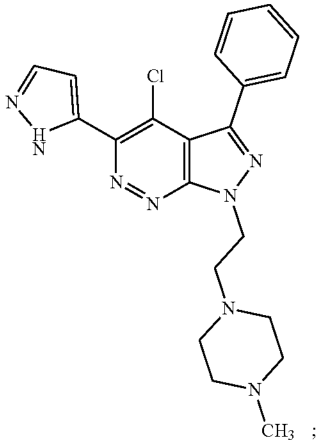

XVi

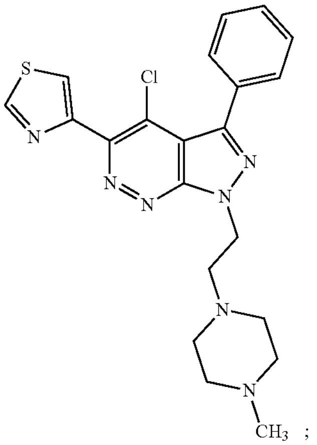

-continued

XVk

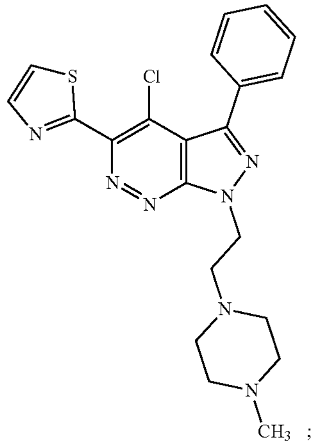

XVl

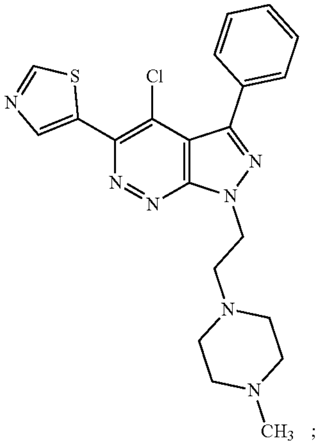

or

XVm

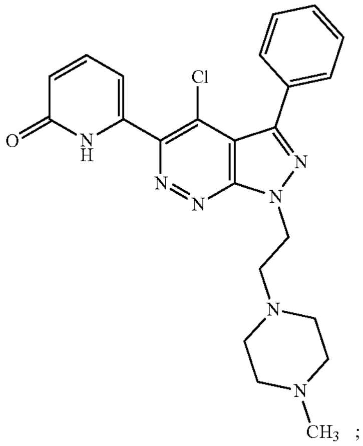

or a pharmaceutically acceptable salt thereof

Other Compounds

In one embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a compound having the structure:

-continued
44
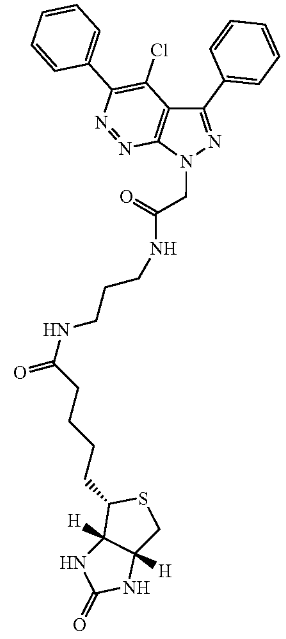
;
46
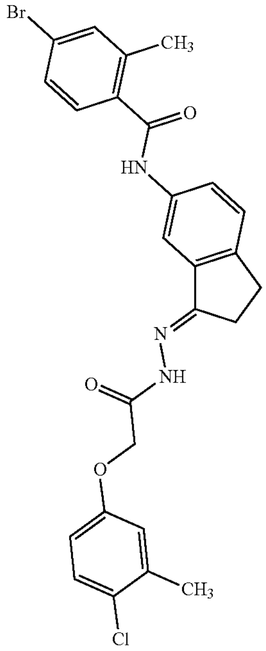
;
112
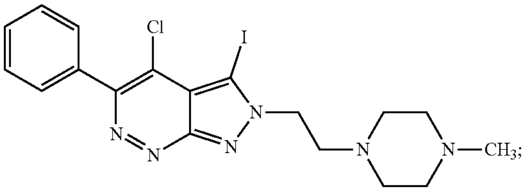
113
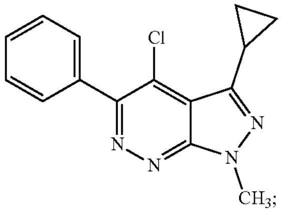
114
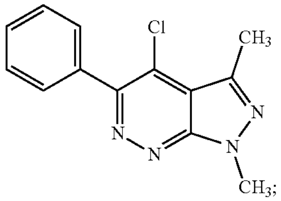
115
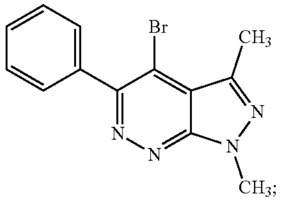
116
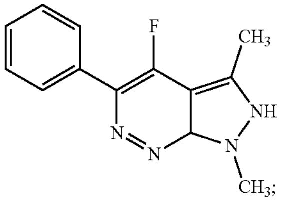
117
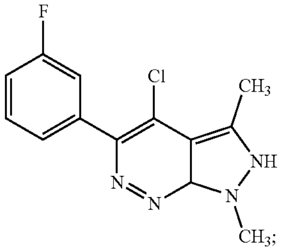
118
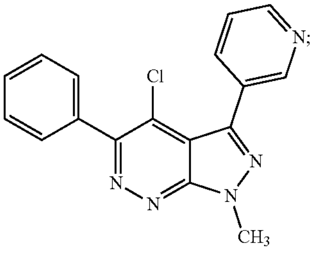
119
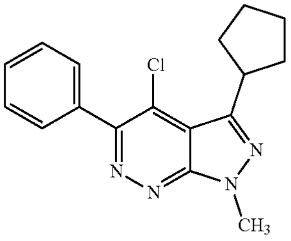
;

-continued

120

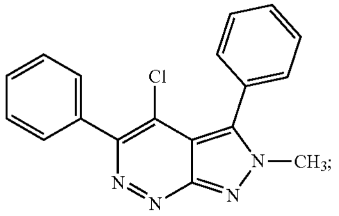

121

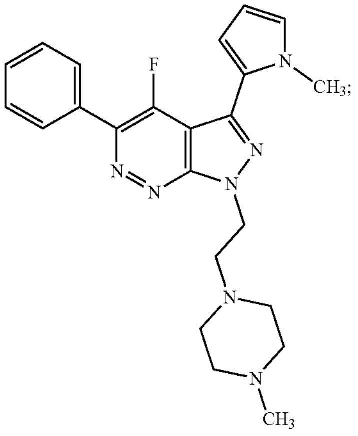

122

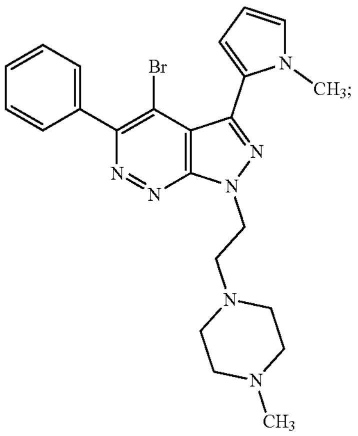

123

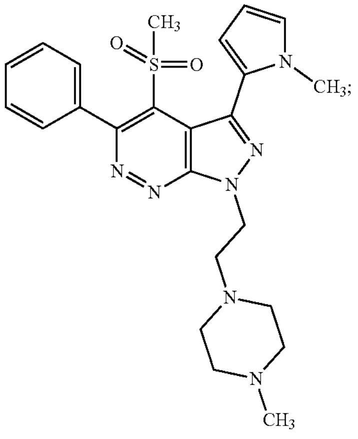

-continued

124a

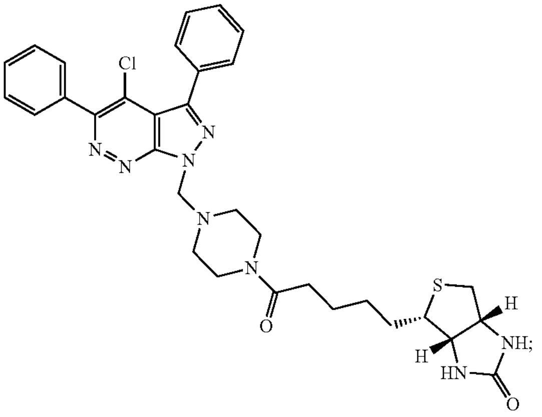

or

124b

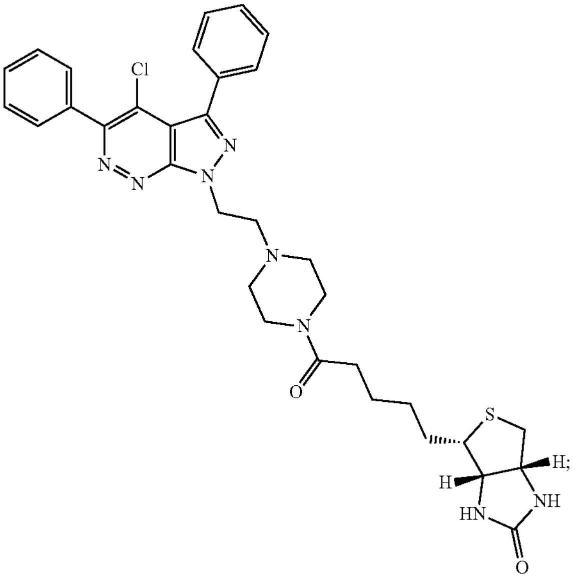

or a pharmaceutically acceptable salt thereof.

Non-Pyrazolopyridazine Compounds

A compound or a pharmaceutically acceptable salt of the compound of Table below is a non-pyrazolopyridazine compound.

In one embodiment, the invention provides non-pyrazolopyridazine compounds. In a further embodiment, the invention provides methods for treating or preventing cancer, an inflammatory disease or an autoimmune disease, or for reducing risk of developing cancer, an inflammatory disease or an autoimmune disease, comprising administering to a subject in need thereof an effective amount of a non-Pyrazolopyridazine compound or a pharmaceutically acceptable salt thereof; and a pharmaceutically acceptable carrier or vehicle.

TABLE 1
| Non-Pyrazolopyridazine compounds of the invention | |
|---|---|
| Compound No. | Structure |
| 125 | 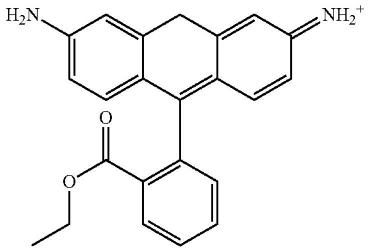 |
| 126 | 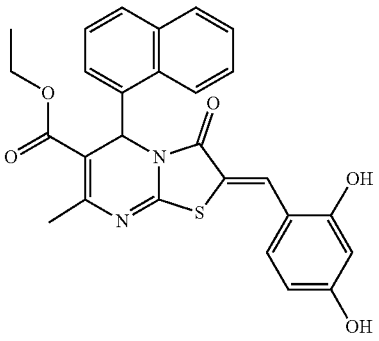 [SMILES: CCOC(=O)C1=C(C)N=c2s/c(=C\c3ccc(O)cc3O)c(=O)n2C1c1cccc2ccccc12] |
| 127 | 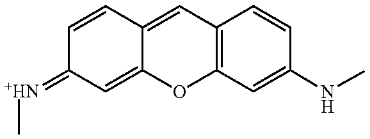 |
| 128 | 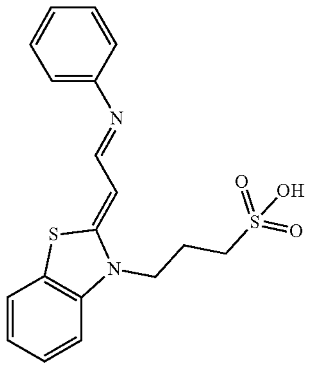 [SMILES: O=S(=O)(O)CCCN1/C(=C/C=N/c2ccccc2)Sc2ccccc21] |
| 129 | 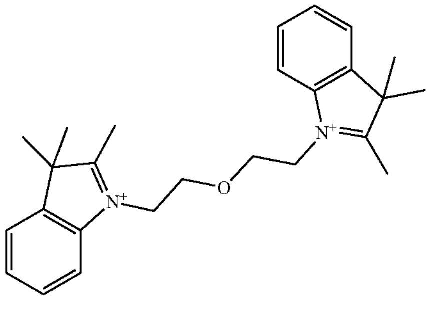 [SMILES: CC1=[N+](CCOCC[N+]2=C(C)C(C)(C)c3ccccc32)c2ccccc2C1(C)C] |
TABLE 1-continued
| Non-Pyrazolopyridazine compounds of the invention | |
|---|---|
| Compound No. | Structure |
| 130 | 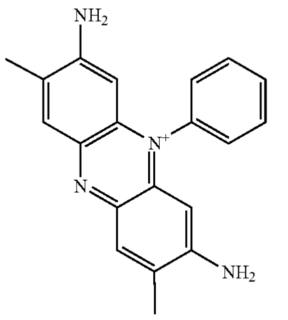 [SMILES: Cc1cc2nc3cc(C)c(N)cc3[n+](-c3ccccc3)c2cc1N] |
| 131 | 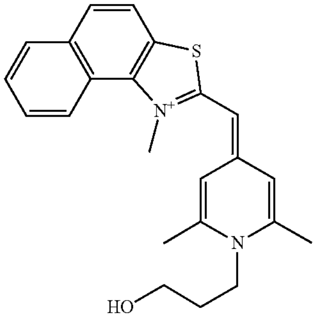 [SMILES: CC1=CC(=Cc2sc3ccc4ccccc4c3[n+]2C)C=C(C)N1CCCO] |
| 132 | 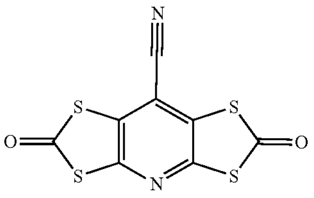 [SMILES: N#Cc1c2sc(=O)sc2nc2sc(=O)sc12] |
| 133 | 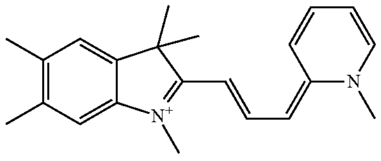 |
| 134 | 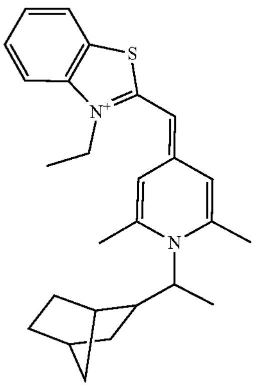 [SMILES: CC[n+]1c(C=C2C=C(C)N(C(C)C3CC4CCC3C4)C(C)=C2)sc2ccccc21] |

TABLE 1-continued
Non-Pyrazolopyridazine compounds of the invention
| Compound No. | Structure |
|---|---|
| 135 | 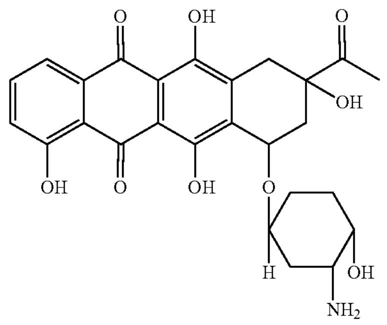 [SMILES: CC(=O)C1(O)Cc2c(O)c3c(c(O)c2C(OC2CCC(O)C(N)C2)C1)C(=O)c1c(O)cccc1C3=O] |
| 136 | 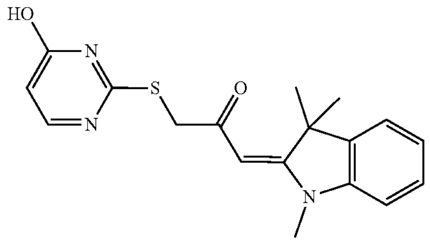 [SMILES: CN1/C(=C/C(=O)CSc2nccc(O)n2)C(C)(C)c2ccccc21] |
| 137 | 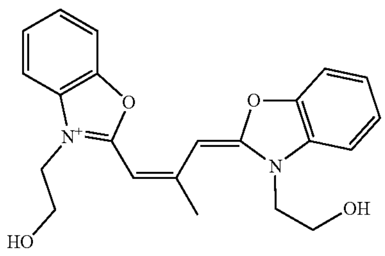 [SMILES: CC(=C/c1oc2ccccc2[n+]1CCO)/C=C1/Oc2ccccc2N1CCO] |
| 138 | 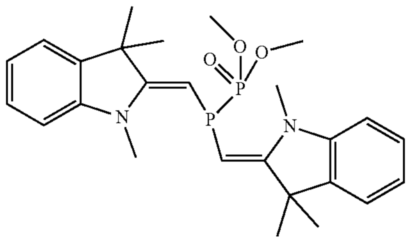 [SMILES: COP(=O)(OC)P(/C=C1\N(C)c2ccccc2C1(C)C)/C=C1\N(C)c2ccccc2C1(C)C] |
| 139 | 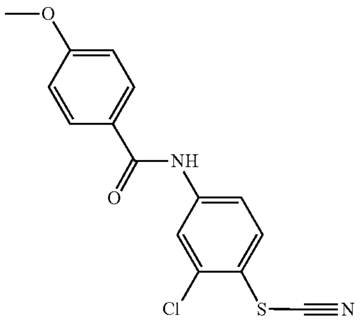 [SMILES: COc1ccc(C(=O)Nc2ccc(SC#N)c(Cl)c2)cc1] |
TABLE 1-continued
Non-Pyrazolopyridazine compounds of the invention
| Compound No. | Structure |
|---|---|
| 140 | 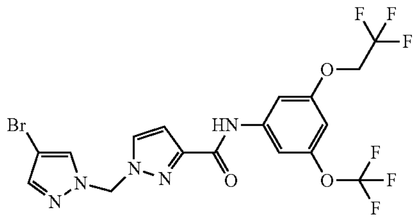 [SMILES: O=C(Nc1cc(OCC(F)(F)F)cc(OC(F)(F)F)c1)c1ccn(Cn2cc(Br)cn2)n1] |
| 141 | 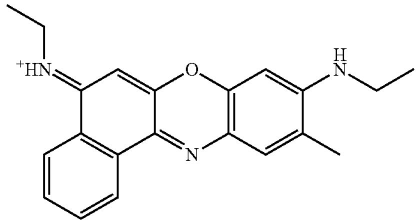 [SMILES: CCNc1cc2oc3c/c(=[NH+]\CC)c4ccccc4c-3nc2cc1C] |
| 142 | 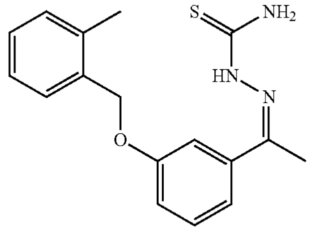 [SMILES: C/C(=N/NC(N)=S)c1cccc(OCc2ccccc2C)c1] |
| 143 | 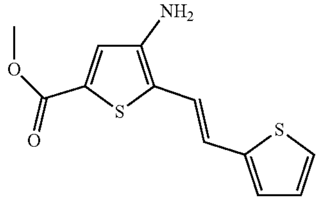 [SMILES: COC(=O)c1cc(N)c(/C=C/c2cccs2)s1] |
| 144 | 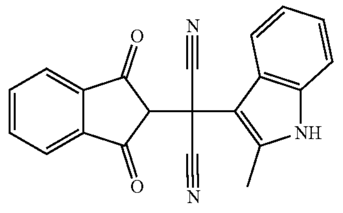 [SMILES: Cc1[nH]c2ccccc2c1C(C#N)(C#N)C1C(=O)c2ccccc2C1=O] |
| 145 | 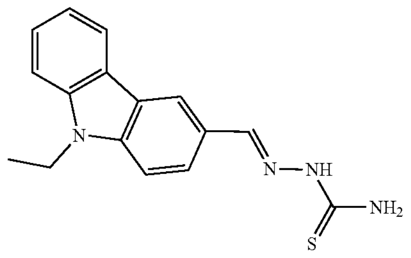 [SMILES: CCn1c2ccccc2c2cc(/C=N/NC(N)=S)ccc21] |

TABLE 1-continued
Non-Pyrazolopyridazine compounds of the invention
| Compound No. | Structure |
|---|---|
| 146 | 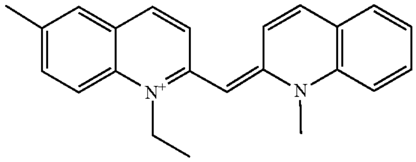 [SMILES: CC[n+]1c(/C=C2\C=Cc3ccccc3N2C)ccc2cc(C)ccc21] |
| 147 | 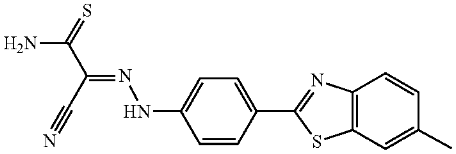 [SMILES: Cc1ccc2nc(-c3ccc(N/N=C(\C#N)C(N)=S)cc3)sc2c1] |
| 148 | 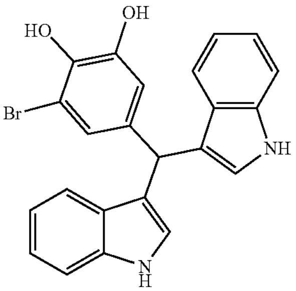 [SMILES: Oc1cc(C(c2c[nH]c3ccccc23)c2c[nH]c3ccccc23)cc(Br)c1O] |
| 149 | 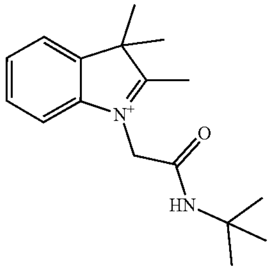 [SMILES: CC1=[N+](CC(=O)NC(C)(C)C)c2ccccc2C1(C)C] |
| 150 | 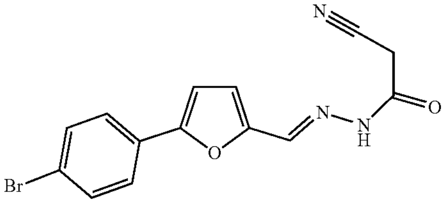 [SMILES: N#CCC(=O)N/N=C/c1ccc(-c2ccc(Br)cc2)o1] |
| 151 | 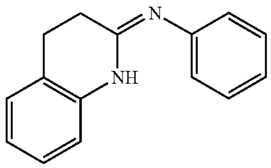 [SMILES: c1ccc(/N=C2/CCc3ccccc3N2)cc1] |
TABLE 1-continued
Non-Pyrazolopyridazine compounds of the invention
| Compound No. | Structure |
|---|---|
| 152 | 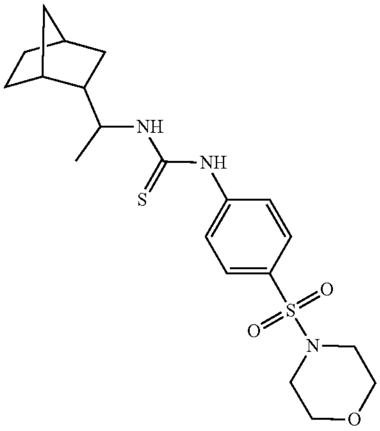 [SMILES: CC(NC(=S)Nc1ccc(S(=O)(=O)N2CCOCC2)cc1)C1CC2CCC1C2] |
| 153 | 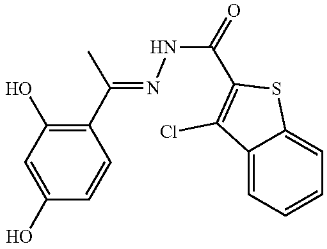 [SMILES: C/C(=N\NC(=O)c1sc2ccccc2c1Cl)c1ccc(O)cc1O] |
| 154 | 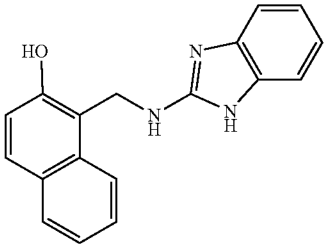 [SMILES: Oc1ccc2ccccc2c1CNc1nc2ccccc2[nH]1] |
| 155 | 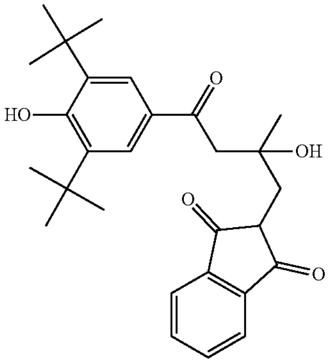 [SMILES: CC(O)(CC(=O)c1cc(C(C)(C)C)c(O)c(C(C)(C)C)c1)CC1C(=O)c2ccccc2C1=O] |

TABLE 1-continued
Non-Pyrazolopyridazine compounds of the invention
| Compound No. | Structure |
|---|---|
| 156 | 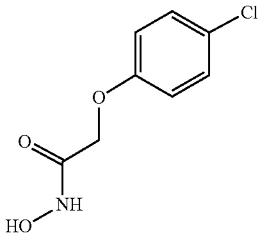 [SMILES: O=C(COc1ccc(Cl)cc1)NO] |
| 157 | 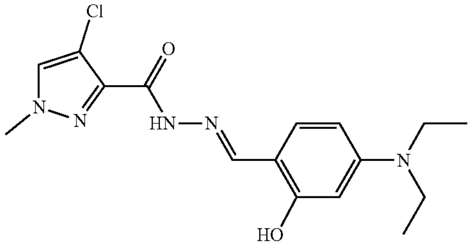 [SMILES: CCN(CC)c1ccc(/C=N/NC(=O)c2nn(C)cc2Cl)c(O)c1] |
| 158 | 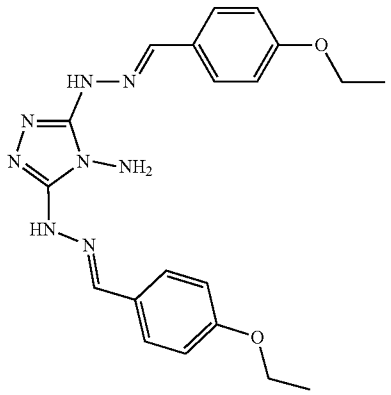 [SMILES: CCOc1ccc(/C=N/Nc2nnc(N/N=C/c3ccc(OCC)cc3)n2N)cc1] |
| 159 | 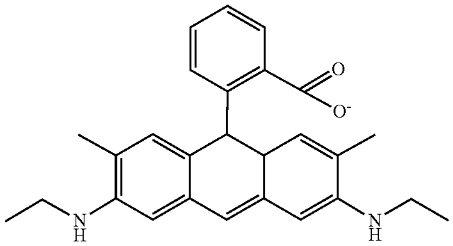 [SMILES: CCNC1=CC2=Cc3cc(NCC)c(C)cc3C(c3ccccc3C(=O)[O-])C2C=C1C] |
| 160 | 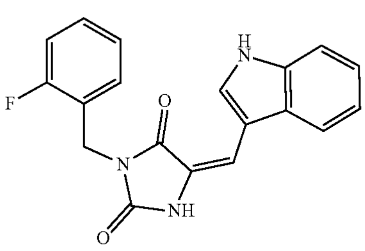 [SMILES: O=C1N/C(=C/c2c[nH]c3ccccc23)C(=O)N1Cc1ccccc1F] |
TABLE 1-continued
Non-Pyrazolopyridazine compounds of the invention
| Compound No. | Structure |
|---|---|
| 161 | 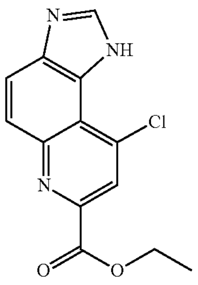 [SMILES: CCOC(=O)c1cc(Cl)c2c(ccc3nc[nH]c32)n1] |
| 162 | 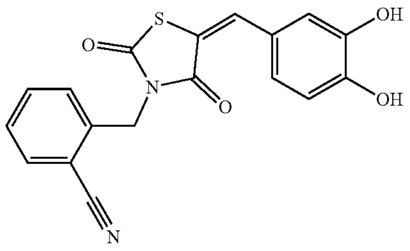 [SMILES: N#Cc1ccccc1CN1C(=O)S/C(=C/c2ccc(O)c(O)c2)C1=O] |
| 163 | 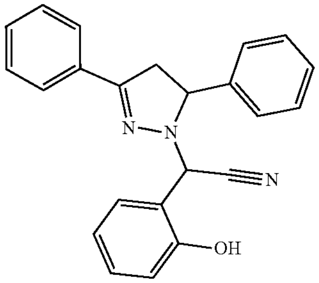 [SMILES: N#CC(c1ccccc1O)N1N=C(c2ccccc2)CC1c1ccccc1] |
| 164 | 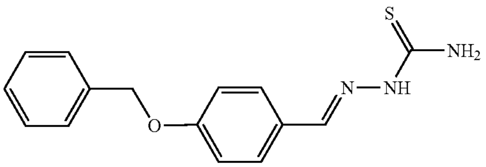 [SMILES: NC(=S)N/N=C/c1ccc(OCc2ccccc2)cc1] |
| 165 | 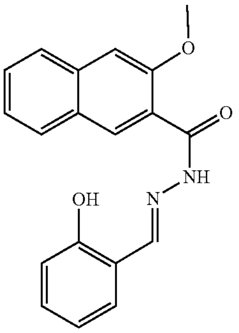 [SMILES: COc1cc2ccccc2cc1C(=O)N/N=C/c1ccccc1O] |

TABLE 1-continued
Non-Pyrazolopyridazine compounds of the invention
| Compound No. | Structure |
| --- | --- |
| 166 | 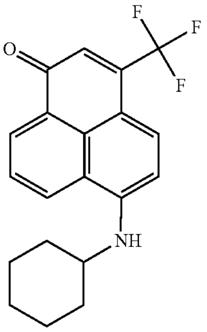 [SMILES: O=C1C=C(C(F)(F)F)c2ccc(NC3CCCCC3)c3cccc1c23] |
| 167 | 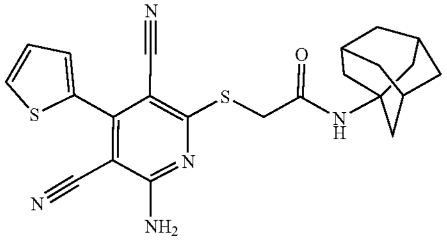 [SMILES: N#Cc1c(N)nc(SCC(=O)NC23CC4CC(CC(C4)C2)C3)c(C#N)c1-c1cccs1] |
| 168 | 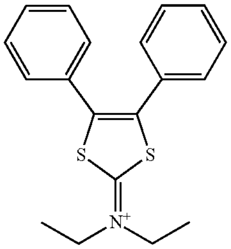 [SMILES: CC[N+](CC)=c1sc(-c2ccccc2)c(-c2ccccc2)s1] |
| 169 | 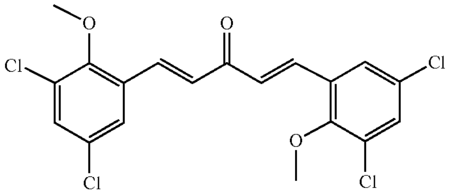 [SMILES: COc1c(Cl)cc(Cl)cc1/C=C/C(=O)/C=C/c1cc(Cl)cc(Cl)c1OC] |
| 170 | 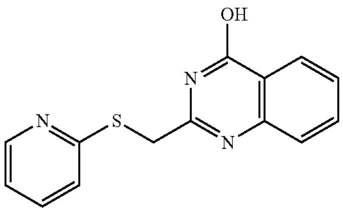 [SMILES: Oc1nc(CSc2ccccn2)nc2ccccc12] |
| 171 | 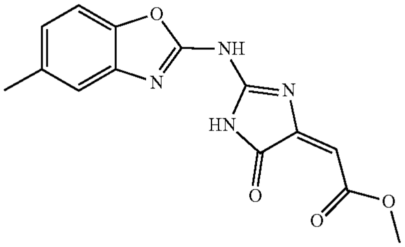 |
| 172 | 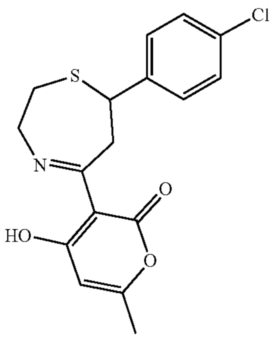 [SMILES: Cc1cc(O)c(C2=NCCSC(c3ccc(Cl)cc3)C2)c(=O)o1] |
| 173 | 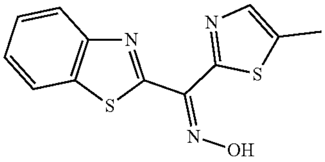 [SMILES: Cc1cnc(/C(=N\O)c2nc3ccccc3s2)s1] |
| 174 | 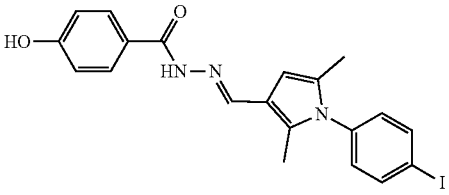 [SMILES: Cc1cc(/C=N/NC(=O)c2ccc(O)cc2)c(C)n1-c1ccc(I)cc1] |
| 175 | 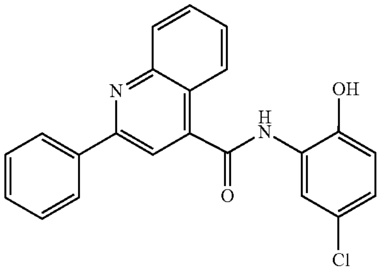 [SMILES: O=C(Nc1cc(Cl)ccc1O)c1cc(-c2ccccc2)nc2ccccc12] |
| 176 | 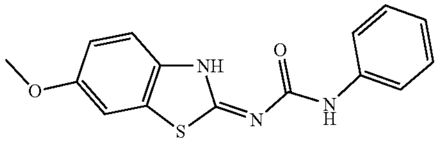 [SMILES: COc1ccc2[nH]/c(=N\C(=O)Nc3ccccc3)sc2c1] |
| 177 | 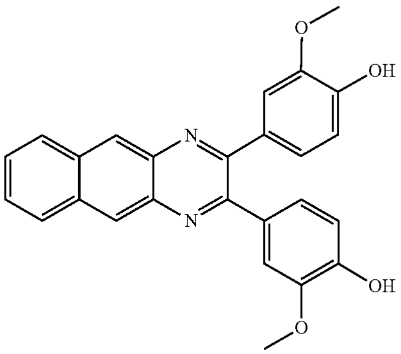 [SMILES: COc1cc(-c2nc3cc4ccccc4cc3nc2-c2ccc(O)c(OC)c2)ccc1O] |

TABLE 1-continued
| Non-Pyrazolopyridazine compounds of the invention | |
|---|---|
| Compound No. | Structure |
| 178 | 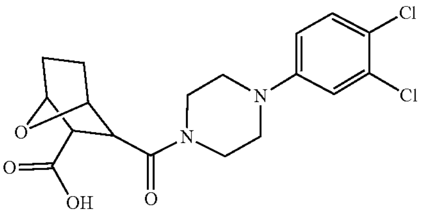 [SMILES: O=C(O)C1C2CCC(O2)C1C(=O)N1CCN(c2ccc(Cl)c(Cl)c2)CC1] |
| 179 | 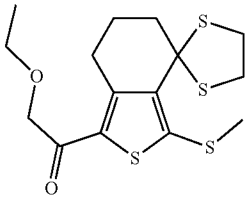 [SMILES: CCOCC(=O)c1sc(SC)c2c1CCCC21SCCS1] |
| 180 | 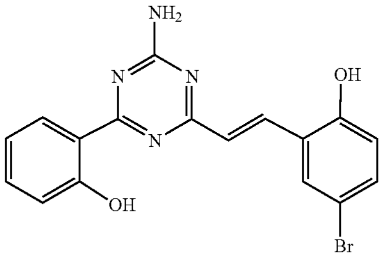 [SMILES: Nc1nc(/C=C/c2cc(Br)ccc2O)nc(-c2ccccc2O)n1] |
| 181 | 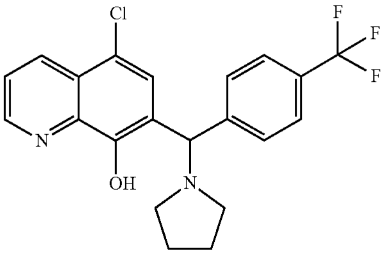 [SMILES: Oc1c(C(c2ccc(C(F)(F)F)cc2)N2CCCC2)cc(Cl)c2cccnc12] |
| 182 | 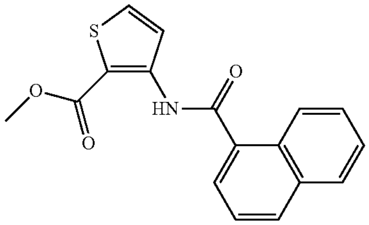 [SMILES: COC(=O)c1sccc1NC(=O)c1cccc2ccccc12] |
| 183 | 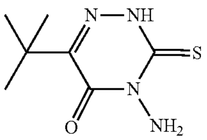 |
| 184 | 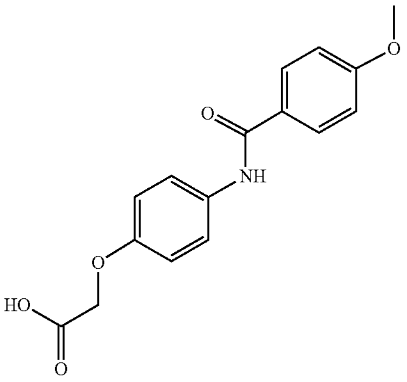 [SMILES: COc1ccc(C(=O)Nc2ccc(OCC(=O)O)cc2)cc1] |
| 185 | 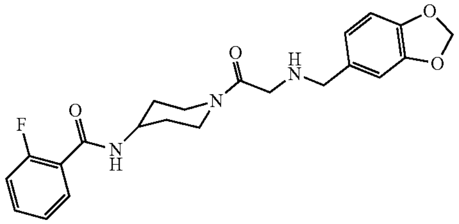 [SMILES: O=C(NC1CCN(C(=O)CNCc2ccc3c(c2)OCO3)CC1)c1ccccc1F] |
| 186 | 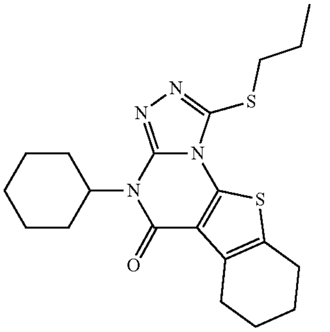 [SMILES: CCCSc1nnc2n(C3CCCCC3)c(=O)c3c4c(sc3n12)CCCC4] |
| 187 | 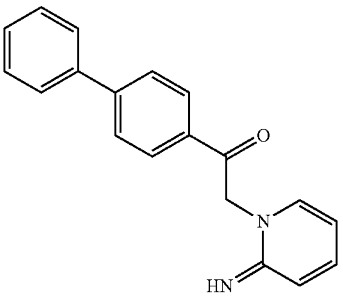 [SMILES: N=c1ccccn1CC(=O)c1ccc(-c2ccccc2)cc1] |
| 188 | 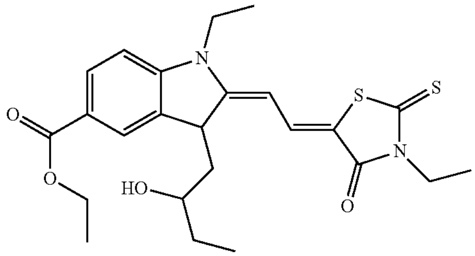 [SMILES: CCOC(=O)c1ccc2c(c1)C(CC(O)CC)/C(=C\C=C1/SC(=S)N(CC)C1=O)N2CC] |

TABLE 1-continued
| Compound No. | Structure |
|---|---|
| 189 | 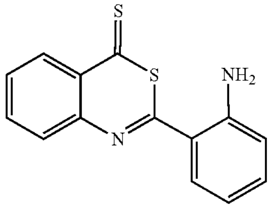 [SMILES: Nc1ccccc1-c1nc2ccccc2c(=S)s1] |
| 190 | 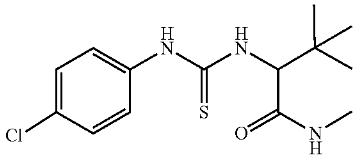 [SMILES: CNC(=O)C(NC(=S)Nc1ccc(Cl)cc1)C(C)(C)C] |
| 191 | 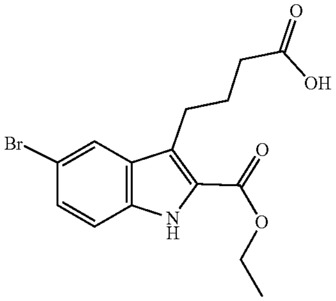 [SMILES: CCOC(=O)c1[nH]c2ccc(Br)cc2c1CCCC(=O)O] |
| 192 | 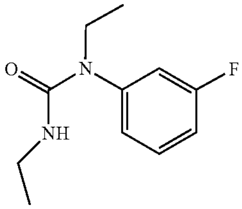 |
| 193 | 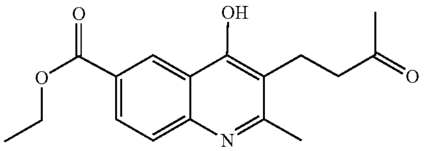 [SMILES: CCOC(=O)c1ccc2nc(C)c(CCC(C)=O)c(O)c2c1] |
| 194 | 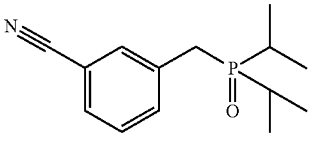 [SMILES: CC(C)P(=O)(Cc1cccc(C#N)c1)C(C)C] |
| 195 | 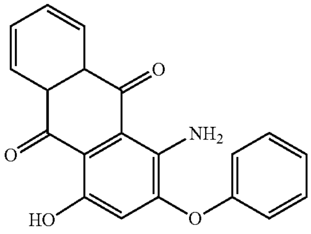 [SMILES: Nc1c(Oc2ccccc2)cc(O)c2c1C(=O)C1C=CC=CC1C2=O] |
| 196 | 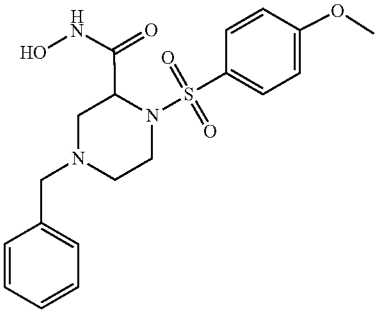 [SMILES: COc1ccc(S(=O)(=O)N2CCN(Cc3ccccc3)CC2C(=O)NO)cc1] |
| 197 | 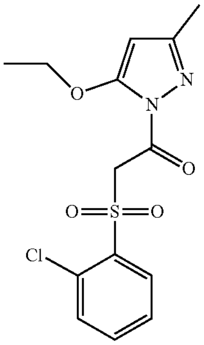 [SMILES: CCOc1cc(C)nn1C(=O)CS(=O)(=O)c1ccccc1Cl] |
| 198 | 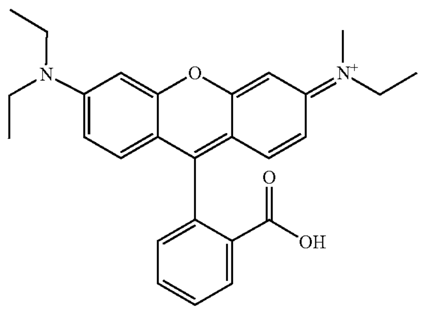 [SMILES: CCN(CC)c1ccc2c(-c3ccccc3C(=O)O)c3cc/c(=[N+](/C)CC)cc-3oc2c1] |
| 199 | 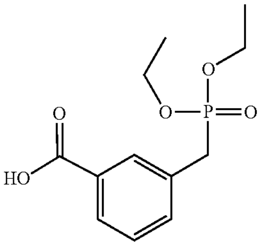 [SMILES: CCOP(=O)(Cc1cccc(C(=O)O)c1)OCC] |
Non-Pyrazolopyridazine compounds of the invention TABLE 1-continued
| Non-Pyrazolopyridazine compounds of the invention | |
|---|---|
| Compound No. | Structure |
| 200 | 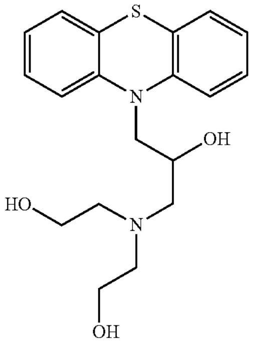 [SMILES: OCCN(CCO)CC(O)CN1c2ccccc2Sc2ccccc21] |
| 201 | 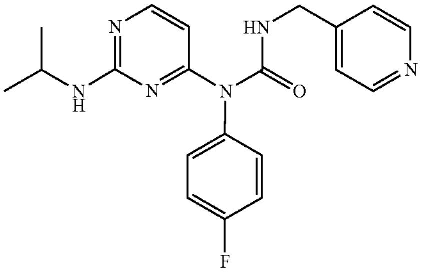 [SMILES: CC(C)Nc1nccc(N(C(=O)NCc2ccncc2)c2ccc(F)cc2)n1] |
| 202 | 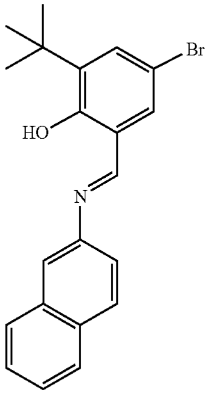 [SMILES: CC(C)(C)c1cc(Br)cc(/C=N/c2ccc3ccccc3c2)c1O] |
| 203 | 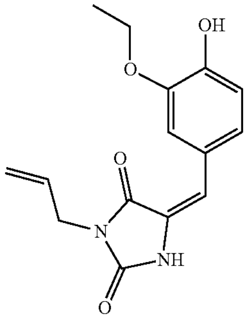 [SMILES: C=CCN1C(=O)N/C(=C/c2ccc(O)c(OCC)c2)C1=O] |
TABLE 1-continued
| Non-Pyrazolopyridazine compounds of the invention | |
|---|---|
| Compound No. | Structure |
| 204 | 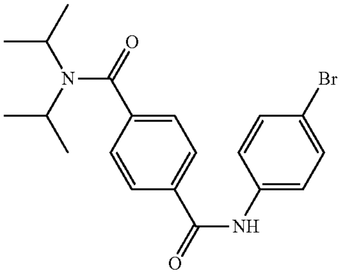 [SMILES: CC(C)N(C(=O)c1ccc(C(=O)Nc2ccc(Br)cc2)cc1)C(C)C] |
| 205 | 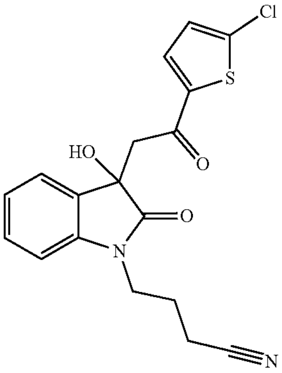 [SMILES: N#CCCCN1C(=O)C(O)(CC(=O)c2ccc(Cl)s2)c2ccccc21] |
| 206 | 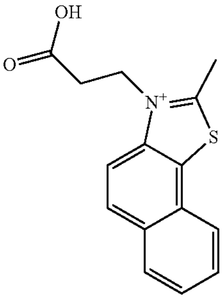 [SMILES: Cc1sc2c3ccccc3ccc2[n+]1CCC(=O)O] |
| 207 | 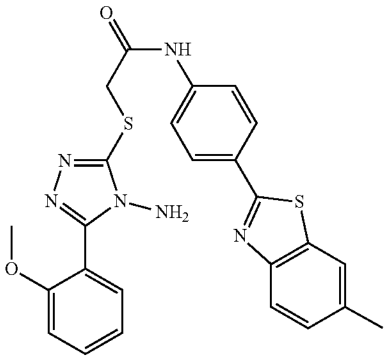 [SMILES: COc1ccccc1-c1nnc(SCC(=O)Nc2ccc(-c3nc4ccc(C)cc4s3)cc2)n1N] |

TABLE 1-continued

Non-Pyrazolopyridazine compounds of the invention

| Compound No. | Structure |
|---|---|
| 208 | 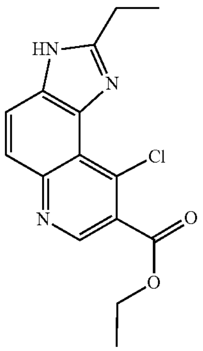 [SMILES: CCOC(=O)c1cnc2ccc3[nH]c(CC)nc3c2c1Cl] |
| 209 | 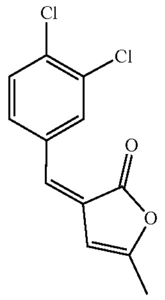 [SMILES: CC1=C/C(=C/c2ccc(Cl)c(Cl)c2)C(=O)O1] |
| 210 | 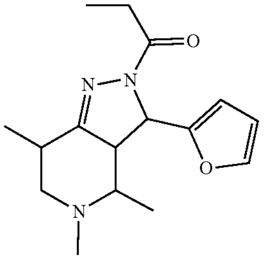 [SMILES: CCC(=O)N1N=C2C(C)CN(C)C(C)C2C1c1ccco1] |
| 211 | 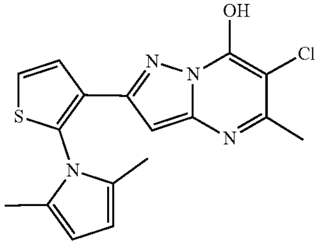 [SMILES: Cc1nc2cc(-c3ccsc3-n3c(C)ccc3C)nn2c(O)c1Cl] |

TABLE 1-continued

Non-Pyrazolopyridazine compounds of the invention

| Compound No. | Structure |
|---|---|
| 212 | 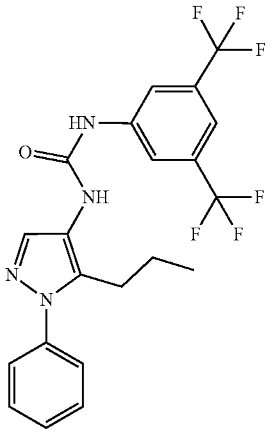 [SMILES: CCCc1c(NC(=O)Nc2cc(C(F)(F)F)cc(C(F)(F)F)c2)cnn1-c1ccccc1] |
| 213 | 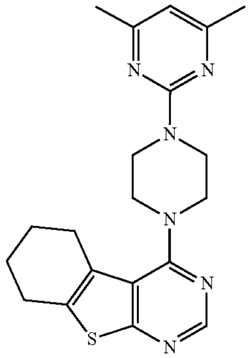 [SMILES: Cc1cc(C)nc(N2CCN(c3ncnc4sc5c(c34)CCCC5)CC2)n1] |

Some of the compounds disclosed herein, for example, Compounds 44, 63, 72, 74, 83, 88, 89, 98-101, 111, 124a, 124b, Vp, Vq, Vt, VIj, VIt, VIu, VIx, VIy, XIIIa, XIIIe, XIIIf, XIIIg, XIIIh, XIIIi, XIIIv, and XIIIw are depicted having a bold or hatched wedge, indicating absolute stereochemistry.

In some embodiments, each of one or more hydrogen atoms of a compound of the invention is replaced with a deuterium atom.

The compounds of the invention can be in the form of a salt. In some embodiments, the salt is a pharmaceutically acceptable salt. Pharmaceutically acceptable salts include, for example, acid-addition salts and base-addition salts. The acid that forms an acid-addition salt can be an organic acid or an inorganic acid. A base that forms a base-addition salt can be an organic base or an inorganic base. In some embodiments, a pharmaceutically acceptable salt is a metal salt. In some embodiments, a pharmaceutically acceptable salt is an ammonium salt.

Acid-addition salts can arise from the addition of an acid to the free-base form of a compound of the invention. In some embodiments, the acid is organic. In some embodiments, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid-addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound of the invention having a carboxyl group. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, and a zinc salt.

Ammonium salts can arise from the addition of ammonia or an organic amine to a compound of the invention having a carboxyl group. Non-limiting examples of suitable organic amines include triethyl amine, diisopropyl amine, ethanol amine, diethanol amine, triethanol amine, morpholine. N-methylmorpholine, piperidine, N-methylpiperidine, N-ethylpiperidine, dibenzyl amine, piperazine, pyridine, pyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethylammonium salt, a diisopropylammonium salt, an ethanolammonium salt, a diethanolammonium salt, a triethanol ammonium salt, a morpholinium salt, an N-methylmorpholinium salt, a piperidinium salt, an N-methylpiperidinium salt, an N-ethylpiperidinium salt, a dibenzylammonium salt, a piperazinium salt, a pyridinium salt, a pyrrazolium salt, an imidazolium salt, a pyrazinium salt, an ethylenediammonium salt, an N,N'-dibenzylethylenediammonium salt, a procaine salt, a chloroprocaine salt, a choline salt, a dicyclohexylammonium salt, and a N-methylglucamine salt.

Methods for Treatment or Prevention

The present invention provides methods for treating cancer, comprising administering to a subject in need thereof an effective amount of a compound of the invention, wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma. In some embodiments, the subject is human. In some embodiments, the subject is a *Canis* sp., e.g., a dog, and in some embodiments, the subject is a *Felis* sp., e.g., a cat. In some embodiments, the compound of the invention is Compound 85 or a pharmaceutically acceptable salt thereof.

The present invention provides methods for preventing cancer, comprising administering to a subject in need thereof an effective amount of a compound of the invention, wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma. In some embodiments, the subject is human. In some embodiments, the subject is a *Canis* sp., e.g., a dog, and in some embodiments, the subject is a *Felis* sp., e.g., a cat. In some embodiments, the compound of the invention is Compound 85 or a pharmaceutically acceptable salt thereof.

The present invention provides methods for reducing risk of developing cancer, comprising administering to a subject in need thereof an effective amount of a compound of the invention, wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma. In some embodiments, the subject is human. In some embodiments, the subject is a *Canis* sp., e.g., a dog, and in some embodiments, the subject is a *Felis* sp., e.g., a cat. In some embodiments, the compound of the invention is Compound 85 or a pharmaceutically acceptable salt thereof.

In some embodiments, colorectal cancer is colorectal adenocarcinoma, gastrointestinal carcinoid tumor, primary colorectal lymphoma, gastrointestinal stromal tumor, leiomyosarcoma of the colon or the rectum, or melanoma of the colon or the rectum.

In some embodiments, glioblastoma is primary glioblastoma or secondary glioblastoma.

In some embodiments, lung cancer is non-small cell lung cancer (NSCLC), small cell lung cancer (SCLC), lung carcinoid tumor, adenoid cystic carcinoma of the lungs, lymphoma of the lungs, or sarcoma of the lungs. In some embodiments, NSCLC is adenocarcinoma, squamous cell carcinoma, large cell carcinoma, adenosquamous carcinoma or sarcomatoid carcinoma.

In some embodiments, ovarian cancer is epithelial ovarian carcinoma, an ovarian germ cell tumor, an ovarian stromal tumor, primary peritoneal carcinoma (also known as extra-ovarian primary peritoneal carcinoma or serous surface papillary carcinoma), or fallopian tube cancer. In some embodiments, epithelial ovarian carcinoma is serous carcinoma, clear cell carcinoma, mucinous carcinoma, endometrioid carcinoma. In some embodiments, epithelial ovarian carcinoma is Grade 1 epithelial ovarian carcinoma or Grade 3 epithelial ovarian carcinoma. In some embodiments, the ovarian germ cell tumor is a teratoma, dysgerminoma, endodermal sinus tumor, or choriocarcinoma. In some embodiments, the ovarian stromal tumor is a granulosa cell tumor, granulosa-theca tumor, or Sertoli-Leydig cell tumor.

In some embodiments, pancreatic cancer is cancer of the exocrine pancreas or ampullary cancer. In some embodiments, cancer of the exocrine pancreas is pancreatic adenocarcinoma, an adenosquamous carcinoma, a squamous cell carcinoma, signet ring cell carcinoma, undifferentiated carcinoma, or undifferentiated carcinoma with giant cells. In some embodiments, pancreatic cancer is pancreatic adenocarcinoma.

In some embodiments, cervical cancer is squamous cell carcinoma, adenocarcinoma, or adenosquamous carcinoma (also known as mixed carcinoma). In some embodiments, cervical cancer is melanoma developed in the cervix, sarcoma developed in the cervix, or lymphoma developed in the cervix.

In some embodiments, prostate cancer is adenocarcinoma, small cell carcinoma, a neuroendocrine tumor (other than a small cell carcinoma), transitional cell carcinoma, or sarcoma. In some embodiments, prostate cancer is prostatic adenocarcinoma.

In some embodiments, breast cancer is invasive breast cancer, noninvasive breast cancer, inflammatory breast cancer, sarcoma of the breast, metaplastic carcinoma, adenocystic carcinoma, phyllodes tumor or angiosarcoma. In some embodiments, breast cancer is estrogen-positive, HER2-positive, or triple-negative.

In some embodiments, gastric cancer (also known as stomach cancer) is gastric adenocarcinoma, lymphoma, gastrointestinal stromal tumor (GIST), a carcinoid tumor, squamous cell carcinoma, small cell carcinoma, or leiomyosarcoma. In some embodiments, gastric cancer is gastric adenocarcinoma.

In some embodiments, head and neck cancer is head and neck squamous cell cancer. In some embodiments, head and neck cancer is cancer of the oral cavity, cancer of the hyarynx, cancer of the larynx, cancer of the paranasal sinuses, cancer of the nasal cavity, or cancer of the salivary glands. In some embodiments, head and neck cancer is metastatic squamous neck cancer with unknown (occult) primary.

In some embodiments, liver cancer is primary liver cancer or secondary liver cancer (also known as metastatic liver cancer). In some embodiments, primary liver cancer is hepatocellular carcinoma (HCC), intrahepatic cholangiocarcinoma (bile duct cancer), angiosarcoma of the liver, hemangiosarcoma of the liver, or hepatoblastoma.

In some embodiments, melanoma is skin melanoma. In some embodiments, skin melanoma is superficial spreading melanoma, nodular melanoma, lentigo maligna melanoma, or acral lentiginous melanoma. In some embodiments, melanoma is melanoma formed in the eyes, mouth, genitals, or anal area.

In some embodiments, lymphopoietic cancer is lymphosarcoma, reticulosarcoma, Hodgkin's disease, leukaemia, aleukaemia, or cancer of the lymphatic tissue.

In some embodiments, hematopoietic cancer is leukemia, lymphoma or myeloma. In some embodiments, hematopoietic cancer is non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), or chronic myeloid leukemia (CML).

In some embodiments, soft tissue cancer is angiosarcoma, dermatofibrosarcoma protuberans, epithelioid sarcoma, gastrointestinal stromal tumor (GIST), Kaposi's sarcoma, leiomyosarcoma, liposarcoma, malignant peripheral nerve sheath tumors, myxofibrosarcoma, rhabdomyosarcoma, solitary fibrous tumor, synovial sarcoma, undifferentiated pleomorphic sarcoma, adult fibrosarcoma, alveolar soft-part sarcoma, clear cell sarcoma, desmoplastic small round cell tumor, fibromyxoid sarcoma, malignant mesenchymoma, or malignant peripheral nerve sheath tumor. In some embodiments, angiosarcoma is hemangiosarcoma or lymphangiosarcoma. In some embodiments, malignant peripheral nerve sheath tumor is neurofibrosarcoma, malignant schwannoma, or neurogenic sarcoma.

In some embodiments, the osteosarcoma (also known as osteogenic sarcoma) is osteoblastic osteosarcoma, chondroblastic osteosarcoma, fibroblastic osteosarcoma, cell sarcoma, telangiectatic osteosarcoma, high-grade surface (juxtacortical high grade) osteosarcoma, pagetoid osteosarcoma, extraskeletal osteosarcoma, post-radiation osteosarcoma, periosteal Juxtacortical intermediate grade) osteosarcoma, parosteal (juxtacortical low grade) osteosarcoma, or intramedullary or intraosseous well differentiated osteosarcoma.

In some embodiments, the methods fir treating osteosarcoma, preventing osteosarcoma, or reducing risk of developing osteosarcoma is in a *Canis* sp., e.g., a dog. In some embodiments, the dog weighs about 10 pounds or greater, about 30 pounds or greater, about 50 pounds or greater, or about 110 pounds or greater. In some embodiments, the dog is of the breed or mixture comprising the breed of Irish Wolfhound, Greyhound, Akbash, Saint Bernard, Leonberger, Rottweiler, Caucasian Ovtcharka, Scottish Deerhound, Curly-Coated Retriever, Anatolian Shepherd, Mastiff, Great Pyrenees, Tosa (Japanese Mastiff), Great Dane, Flat-Coated Retriever, Mastiff (Bull), Brazilian Fila, Irish Setter, Irish Water Spaniel, Mastiff (Tibetian), Golden Retriever, Labrador Retriever, Great Dane, Boxers, Doberman Pinscher, German Shepherd, Bernese Mountain dog, Samoyed, Borzoi, Weimaraner, Miniature Schnauzer, Cocker Spaniel, or Cairn Terrier. In some embodiments, the dog's age is in the range of about 4 to about 18 years old. In some embodiment, the dog's age is in the range of about 5 to about 14 years old.

In some embodiments, cancer is characterized by one or more mutations in the breast cancer 1 (BRCA1) or breast cancer 2 (BRCA2) genes. BRCA1 and BRCA2 are tumor suppressor genes, and encode proteins involved in DNA damage repair. Mutations that alter expression or activity of the BRCA1 or BRCA2 proteins may lead to the accumulation of genetic alterations in a cell, and can lead to cancer in a subject. Such mutations are referred to herein as "disease-associated mutations." In some embodiments, the cancer is characterized one or more mutations in BRCA1 and BRCA2 genes. In some embodiments, the cancer is characterized one or more mutations in BRCA1 gene but has no mutations in BRCA2 gene. In some embodiments, the cancer is characterized one or more mutations in BRCA2 gene but has no mutations in BRCA1 gene. In some embodiments, the cancer has no mutations in BRCA1 or BRCA2 genes.

In some embodiments, cancer is characterized by one or more disease-associated mutations in BRCA1 or BRCA2. In some embodiments, cancer is characterized by one or more disease-associated mutations in BRCA1 and BRCA2. In some embodiments, cancer is characterized by one or more disease-associated mutations in BRCA1 but harbors no disease-associated mutations in BRCA2. In some embodiments, cancer is characterized by one or more disease-associated mutations in BRCA2 but harbors no disease-associated mutations in BRCA1. In some embodiments, cancer is characterized by one or more disease-associated mutations in BRCA1 or BRCA2.

In some embodiments, cancer has one or more deficiencies in BRCA1 or BRCA2. In some embodiments, cancer has one or more deficiencies in BRCA1 and BRCA2. In some embodiments, cancer has one or more deficiencies in BRCA1 but harbors no deficiencies BRCA2. In some embodiments, cancer has one or more deficiencies in BRCA2 but harbors no deficiencies BRCA1. In some embodiments, cancer has no deficiencies in BRCA1 or BRCA2.

In some embodiments, cancer is BRCA-driven cancer. In some embodiments, cancer is BRCA1-driven cancer. In some embodiments, cancer is BRCA2-driven cancer. In some embodiments, cancer is BRCA1- and BRCA2-driven cancer. In some embodiments, cancer is neither BRCA1- nor BRCA2-driven cancer.

In some embodiments, the present methods for treating cancer, for preventing cancer, or reducing risk of developing cancer, further comprise administering to the subject another anti-cancer therapy. In some embodiments, the other anti-cancer therapy is administered before administering the compound of the invention. In some embodiments, the other anti-cancer therapy is administered concurrently with the administration of the compound of the invention. In some embodiments, the other anti-cancer therapy is administered subsequent to administering the compound of the invention. In some embodiments, the compound of the invention is Compound 85 or a pharmaceutically acceptable salt thereof.

In some embodiments, the other anti-cancer therapy is neoadjuvant therapy. In some embodiments, the other anti-cancer therapy is an adjuvant therapy.

In some embodiments, the other anti-cancer therapy is chemotherapy, targeted therapy, hormone therapy, immunotherapy, T-cell therapy, or stem cell therapy.

In some embodiments, the chemotherapy is an alkylating agent, an antimetabolite, an anthracycline antibiotic, a non-anthracycline antibiotic, a topoisomerase inhibitor, a mitotic inhibitor, or a corticosteroid.

In some embodiments, the alkylating agent is cisplatin, cyclophosphamide, melphalan, oxaliplatin, temozolomide, or a nitrosourea.

In some embodiments, the antimetabolite is azacitidine, 5-fluorouracil, 6-mercaptopurine, gemcitabine, hydroxyurea or methotrexate.

In some embodiments, the anthracycline or non-anthracycline antibiotic is daunorubicin, doxorubicin, epirubicin, idarubicin, valrubicin or bleomycin.

In some embodiments, the topoisomerase inhibitor is irinotecan, topotecan, etoposide (VP-16), or mitoxantrone.

In some embodiments, the mitotic inhibitor is docetaxel, nab-paclitaxel, paclitaxel, vinblastine, vincristine or vinorelbine.

In some embodiments, the corticosteroid is prednisone, methylprednisolone or dexamethasone.

In some embodiments, the targeted therapy is herceptin, mabthera, or avastin.

In some embodiments, the hormone therapy is tamoxifen or triptorelin.

In some embodiments, the immunotherapy is an anti-PD-L1 antibody, an anti-PD-1 antibody, or an anti-CTLA4 antibody.

In some embodiments, the anti-PD-L1 antibody is atezolizumab, durvalumab, avelumab, cosibelimab, envafolimab, BMS-936559 (BMS), MEDI-4736 (MedImmune) MPDL3280A (Genentech/Roche), or (Affymetrix eBioscience (catalog No. 16.5983.82)).

In some embodiments, the anti-PD-L1 antibody is nivolumab, pembrolizumab, lambrolizumab, avelumab, tislelizumab, cemiplimab, cetrelimab, camrelizumab, spartalizumab, sintilimab, toripalimab, dostarlimab, retifanlimab, zimberelimab, AMP-224 (Medimmune), AMP 514 (MedImmune), BMS-936559 (BMS), MEDI4736 (Roche/Genentech), or Sym021 (Symphogen).

In some embodiments, the anti-CTLA4 antibody is ipilimumab or tremelimumab

In some embodiments, the immunotherapy is atezolizumab, durvalumab, avelumab, cosibelimab, envafolimab, nivolumab, pembrolizumab, pidilizumab, lambrolizumab, avelumab, tislelizumab, cemiplimab, cetrelimab, camrelizumab, spartalizumab, sintilimab, toripalimab, dostarlimab, retifanlimab, zimberelimab, ipilimumab or tremelimumab, alemtuzumab, trastuzumab, bevacizumab, cetuximab, ibritumomab tiuxetan, brentuximab vedotin, ado-trastuzumab emtansine, denileukin diftitox, or blinatumomab.

In some embodiments, the stem cell therapy is blood-forming stem cells.

The present invention provides methods for treating an inflammatory disease or an autoimmune disease, comprising administering to a subject in need thereof an effective amount of a compound of the invention. In some embodiments, the subject is human. In some embodiments, the subject is a *Canis* sp., e.g., a dog, and in some embodiments, the subject is a *Felis* sp., e.g., a cat. In some embodiments, the compound of the invention is Compound 85 or a pharmaceutically acceptable salt thereof.

The present invention provides methods for preventing an inflammatory disease or an autoimmune disease, comprising administering to a subject in need thereof an effective amount of a compound of the invention. In some embodiments, the subject is human. In some embodiments, the subject is a *Canis* sp., e.g., a dog, and in some embodiments, the subject is a *Felis* sp., e.g., a cat. In some embodiments, the compound of the invention is Compound 85 or a pharmaceutically acceptable salt thereof.

The present invention provides methods for reducing risk of developing an inflammatory disease or an autoimmune disease, comprising administering to a subject in need thereof an effective amount of a compound of the invention. In some embodiments, the subject is human. In some embodiments, the subject is a *Canis* sp., e.g., a dog, and in some embodiments, the subject is a *Felis* sp., e.g., a cat. In some embodiments, the compound of the invention is Compound 85 or a pharmaceutically acceptable salt thereof.

In some embodiments, the inflammatory disease or the autoimmune disease is rheumatoid arthritis, juvenile idiopathic arthritis, colitis, atherosclerosis, cardiac myopathy, Crohn's disease, celiac disease, dermatitis herpetiformis, autoimmune blistering disease, epidermolysis bullosa, type 1 diabetes, asthma, lupus, dermatomyositis, alopecia areata, antiphospholipid antibody syndrome, autoimmune hepatitis, multiple sclerosis, Guillain-Barre syndrome, demyelinating polyneuropathy, psoriasis, Graves's disease, Hashimoto's thyroiditis, myasthenia gravis, vasculitis, hemolytic anemia, idiopathic thrombocytopenic purpura, inflammatory bowel disease, inflammatory myopathy, primary biliary cirrhosis, scleroderma, Sjögren's syndrome, systemic lupus erythematosus, or vitiligo.

In some embodiments, the inflammatory disease is rheumatoid arthritis, juvenile idiopathic arthritis, colitis, atherosclerosis, cardiac myopathy, Crohn's disease, celiac disease, dermatitis herpetiformis, autoimmune blistering disease, epidermolysis bullosa, asthma, lupus, dermatomyositis, alopecia areata, autoimmune hepatitis, multiple sclerosis, Guillain-Barre syndrome, demyelinating polyneuropathy, psoriasis, Graves's disease, Hashimoto's thyroiditis, myasthenia gravis, vasculitis, idiopathic thrombocytopenic purpura, inflammatory bowel disease, inflammatory myopathy, primary biliary cirrhosis, scleroderma, Sjögren's syndrome, systemic lupus erythematosus, or vitiligo.

In some embodiments, the autoimmune disease is rheumatoid arthritis, juvenile idiopathic arthritis, colitis, atherosclerosis, cardiac myopathy, Crohn's disease, celiac disease, dermatitis herpetiformis, autoimmune blistering disease, epidermolysis bullosa, type 1 diabetes, asthma, lupus, dermatomyositis, alopecia areata, antiphospholipid antibody syndrome, autoimmune hepatitis, multiple sclerosis, Guillain-Barre syndrome, demyelinating polyneuropathy, psoriasis, Graves's disease, Hashimoto's thyroiditis, myasthenia gravis, vasculitis, hemolytic anemia, idiopathic thrombocytopenic purpura, inflammatory bowel disease, inflammatory myopathy, primary biliary cirrhosis, scleroderma, Sjögren's syndrome, systemic lupus erythematosus, or vitiligo.

In some embodiments, the autoimmune blistering disease is autoimmune blistering skin disease.

In some embodiments of any of the methods disclosed herein, the compound of the invention is any of Compounds 1-35, 37-39, 42, 43, 44, 45, 46, 47-97, 98-123, 124a, 124b, 125-213, Va-Vz, Vaa-Vii, VIa-VIy, VIIa-VIId, XIIIa-XIIIz, XIVa, and XVa-XVm, or a pharmaceutically acceptable salt thereof. In some embodiments of any of the methods disclosed herein, the compound of the invention has the structure of Formula I, II, III, IV, V, VI, VII, XIII, XIV or XV, or is a pharmaceutically acceptable salt thereof. In some embodiments of any of the methods disclosed herein, the compound of the invention has the structure of Formula II, or a pharmaceutically acceptable salt thereof. In some embodiments of any of the methods disclosed herein, the compound of the invention is Compound 85, or a pharmaceutically acceptable salt thereof.

Heat Shock Proteins

Heat shock proteins (Hsps) are classified according to their molecular weight and include the small Hsps, Hsp40, Hsp60, Hsp70, Hsp90 and Hsp100 families (Table 2).

TABLE 2

Illustrative Families of Heat Shock Proteins

| Approximate molecular weight (kD) | Heat shock protein |
|---|---|
| 10 kD | Hsp10 |
| 20-30 kD | HspB group, includes Hsp27 |
| 40 kD | Hsp40 |
| 60 kD | Hsp60 |
| 70 kD | HspA group, includes Hsp71, Hsp70, Hsp72, Grp78 (BiP), Hsx70 in primates |
| 70 kD | Ribosome-associated complex (RAC) |
| 90 kD | HspC group, includes Hsp90, Grp94 |
| 100 kD | HspH group, includes Hsp104, Hsp110 |

In some embodiments, a compound of the invention or a metabolite thereof binds to an Hsp. In some embodiments, a compound of the invention or a metabolite thereof covalently binds to an Hsp.

In some embodiments, the binding of a compound of the invention or a metabolite thereof to an Hsp results in the treatment, prevention, or reduction of risk of developing cancer, wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma. In some embodiments, the compound of the invention is Compound 85 or a pharmaceutically acceptable salt thereof.

In some embodiments, the binding of a compound of the invention or a metabolite thereof to an Hsp results in the treatment, prevention, or reduction of risk of developing an inflammatory disease or an autoimmune disease. In some embodiments, the compound of the invention is Compound 85 or a pharmaceutically acceptable salt thereof.

In some embodiments, the Hsp is a member of the Hsp10 family, Hsp40 family, Hsp60 family, Hsp70 family, Hsp90 family, or Hsp100 family.

Compositions of the Invention

The compound of the invention can be administered to a subject as a component of a composition that comprises a pharmaceutically acceptable carrier or vehicle. Non-limiting examples of suitable pharmaceutical carriers or vehicles include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol, buffered water, and phosphate buffered saline. These compositions can be administered as, for example, drops, solutions, suspensions, tablets, pills, capsules, powders, and sustained-release formulations. In some embodiments, the compositions comprise, for example, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate, and mineral oil. The compositions can additionally comprise lubricating agents, wetting agents, emulsifying and suspending agents, preserving agents, sweetening agents or flavoring agents.

The compositions can comprise an effective amount of a compound of the invention. The compositions can be formulated in a unit dosage form that comprises an effective amount of a compound of the invention. In some embodiments, the compositions comprise, for example, from about 1 ng to about 1,000 mg of a compound of the invention. In some embodiments, the compositions comprise from about 100 mg to about 1,000 mg of a compound of the invention. In some embodiments, the compositions comprise from about 100 mg to about 500 mg of a compound of the invention. In some embodiments, the compositions comprise from about 200 mg to about 300 mg of a compound of the invention.

The dosage of a compound of the invention can vary depending on the symptoms, age, and body weight of the subject, the nature and severity of cancer, inflammatory disease, and/or autoimmune disease, the route of administration, and the form of the composition. The compositions described herein can be administered in a single dose or in divided doses. In some embodiments, the dosage of a compound of the invention ranges from about 0.01 ng to about 10 g per kg body mass of the subject, from about 1 ng to about 0.1 g per kg, or from about 100 ng to about 10 mg per kg.

Administration can be, for example, topical, intraaural, intraocular, parenteral, intravenous, intra-arterial, subcutaneous, intramuscular, intracranial, intraorbital, intraventricular, intracapsular, intraspinal, intracisternal, intraperitoneal, intranasal, aerosol, suppository, or oral. Formulations for oral use include tablets containing a compound of the invention in a mixture with non-toxic pharmaceutically acceptable excipients. These excipients can be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for ocular use can be in the form of eyedrops.

A compound of the invention can be provided in lyophilized form for reconstituting, for instance, in isotonic, aqueous, or saline buffers for parental, subcutaneous, intradermal, intramuscular, or intravenous administration. A composition can also be in the form of a liquid preparation useful for oral, intraaural, nasal, or sublingual administration, such as a suspension, syrup or elixir. A composition can also be in a form suitable for oral administration, such as a capsule, tablet, pill, and chewable solid formulation. A composition can also be prepared as a cream for dermal administration as a liquid, a viscous liquid, a paste, or a powder. A composition can also be prepared as a powder for pulmonary administration with or without an aerosolizing component.

The compositions can be in oral, intraaural, intranasal, sublingual, intraduodenal, subcutaneous, buccal, intracolonic, rectal, vaginal, mucosal, pulmonary, transdermal, intradermal, parenteral, intravenous, intramuscular and ocular dosage forms as well as being able to traverse the blood-brain barrier.

The compositions can be administered by various means known in the art. For example, the compositions can be administered orally, and can be formulated as tablets, capsules, granules, powders or syrups. Alternatively, compositions can be administered parenterally as injections (for example, intravenous, intramuscular or subcutaneous), drop infusion preparations or suppositories. For ophthalmic application compositions can be formulated as eye drops or eye ointments. Aural compositions can be formulated as ear drops, ointments, creams, liquids, gels, or salves for application to the ear, either internally or superficially. These formulations can be prepared by conventional means, and the compositions can be mixed with any conventional additive, such as an excipient, a binder, a disintegrating agent, a lubricant, a solubilizing agent, a suspension aid, an emulsifying agent, or a coating agent.

Compositions can include wetting agents, emulsifiers, and lubricants, coloring agents, release agents, coating agents, sweetening, flavoring and perfuming agents, preservatives and antioxidants.

Compositions can be suitable, for example, for oral, intraaural, intraocular, nasal, topical (including buccal and sublingual), rectal, vaginal, aerosol and/or parenteral administration. The compositions can be provided in a unit dosage form, and can be prepared by any methods known in the art.

Formulations suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia. Compositions can also be administered as a bolus, electuary, or paste.

Additional examples of pharmaceutically acceptable carriers or vehicles include: (1) fillers or extenders, such as starches, lactose, sucrose, glucose, mannitol, and/or silicic acid; (2) binders, such as carboxymethyl cellulose, alginates, gelatin, polyvinyl pyrrolidone, sucrose and/or acacia (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; (10) coloring agents; and (11) buffering agents. Similar compositions can be employed as fillers in soft- or hard-filled gelatin capsules.

Liquid dosage forms for oral administration include pharmaceutically acceptable emulsions, microemulsions, gels, solutions, suspensions, syrups and elixirs. The liquid dosage form can contain inert diluents commonly used in the art, for example, water or other solvents, solubilizing agents and emulsifiers, such as ethyl alcohol, isopropyl alcohol, diethyl carbonate, ethyl acetate, benzyl alcohol, benzyl benzoate, propylene glycol, 1,3-butylene glycol, oils such as, cottonseed, groundnut, corn, germ, olive, castor and sesame oils, glycerol, tetrahydrofuryl alcohol, polyethylene glycols, fatty acid esters of sorbitan, and mixtures thereof.

Suspension dosage forms can contain suspending, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The dosage forms for transdermal administration of a subject composition include drops, powders, sprays, ointments, pastes, creams, lotions, gels, solutions, and patches. The ointments, pastes, creams, and gels can contain excipients, such as animal and vegetable fats, oils, waxes, paraffin, starch, tragacanth, cellulose derivatives, polyethylene glycols, silicones, bentonite, silicic acid, talc and zinc oxide, or mixtures thereof.

Powders and sprays can contain excipients such as lactose, talc, silicic acid, aluminum hydroxide, calcium silicates, polyamide powder, or mixtures thereof. Sprays may additionally contain customary propellants, such as chlorofluorohydrocarbons and volatile unsubstituted hydrocarbons, such as butane and propane.

Compositions can be administered by aerosol of solid particles. A non-aqueous (e.g., fluorocarbon propellant) suspension could be used. Some nebulizers can be used because they minimize exposure to shear, which might cause degradation.

An aqueous aerosol can be made by formulating an aqueous solution or suspension of a compound of the invention with any conventional pharmaceutically acceptable carriers or vehicles such non-ionic surfactants (Tweens, Pluronics, or polyethylene glycol); proteins such as serum albumin; sorbitan esters; fatty acids; lecithin; amino acids; buffers; salts; sugars; or sugar alcohols.

Compositions suitable for parenteral administration comprise a compound of the invention and one or more pharmaceutically acceptable sterile isotonic aqueous or non-aqueous solutions, dispersions, suspensions, or emulsions, or sterile powders which can be reconstituted into sterile injectable solutions or dispersions just prior to use, which can contain antioxidants, buffers, bacteriostats, or solutes, which render the formulation isotonic with the blood of the subject, and suspending or thickening agents.

In some embodiments, the compound of the invention is Compound 85 or a pharmaceutically acceptable salt thereof.

Having described the invention with reference to certain embodiments, other embodiments will become apparent to one skilled in the art from consideration of the specification and claims. It will be apparent to those skilled in the art that many modifications, both to materials and methods, may be practiced without departing from the scope of the invention.

Methods for Making the Compounds of the Invention

Methods for making the compounds of the invention are disclosed in U.S. Pat. Nos. 9,227,976, 9,079,909 and 8,765,762, each of which is incorporated by reference herein in its entirety. Compound 85 can be synthesized according to Example 78 of U.S. Pat. No. 9,079,909.

Compound 114 can be synthesized according to Vasilevsky, S. F. Tretyakov, E. V. Cinnolines and pyrazolopyridazines.—Novel synthetic and mechanistic aspects of the Richter reaction. Liebigs Annalen 1995, 775-779 (1995).

Non-limiting examples of synthetic schema that are useful for synthesizing the compounds of the invention include the following.

Scheme 1

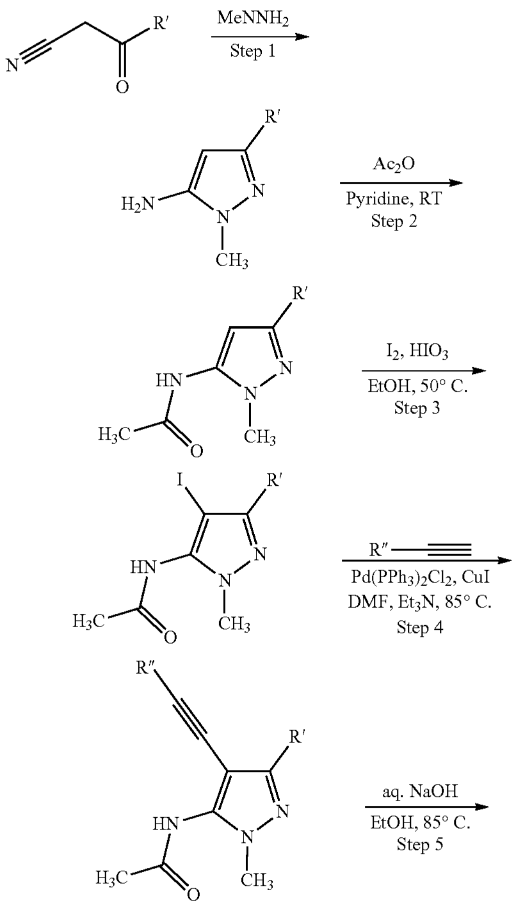

-continued

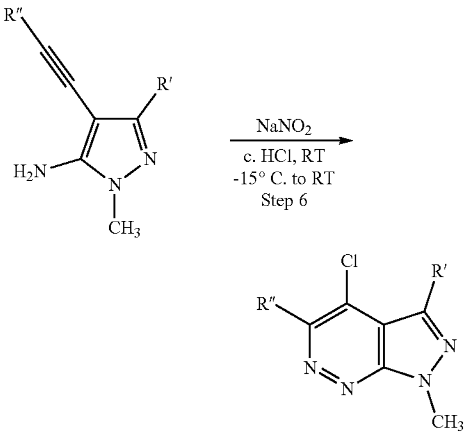

Scheme 1 generally describes the preparation of compounds of the invention having a 1-N-methyl group and where R' and R" are independently an unsubstituted or a substituted phenyl group. For example, a 2-cyanocarbonyl compound in which R' is unsubstituted or substituted phenyl is condensed with N-methylhydrazine to provide a 3-substituted-1-methyl-1H-pyrazol-5-amine. The 5-amino group is acylated, for example, with acetic anhydride in the presence of a base, such as pyridine, to provide a 5-amido compound. The 5-amido compound is iodinated, for example, with a mixture of iodine and iodic acid in a solvent such as ethanol (EtOH) to provide an N-(3-substituted-4-iodo-1-methyl-1H-pyrazol-5-yl)acetamide. A palladium-mediated cross-coupling, such as a Sonagashira cross-coupling, of the acetamide with an R"-substituted terminal alkyne, catalyzed, for example, by a palladium complex such as palladium (II) bistriphenylphosphine dichloride in the presence of copper (I) iodide in a solvent such as dimethylformamide (DMF) with a base such as triethylamine provides a disubstituted alkyne in which R" is unsubstituted or substituted phenyl. Saponification of the alkyne acetamide with a base such as sodium hydroxide in a solvent such as ethanol provides the primary amine. Diazotization of the primary amine with sodium nitrite in concentrated hydrochloric acid provides a diazo intermediate, which cyclizes to provide a compound having a 1-N-methyl group and where R' and R" are independently an unsubstituted or a substituted phenyl group.

Scheme 2

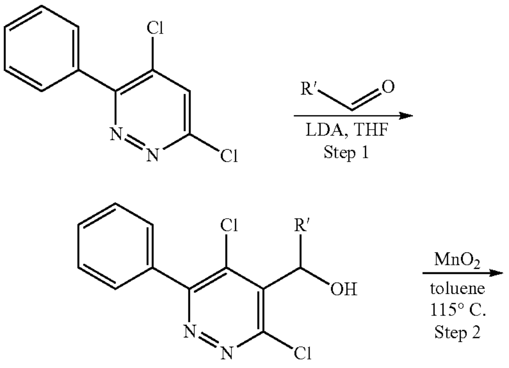

-continued

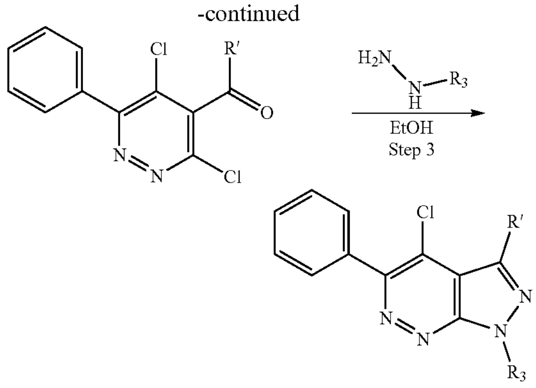

Scheme 2 generally describes the preparation of compounds of the invention having an $R_3$ group and in which R' is an unsubstituted or a substituted phenyl group. R' and $R_3$ can be the same or different. For example, 4,6-dichloro-3-phenylpyridazine is deprotonated with a base such as lithium diisopropyl amide (LDA) in a solvent such as tetrahydrofuran (THF), and the resultant 5-lithio species is condensed with an unsubstituted or a substituted benzaldehyde to provide a secondary alcohol. The alcohol is oxidized to a ketone with an oxidizing agent such as manganese dioxide in a solvent such as toluene. The ketone is condensed with an $R_3$-substituted hydrazine in a solvent such as ethanol to provide an intermediate hydrazone, which cyclizes to provide a compound having a 1-N—$R_3$ group, in which $R_3$ is defined as in Formulas II and III and in which R' is an unsubstituted or a substituted phenyl group.

Scheme 3

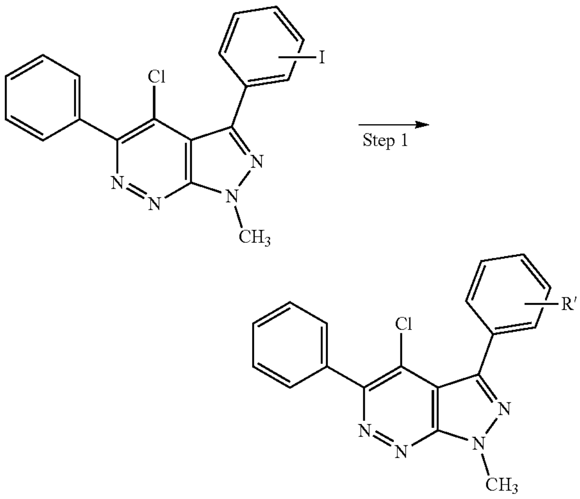

Scheme 3 generally describes the preparation of compounds of the invention having a 1-N-methyl group and where R' is a cyano group, an alkyne, an alkene or an aryl group. For example, 1-methyl-3-iodophenyl-4-chloro-5-phenyl-1H-pyrazolo[3,4-c]pyridazine is coupled with a suitable coupling partner, such as a cyanide salt, a terminal alkyne, an alkenyl halide, or an aryl halide, optionally in the presence of a suitable catalyst such as a palladium complex, optionally in the presence of a non-palladium transition metal salt such as a zinc or copper salt, optionally in the presence of an additive such as triphenylphosphine or an organic amine base, to provide a compound having a 1-N-methyl group and where R' is a cyano group, an alkyne, an alkene or an aryl group. The position of R', i.e., ortho, meta or porn, in the product is the same as the position of the iodo group in the starting material.

Scheme 4

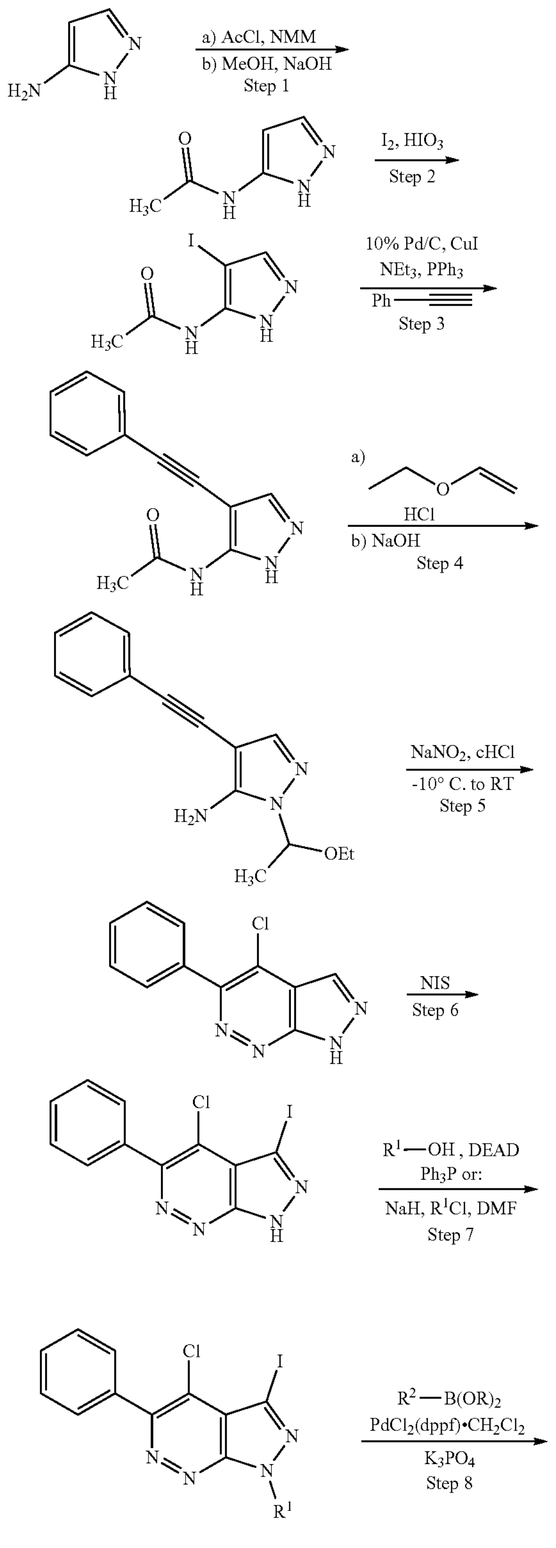

-continued

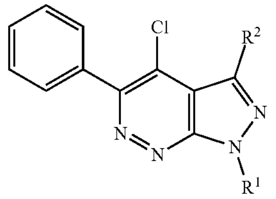

Scheme 4 generally describes the preparation of compounds of the invention.

Scheme A

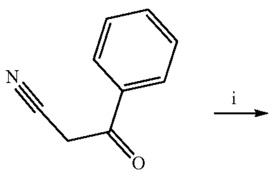

7A

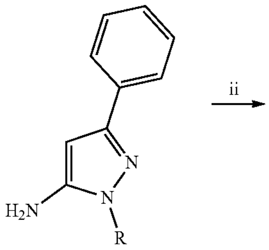

8A R= $CH_2CO_2Et$
9A R= H

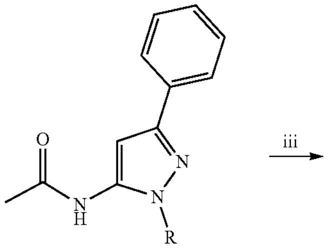

10A R= $CH_2CO_2Et$
11A R= H

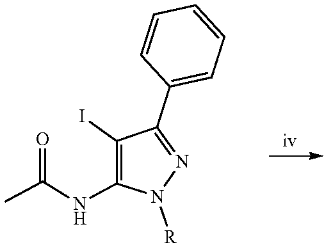

12A R= $CH_2CO_2Et$
13A R= H

-continued

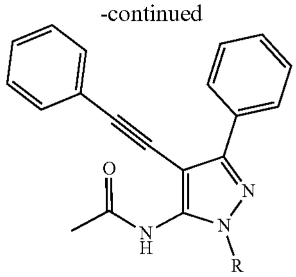

14A R= $CH_2CO_2Et$
15A R= H (i) ethyl hydrazinoacetate hydrochloride, EtOH, reflux, 2 h; (ii) $Ac_2O$, pyridine, 25° C., 16 h or AcCl, N-methylmorpholine, $CH_2Cl_2$, 25° C., 3 h; (iii) $I_2$, $HIO_3$, EtOH, 50° C.; (iv) Phenyl acetylene, $Pd(PPh_3)_2Cl_2$, CuI, $Et_3N$, DMF, 90° C.

Scheme A generally describes the preparation of Ethyl 2-[5-acetamido-3-phenyl-4-(2-phenylethynyl)-1H-pyrazol-1-yl]acetate and N-[3-Phenyl-4-(2-phenylethynyl)-1H-pyrazol-5-yl]acetamide from benzoylacetonitrile.

Compound 8A of Scheme A: Ethyl 2-(5-amino-3-(phenyl)-1-pyrazol yl)acetate

A mixture of benzoylacetonitrile (7A, 44 g, 304 mmol) and ethyl hydrazinoacetate hydrochloride (47 g, 304 mmol) in ethanol (400 mL) is heated to reflux for 2 h. The reaction mixture is concentrated in vacuo. The crude reaction mixture is partitioned between $CH_2Cl_2$ (400 mL) and saturated $NaHCO_3$ (aq). The aqueous phase is extracted with $CH_2Cl_2$ and the organic phases are combined, dried over $MgSO_4$, filtered and evaporated to give compound 8A as a solid (70 g, 95% yield). $^1H$ NMR (400 MHz, $CDCl_3$) δ (ppm) 7.73 (m, 2H), 7.38 (m, 2H), 7.26 (m, 1H), 5.96 (s, 1H), 4.86 (s, 2H), 4.25 (m, 2H), 3.7 (s, 2H), 1.28 (s, 3H).

Compound 10A of Scheme A: Ethyl 2-(5-acetamido-3-phenyl-1H-pyrazol-1-yl)acetate

To a solution of ethyl 2-(5-amino-3-(phenyl)-1H-pyrazol-1-yl)acetate (84, 41.7 g, 0.17 mol) in pyridine (200 mL) is added acetic anhydride (17.4 g, 0.17 mol) dropwise at 0° C. wider an atmosphere of nitrogen. The reaction mixture is stirred at room temperature (RT) for 16 h. The reaction mixture is concentrated in vacuo. The residue is diluted with $CH_2Cl_2$ and water. The layers are separated and the organic layer is washed with water and brine, dried ($MgSO_4$) and concentrated in vacuo. $CH_2Cl_2$ is added to the residue and the solid is collected by filtration, yielding compound 104 as a solid (22 g, 45% yield). The mother liquors are concentrated in vacuo and washed with cold $CH_2Cl_2$ to give a second batch of compound 10A (15 g, 31% yield), $^1H$ NMR (400 MHz, DMSO-$d_6$) δ (ppm) 10.13 (s, 1H), 7.81 (d, 7.6 Hz, 2H), 7.45 (t, J=7.6 Hz, 2H), 7.40-7.32 (m, 1H), 6.80 (s, 1H), 5.07 (s, 2H), 4.22 (q, J=7.1 Hz, 2H), 2.14 (s, 3H), 1.28 (t, J=7.1 Hz, 3H).

Compound 11A of Scheme A: N-(3-Phenyl-1H-pyrazol-5-yl)acetamide

To a solution of 3-phenyl-1H-pyrazol-5-amine (9, 18.6 g, 0.117 mol) and N-methylmorpholine (30.8 mL, 0.281 mol) in $CH_2Cl_2$ (250 mL) is added acetyl chloride (20 mL, 0.281 mol) dropwise at 0° C. under an atmosphere of nitrogen. The reaction mixture is stirred at RT for 3 h. The reaction mixture is diluted with $CH_2Cl_2$ and water. The layers are separated and the organic layer is washed with water and brine, dried (phase separator cartridge) and concentrated in vacuo. Diethyl ether is added to the residue and the solid is collected by filtration, yielding compound 11A as a solid (25.1 g, 88% yield). $^{1}$H NMR (400 MHz, DMSO-$d_6$) δ (ppm) 12.79 (s, 1H), 10.40 (s, 1H), 7.71 (d, J=7.5 Hz, 2H), 7.44 (dd, J=7.6, 7.6 Hz, 2H), 7.34 (dd, J=7.2, 7.2 Hz, 1H), 6.88 (s, 2.02 (s, 3H).

Compound 12A of Scheme A: Ethyl 2-(5-acetamido-4-iodo-3-phenyl-1H-pyrazol-1-yl)acetate A suspension of compound 104 (37 g, 129 mmol), iodic acid (5.6 g. 32 mmol) and iodine (19.7 g, 77 mmol) in ethanol (400 mL) is heated at 50° C. for 2 h and cooled to RT. The reaction mixture is concentrated in vacuo and the residue is eluted through a pad of silica gel with $CH_2Cl_2$/diethyl ether (1:0 to 97:3). The residue is partitioned between $CH_2Cl_2$ and 2 M $Na_2S_2O_3$ solution (aq). The layers are separated and the organic washed is dried ($MgSO_4$), and concentrated in vacuo to give a residue that is partially purified by chromatography (silica gel, $CH_2Cl_2$/isohexane 1:1 to 1:0, then $CH_2Cl_2$/diethyl ether 9:1 to 8:2), then triturated with diethyl ether yielding compound 124 as an off-white solid (43 g, 81% yield). $^{1}$H NMR (400 MHz, $CDCl_3$) as a 3:1 mixture of rotamers δ (ppm) 7.81 (d, J=7.6 Hz, 2H), 7.45-7.35 (m, 3H), 7.15 (br s, 0.75H), 6.85 (br s, 0.25H), 4.97 (s, 2H), 4.25 (q, 3=7.1 Hz, 2H), 2.24 (s, 2.25H), 2.04 (s, 0.75H), 1.30 (t, J=7.1 Hz, 3H).

Compound 13A of Scheme A: N-(4-Iodo-3-phenyl-1H-pyrazol-5-yl)acetamide

A suspension of compound 11A (25.1 g, 0.103 mol), iodic acid (4.5 g, 0.026 mol) and iodine (15.7 g, 0.062 mol) in ethanol (250 mL) is heated at 50° C. for 3 h and cooled to RT. The reaction mixture i concentrated in vacuo and partitioned between $CH_2Cl_2$ and 2 M $Na_2S_2O_3$ solution (aq). The layers are separated and the organic washed with brine, dried (phase separator cartridge), and concentrated in vacuo to give a mixture of compound 134 and starting material 11A (2.2:1, 30.3 g). The mixture is put in reaction again using iodic acid, (1.6 g, 9.6 mmol) and iodine (9.7 g, 38 mmol) in ethanol (250 mL) under the same conditions, to give compound 134 as a solid (31.9 g, 84% yield). $^{1}$H NMR, (400 MHz, $CDCl_3$) δ (ppm) 11.74-11.74 (m, 1H), 7.81 (d, J=7.2 Hz, 2H), 7.59 (s, 1H), 7.49-7.38 (m, 3H), 2.31 (s, 3H).

Compound 14A of Scheme A: Ethyl 2-[5-acetamido-3-phenyl-4-(2-phenylethynyl)-1H-pyrazol-1-yl]acetate Nitrogen is bubbled through a mixture of compound 12A (18.6 g, 45 mmol), phenyl acetylene (9.2 g, 90 mmol), copper iodide (860 mg, 4.5 mmol), triethylamine (200 mL) and DMF (75 mL) for 15 min. Bis(triphenylphosphine) palladium(II) dichloride (1.6 g, 2.25 mmol) is added and the reaction mixture is stirred at 90° C. under nitrogen for 4.5 h. The reaction mixture is cooled to RT, diluted with ethyl acetate and water. The organic phase is washed with water and brine, dried ($MgSO_4$), filtered and concentrated in vacuo. The residue is partially purified by column chromatography (silica gel, $CH_2Cl_2$, then isohexane/ethyl acetate 1:1 followed by $CH_2Cl_2$/ethyl acetate 9:1 to 8:2), then triturated with diethyl ether yielding compound 14A as a solid (13 g, 75% yield). $^{1}$H NMR (400 MHz, DMSO-$d_6$) δ (ppm) 10.38 (s, 1H), 8.13-8.09 (m, 2H), 7.60-7.44 (m, 8H), 5.03 (s, 2H), 4.23 (q, 3=7.1 Hz, 2H), 2.17 (s, 3H), 1.28 (t, J=7.1 Hz, 3H).

Compound 15A of Scheme A: N-[3-Phenyl-4-(2-phenylethynyl)-1H-pyrazol-5-yl]acetamide By a similar procedure to that described for the synthesis of compound 14A, compound 15A (12.5 g, 48% yield) is obtained from compound 13A (31.87 g, 86 mmol). $^{1}$H NMR (400 MHz, $CDCl_3$) δ (ppm) 11.57-11.57 (m, 1H), 8.11 (d, J=7.4 Hz, 2H), 7.91 (s, 1H), 7.55-7.49 (m, 2H), 7.44 (dd, J=7.5, 7.5 Hz, 2H), 7.37 (dd, J=1.9, 5.0 Hz, 4H), 2.32 (s, 3H), Scheme B

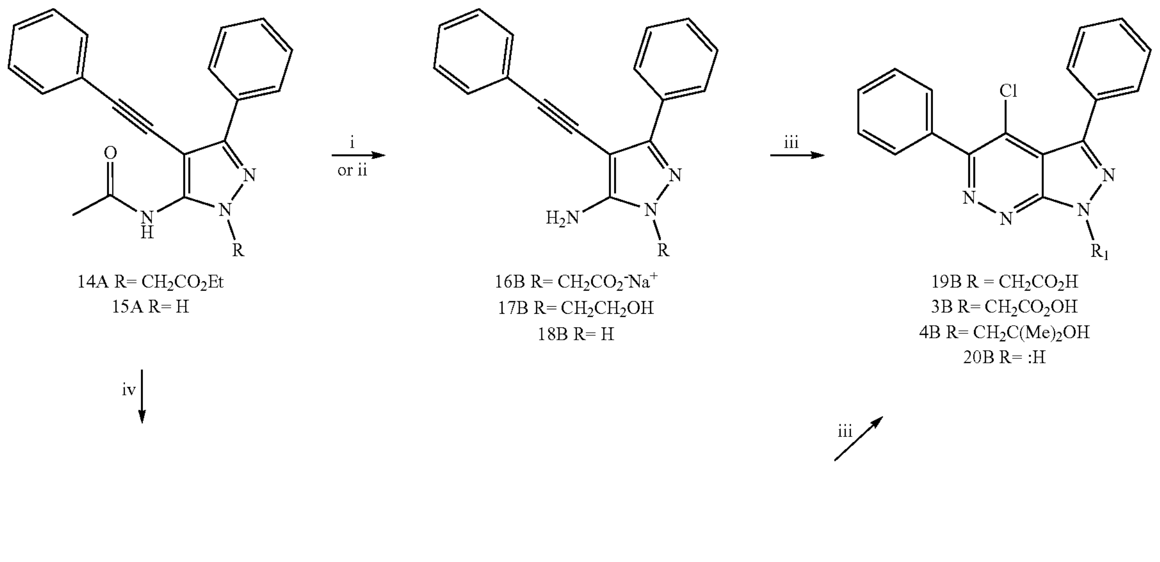

14A R= $CH_2CO_2Et$
15A R= H

16B R= $CH_2CO_2^-Na^+$
17B R= $CH_2CH_2OH$
18B R= H

19B R = $CH_2CO_2H$
3B R= $CH_2CO_2OH$
4B R= $CH_2C(Me)_2OH$
20B R= :H

-continued

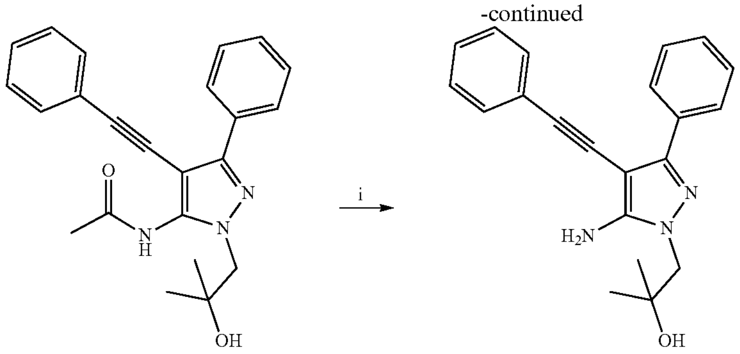

21B 22B (i) NaOH, EtOH, 80° C.; (ii) (a) $NaBH_4$, EtOH, 25° C.; (b) NaOH, EtOH, 80° C.; (iii) $NaNO_2$, c. HCl, -10° C. to 25° C.; (iv) MeMgCl, THF, 0° C. to 25° C.

Scheme B generally describes the preparation of compound 3B and compound 4B.

Compound 16B of Scheme B: Sodium 2-[5-amino-3-phenyl-4-(2-phenylethynyl)-1H-pyrazol-1-yl]acetate A mixture of compound 14B (13 g, 34 mmol), ethanol (150 mL) and 25% NaOH solution (aq) (150 mL) is stirred and heated to 80° C. for 8 h and cooled to RT. Upon cooling, a precipitate is formed. The precipitate is filtered and washed with a cooled mixture of ethyl acetate/water (1:1). The solid is further triturated with diethyl ether, filtered and dried ($MgSO_4$), yielding compound 16B as a solid (9.8 g, 85% yield). $^1$H NMR (400 MHz, DMSO-$d_6$) δ (ppm) 8.06 (d, J=7.8 Hz, 2H), 7.56 (d, J=7.6 Hz, 2H), 7.50-7.39 (m, 4H), 7.39-7.31 (m, 2H), 4.31 (s, 2H).

Compound 17B of Scheme B: 2-[5-Amino-3-phenyl-4-(2-phenylethynyl-1H-)pyrazol-1-yl]ethanl-ol To a suspension of compound 14B (22.4 g, 58 mmol) in ethanol (290 mL) is added sodium borohydride (11 g, 289 mmol) and the reaction mixture is stirred at RT for 16 h. The reaction mixture is partially concentrated to a final volume of 250 mL, A 25% NaOH solution (aq) (250 mL) is added and the reaction mixture is stirred at 80° C. for 4 h. The reaction mixture is cooled down to room temperature and phases are separated. The aqueous phase is extracted with ethyl acetate three times and the organic phases combined, dried ($MgSO_4$), filtered and concentrated in vacuo. The residue is triturated from diethyl ether (20 mL) and the product is filtered and dried in vacuo yielding compound 17B as an off-white solid (9.96 g, 57% yield). The mother liquor is concentrated in vacuo and purified by column chromatography (silica gel, gradient 0 to 100% ethyl acetate/isohexane) yielding a further crop (1.79 g, 10% yield). NMR (400 MHz, $CDCl_3$) δ (ppm) 7.78-7.74 (m, 4H), 7.55-7.48 (m, 6H), 4.98 (1, 0.1=4.8 Hz, 2H), 4.29 (m, 2H), 3.03 (t, 0.1=6.4 Hz, 1H).

Compound 18B of Scheme B: 3-Phenyl-4-(2-phenylethynyl)-1H-pyrazol-5-amine

By a similar procedure to that described for the synthesis of compound 16B, compound 18B (5.4 g, 50% yield) is obtained from compound 15B (12.5 g, 41 mmol). $^1$H NMR (400 MHz, $CDCl_3$) δ (ppm) 7.87 (d, J=7.2 Hz, 2H), 7.51-7.43 (m, 4H), 7.42-7.32 (m, 4H), 4.09 (s, 2H).

Compound 19B of Scheme B: 2-(4-Chloro-3,5-diphenyl-1H-pyrazolo[3,4-c]pyridazin-1-yl)acetic acid Sodium nitrite (1.86 g, 26.9 mmol) is added portion-wise to concentrated HCl (30 mL) at 0° C. and stirred for 15 min and then compound 16B (3 g, 8.85 mmol) is added as a solid to the reaction mixture, portion-wise. The suspension is then stirred at RT for 16 h. The reaction mixture is diluted with $CH_2Cl_2$ and washed with water and brine. The organic layer is dried ($MgSO_4$) and concentrated in vacuo. The residue is purified by column chromatography (silica gel, diethyl ether/$CH_2Cl_2$ 1:9) yielding compound 19B as a solid (1.7 g, 53% yield). $^1$H NMR (400 MHz, $CDCl_3$) δ (ppm) 7.80-7.72 (m, 4H), 7.56-7.47 (m, 6H), 5.64 (s, 2H), 2.10 (s, 1H).

Compound 3B of Scheme B: 2-(4-Chloro-3,5-diphenyl-1H-pyrazolo[3,4-c]pyridazin-1-yl)ethan-1-ol Sodium nitrite (4.58 g, 66.3 mmol) is added portion-wise to concentrated HCl (220 mL) at −10° C. and stirred for 10 min. Compound 17B (6.7 g, 22.1 mmol) is added as a solid. The reaction mixture is allowed to warm up, is sonicated for 5 min then stirred at RT for 2 h. The reaction mixture is diluted with $CH_2Cl_2$ and water and the aqueous phase is extracted with $CH_2Cl_2$. The organic phases are combined, dried ($MgSO_4$), filtered and concentrated in sumo. The residue is partially purified by column chromatography (silica gel, gradient 0 to 100% ethyl acetate/isohexane). The resulting residue is triturated from diethyl ether then from ethyl acetate, yielding compound 3B as a solid (900 mg, 12% yield). $^1$H NMR (400 MHz, $CDCl_3$) δ (ppm) 7.79-7.75 (m, 4H), 7.55-7.46 (m, 6H), 4.98 (m, 2H), 4.32-4.25 (m, 2H), 3.04 (t, J=6.4 Hz, 1H), $^{13}$C NMR (100 MHz, $CDCl_3$) d (ppm) 153.09, 151.98, 143.65, 134.48, 130.11, 129.35, 129.33, 129.06, 128.29, 128.17, 127.39, 127.33, 113.70, 60.64, 50.63. LC-MS (analytical method 1: HPLC (Phenomenex Luna 5 μm C18, 100×4.6 mm) with gradient of 5-95% acetonitrile in water (with 0.1% formic acid in each mobile phase)) $R_t$ 4.14 min; m/z 351 [M+H] 99.04% purity.

Compound 21B of Scheme B: N-(1-(2-Hydroxy-2-methylpropyl)-3-phenyl-4-(phenylethynyl)-1H-pyrazol-5-yl)acetamide To a solution of compound 14B (1.0 g, 2.58 mmol) in THF (26 mL) is added methyl magnesium chloride (3 M solution in THF, 3 mL, 9 mmol) at 0° C. The solution obtained is stirred at RT for 3.5 h then successively diluted with ethyl acetate and quenched by addition of 1 M (aq). The aqueous phase is extracted with ethyl acetate, and the combined organic layers are dried ($MgSO_4$) and concentrated in vacuo. The resultant residue is purified using chromatography (silica gel, gradient 0 to 75% ethyl acetate/isohexane) yielding compound 21B as a solid (529 mg, 55% yield). $^1H$ NMR (400 MHz, $CDCl_3$) as a 1.5:1 mixture of compound 21B δ (ppm) 8.11 (dd, J=7.5, 12.3 Hz, 2H), 7.51-7.40 (m, 4H), 7.37-7.31 (m, 4H), 4.15-4.07 (m, 2H), 2.24-2.23 (m, 3H), 1.28 (s, 6H) and N-[2-acetonyl-5-phenyl-4-(2-phenylethynyl)pyrazol-3-yl]acetamide δ (ppm) 8.11 (dd, J=7.5, 12.3 Hz, 2H), 7.51-7.40 (m, 4H), 7.37-7.31 (m, 4H), 4.95 (s, 2H), 2.24-2.23 (m, 3H), 1.28 (s, 6H).

Compound 22B of Scheme B: 1-(5-Amino-3-phenyl-4-(phenylethynyl)-1H-pyrazol-1-yl)-2-methylpropan-2-ol Compound 22B (310 mg, yield 59%) is synthesized from compound 21B (597 mg, 1.6 mmol) following similar procedures outlined in the synthesis of compound 16B. $^1H$ NMR (400 MHz, $CDCl_3$) δ (ppm) 8.11-8.08 (m, 2H), 7.50-7.47 (m, 2H), 7.41 (dd, J=7, 5, 7.5 Hz, 2H), 7.37-7.29 (m, 4H), 4.48 (s, 2H), 4.01 (s, 2H), 2.70 (s, 1H), 1.32-1.31 (m, 6H).

Compound 4B of Scheme B: 1-(4-Chloro-3,5-diphenyl-1H-pyrazolo[3,4-c]pyridazin-1-yl)-2-methylpropan-2-ol To cooled (cooling bath −15° C.) concentrated HCl (9 mL) is added sodium nitrite in one portion (121 mg, 1.75 mmol) and the suspension is left to stir for 10 min after which compound 22B (290 mg, 0.88 mmol) is added. After 5 min, the cooling bath is removed and the reaction mixture is stirred at RT for 3 h. The reaction is cooled again (0° C.) and $CH_2Cl_2$ is added followed by water. The aqueous phase is extracted with $CH_2Cl_2$ and the organic phases are combined, dried ($MgSO_4$), filtered and concentrated in vacuo. Crude material is purified by column chromatography (silica gel, gradient 0 to 50% ethyl acetate/isohexane) yielding compound 4B as orange oil (56 mg), The material obtained is further purified by preparative HPLC, yielding compound 4B as a solid (34 mg, 10% yield). $^1H$ NMR (400 MHz, $CDCl_3$) δ (ppm) 7.81-7.75 (m, 4H), 7.55-7.50 (m, 6H), 4.85 (s, 2H), 3.50 (s, 1H), 1.36 (s, 6H). $^{13}C$ NMR (100 MHz, $CDCl_3$) δ (ppm) 154.36, 152.91, 144.60, 135.42, 130.96, 130.29, 130.28, 129.93, 129.23, 129.07, 128.29, 128.24, 114.16, 71.52, 58.60, 27.26. LCMS (analytical method 1: HPLC (Phenomenex Luna 5 μm C18, 100×4.6 mm) with gradient of 5-95% acetonitrile in water (with 0.1% formic acid in each mobile phase)) $R_t$ 4.49 min; m/z 379 [M+H] 99.71% purity.

Compound 20B of Scheme B: 4-Chloro-3,5-diphenyl-1H-pyrazolo[3,4-c]pyridazine Sodium nitrite (2.88 g, 42 mmol) is added portion-wise to concentrated HCl (314 mL) at −15° C. and stirred for 15 min. Compound 18B (5.4 g, 21 mmol) is added as a solid, followed by the addition of $CH_2Cl_2$ (10 mL). The reaction mixture is allowed to warm up and stirred at RT for 1 h. The reaction mixture is diluted with $CH_2Cl_2$ (44 mL) and NaCl (2.7 g) is added. The reaction mixture is heated to 50° C. for 1 d. The layers are separated and the organic layer is washed with water, dried (phase separator cartridge) and concentrated in vacuo. The residue is purified by column chromatography (silica gel, isohexane/ethyl acetate 4:1, then $CH_2Cl_2$/ethyl acetate 1:0 to 4:1) yielding compound 20B as a solid (3.0 g, 47% yield). $^1H$ NMR (400 MHz, DMSO-$d_6$) δ (ppm) 15.08 (s, 1H), 7.81-7.73 (m, 4H), 7.58-7.51 (m, 6H).

Scheme C

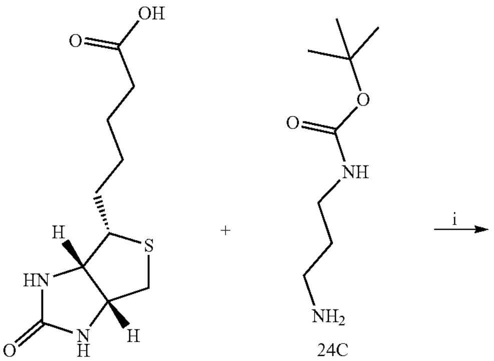

23C 24C

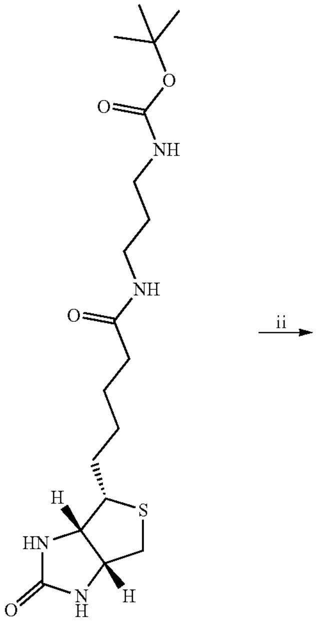

25C

-continued

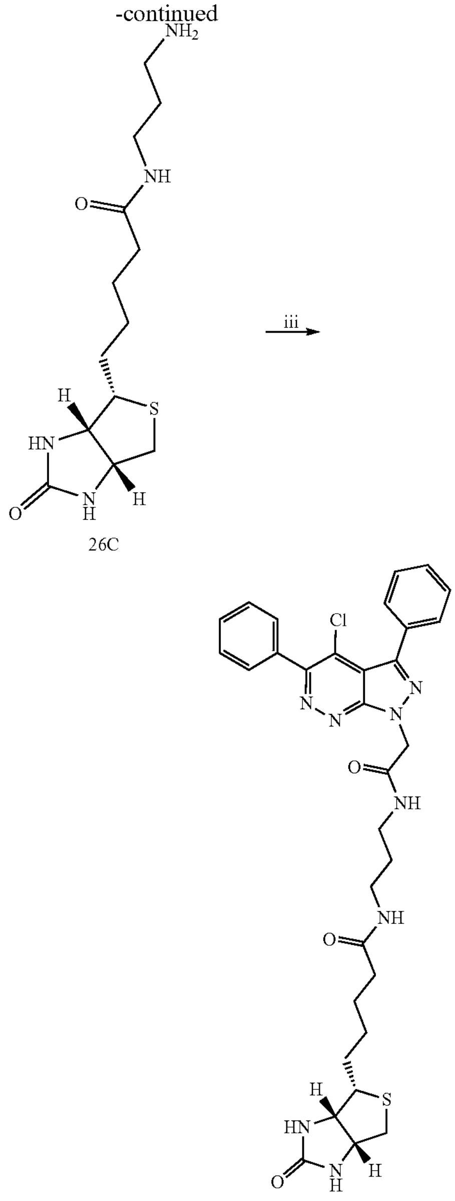

26C

5C (i) HATU, DIPEA, DMF, 25° C.; (ii) TFA, DCM, 25° C.; (iii) compound 19B, HATU, DIPEA, DMF, 25° C.

Scheme C generally describes the preparation of compound 5C.

Compound 25C of Scheme C: tert-Butyl (3-(5-43aS,4S,6aR)-2-oxohexahydro-1H-thieno[3,4-d] imidazol-4-yl)pentanamido)propyl)carbamate To a solution of biotin (23C, 350 mg, 1.43 mmol) in DMF (7.2 mL) are added tert-butyl N-(3-aminopropyl)carbamate (24C, 250 mg, 1.43 mmol), DIPEA (0.375 mL, 2.15 mmol) and HATU (816 mg, 2.15 mmol). The reaction mixture is stirred at RT for 20 h, and then diluted with ethyl acetate and 4% LiCl aqueous solution. The aqueous phase is extracted with ethyl acetate twice, and the combined organic layers are dried ($MgSO_4$) and concentrated in vacuo. The resultant residue is purified using chromatography (silica gel, gradient 0 to 12% 7 M $NH_3$ in $MeOH/CH_2Cl_2$) yielding compound 25C as a solid (180 mg, 31% yield), $^1H$ NMR (400 MHz, DMSO-$d_6$) δ (ppm) 7.75 (t, J=5.2 Hz, 1H), 6.77 (s, 1H), 6.43 (s, 1H), 6.37 (s, 1H), 4.38-4.34 (m, 1H), 4.21-4.16 (m, 1H), 3.23 (d, =5.3 Hz, 1H), 3.16 (dq, J=6.2, 4.3 Hz, 1H), 3.07 (dd, J=6.8, 12.9 Hz, 2H), 2.96 (dd, J=6.6, 13.0 Hz, 2H), 2.88 (dd, J=5.2, 12.4 Hz, 1H), 2.11 (t, J=7.5 Hz, 2H), 1.73-1.62 (m, 1H), 1.61-1.48 (m, 5H), 1.43 (s, 9H), 1.40-1.29 (m, 2H).

Compound 26C of Scheme C: N-(3-Aminopropyl)-5-((3aS,4S,6aR)-2-oxohexahydro-1H-thieno[3,4-d] imidazol-4-yl)pentanamide To a solution of compound 25C (166 mg, 0.415 mmol) in $CH_2Cl_2$ (1 mL) is added TEA (1 mL). The reaction mixture is stirred at RT for 2 h, then concentrated in vacuo. The resultant residue is dissolved in $CH_2Cl_2$ (2 mL) and Biotage MP-carbonate resin (550 mg, 1.66 mmol) is added. The reaction mixture is stirred at RT for 30 min, Beads are filtered off and washed with $CH_2Cl_2$/MeOH (1:1, 2 mL) and the filtrate is concentrated in vacuo to afford compound 26C as a colorless oil (124 mg, 100% yield), which is used as such in the next step.

Compound 5C of Scheme C: N-(3-(2-(4-Chloro-3,5-diphenyl-1H-pyrazolo[3,4-c]pyridazin-1-yl)acetamido)propyl)-5-((3aS,4S,6aR)-2-oxohexahydro-1H-thieno[3,4-d]imidazol-4-yl)pentanamide To a solution of compound 26C (124 mg, 0.415 mmol) in DMF (2 mL) are added compound 19B (151 mg, 0.415 mmol), DIPEA (0.11 mL, 0.62 mmol) and HATU (236 mg, 0.62 mmol). The reaction mixture is stirred at RT for 1.5 h and then diluted with $CH_2Cl_2$ and 4% LiCl aqueous solution. The aqueous phase is extracted with $CH_2Cl_2$ twice, and the combined organic layers are dried (phase separation) and concentrated in vacuo. The resultant residue is first purified by prep HPLC yielding 70 mg, which is further purified by silica gel chromatography, yielding the desired compound 5C as a solid (44 mg, 16% yield). $^1H$ NMR (400 MHz, DMSO-$d_6$) δ (ppm) 8.39 (dd, J=5.7, 5.7 Hz, 1H), 7.87-7.78 (m, 5H), 7.64-7.57 (m, 6H), 6.45 (s, 1H), 6.39 (s, 1H), 5.51 (s, 2H), 4.33 (dd, J=5.3, 7.6 Hz, 1H), 4.18-4.13 (m, 1H), 3.22-3.08 (m, 5H), 2.85 (dd, J=5.2, 12.5 Hz. 1H), 2.61 (d, J=12.4 Hz, 1H), 2.10 (dd, J=7.5, 7.5 Hz, 2H), 1.66-1.48 (m, 6H), 1.39-1.28 (m, 2H). $^{13}C$ NMR (100 MHz, $CDCl_3$) δ (ppm) 172.51, 166.25, 163.16, 154.31, 152.75, 144.06, 135.95, 131.35, 130.58, 130.52, 129.58, 129.44, 129.42, 128.75, 128.70, 114.18, 61.47, 59.64, 55.85, 50.91, 37.21, 36.66, 35.66, 29.64, 28.66, 28.48, 25.75. LCMS (analytical method 1: HPLC (Phenomenex Luna 5 μm C18, 100×4.6 mm) with gradient of 5-95% acetonitrile in water (with 0.1% formic acid in each mobile phase)) $R_t$ 3.52 min; m/z. 647 [M+H] 98.38% purity.

Scheme D

20B

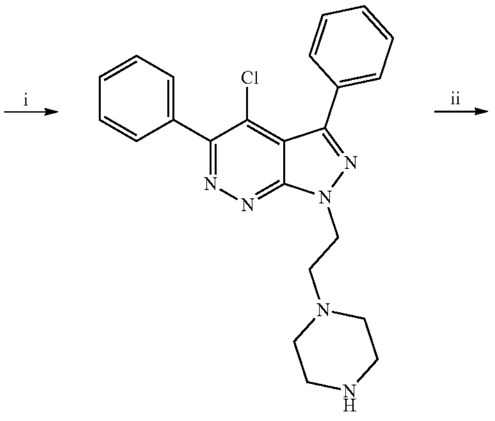

27D

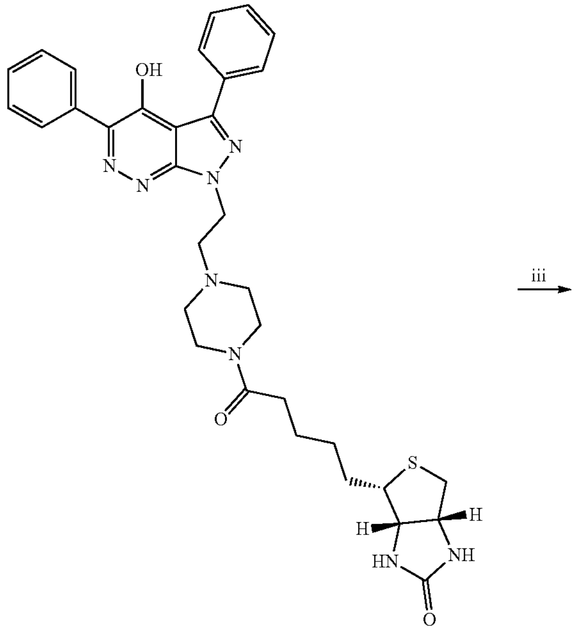

28D

-continued

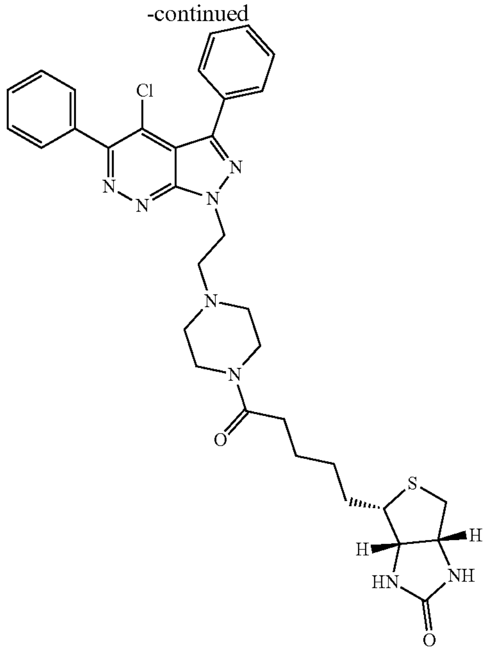

6D (i) (a) 1-tert-Butoxycarbonyl-4-(2-hydroxyethyl)piperazine, DEAD, $PPh_3$, 1,4-dioxane, 120° C., 1 h; (b) HCl in 1,4-dioxane, 25° C.; (ii) (a) HATU, DIPEA, DMF, 25° C.; (b) NaOH, 40° C., 1 h; (iii) $POCl_3$, 25° C.

Scheme D generally describes the preparation of compound 6D.

Compound 27D of Scheme D: 4-Chloro-3,5-diphenyl-1-(2-(piperazin-1-yl)ethyl)-1H-pyrazolo[3,4-c]pyridazine To a mixture of compound 20B (345 mg, 1.13 mmol), 1-tert-butoxycarbonyl-4-(2-hydroxyethyl)piperazine (520 mg, 2.26 mmol) and triphenylphosphine (888 mg, 2.26 mmol) in 1,4-dioxane (8.4 mL) is slowly added to diethyl azodicarboxylate (0.355 mL, 2.26 mmol) at RT. The reaction mixture is then heated using microwave irradiation to 120° C. for 1 h. The reaction mixture is cooled down to RT and 4 M HCl in 1,4-dioxane (4 mL) is added. The reaction mixture is stirred at RT for 4 h, diluted with $CH_2Cl_2$ (10 mL) and the solution is loaded onto a Biotage SCX-2 cartridge (20 g), eluted with methanol, then 7 M $NH_3$ in methanol. Fractions were concentrated in Vacuo to give compound 27D in a 1:1 ratio with 2-hydroxyethyl)piperazine (950 mg, 100% yield) and is used as such in the next step.

Compound 28D of Scheme D: (3aS,4S,6aR)-4-(5-(4-(2-(4-Hydroxy-3,5-diphenyl-1H-pyrazolo[3,4-c]pyridazin-1-yl)ethyl)piperazin-1-yl)-5-oxopentyl)tetrahydro-1H-thieno[3,4-d]imidazol-2(3H)-one To a solution of compound 27D (950 mg crude, 1.13 mmol) in DMF (5.7 mL), DIPEA (0.59 mL, 3.39 mmol), biotin (678 mg, 2.78 mmol) and HATU (1.29 g, 3.39 mmol) are added. The reaction mixture is stirred at RT for 24 h and then diluted with DMSO (5 mL). NaOH (2 M, 5 mL) is added and the reaction mixture is heated to 40° C. for 1 h, then stirred at RT for 2 days. The reaction mixture is purified by preparative HPLC to yield compound 28D (100 mg, 14% yield). $^1$H NMR Compound 60 of Scheme D: (3aS,4S,6aR)-4-(5-((4-(2-(4-Chloro-3,5-diphenyl-1H-pyrazolo[3,4-c]pyridazin-1-yl)ethyl)piperazin-1-yl)-5-oxopentyl)tetrahydro-1H-thieno[3,4-d]imidazol-2(3H)-one A solution of compound 28D (97 mg, 0,155 mmol) in phosphorous oxychloride (6 mL) is stirred at RT for 2 days. The reaction mixture is diluted with $CH_2Cl_2$ and 2 M $Na_2CO_3$ solution. The aqueous phase is extracted twice with $CH_2Cl_2$. Combined organic layers are dried ($MgSO_4$) and concentrated in vacuo. The resultant residue is purified using chromatography (silica gel, gradient 0 to 12% 7 M $NH_3$ in $MeOH/CH_2Cl_2$) yielding compound 60 as a solid (42 mg, 42% yield). $^1H$ NMR (400 MHz, DMSO-$d_6$) δ (ppm) 7.86-7.78 (m, 4H), 7.66-7.56 (m, 6H), 6.47 (s, 1H), 6.39 (s, 1H), 5.01-4.94 (m, 2H), 4.38-4.32 (m, 1H), 4.20-4.15 (m, 1H), 3.17-3.10 (m, 1H), 3.08-3.01 (m, 2H), 2.87 (dd, J=12.4, 5.1 Hz, 1H), 2.63 (d, 0.1=12.4 Hz, 1H), 2.58 (m, 1H), 2.57-2.54 (m, 2H), 2.51 (m, 2H), 2.36-2.28 (m, 2H), 1.71-1.61 (m, 1H), 1.56-1.45 (m, 3H), 1.38 (m, 2H), 1.27-1.17 (m, 1H). $^{13}C$ NMR (100 MHz, $CDCl_3$) δ (ppm) 170.51, 162.70, 153.69, 151.95, 143.18, 135.52, 131.06, 130.15, 130.11, 129.03, 128.94, 128.84, 128.26, 128.20, 113.42, 61.04, 59.76, 59.19, 56.16, 55.48, 52.71, 52.28, 45.27, 32.05, 28.29, 28.11, 24.85. LCMS (analytical method 2: HPLC (Hichrom ACE 3 C18-AR mixed mode column 100×4.6 mm) with gradient of 2-100% acetonitrile in water (with 0.1% formic acid in each mobile phase)) $R_t$ 9.77 min; m/z 645 [M+H] 93.27% purity.

EXAMPLES

Example 1. In Vitro Anti-Cancer Assay of Compound 85

Compound 85 was assessed in 10 human tumor cell lines (see Table 3) for anti-cancer activity in vitro using a Cell-Titer-Blue® based 2D monolayer assay.

CellTiter-Blue® Cell Viability Assay: Tumor cells were grown at 37° C. in a humidified atmosphere with 5% $CO_2$ in RPMI medium, supplemented with 10% (v/v) fetal calf serum and 50 µg/ml gentamicin (140 µl/well). Cultures were incubated at 37° C. and 5% $CO_2$ in a humidified atmosphere. After 24 hours, 10 µl of Compound 85 was added, and left on the cells for another 72 hours (incubation period). Compound 85 was tested at 5 concentrations (0.003 µM, 0.03 µM, 0.3 µM, 3 µM, and 30 µM) and serially diluted in DMSO, mixed with cell culture medium, and added to the assay plates by using a Tecan Freedom EVO 200 robotic platform. The DMSO concentration was kept constant at 0.3% yip across the assay plate. Every 96 well plate included six DMSO-treated control wells and Compound 85-treated wells in duplicate at 5 concentrations. Viability of cells was quantified using the CellTiter-Blue® cell viability assay (Promega G8081). After incubation of cells, the CellTiter-Blue® reagent was brought to ambient temperature. Next, 20 µl of CellTiter-Blue® reagent were added to each well. After incubation tier up to 4 hours, fluorescence (FU) was measured using the EnSpire® multimode plate reader (Perkin Elmer) (excitation λ=600 nm).

Data Evaluation: Sigmoidal concentration-response curves were fitted to the data points (test-versus-control; T/C values) obtained for each tumor model using 4 parameter non-linear curve fit (Charles River DRS Datawarehouse Software). Drug effects are expressed in terms of the percentage of the fluorescence signal, obtained by comparison of the mean signal in the treated wells with the mean signal of the untreated controls (T/C-value [%]) (Table 4). $IC_{50}$ and $IC_{70}$ values were reported as relative and absolute $IC_{50}$ and $IC_{70}$ values (Table 5). The absolute $IC_{50}$ and $IC_{70}$ values reflect the concentration of Compound 85 that achieves T/C=50% and T/C=30%, respectively. The relative $IC_{50}$ value is the concentration of Compound 85 that gives a response half way between the top and bottom plateau of the sigmoidal concentration-response curve (inflection point of the curve).

Compound 85 showed concentration-dependent inhibition of the tumor cell growth in all cell lines of Table 3, with a geometric mean absolute $IC_{50}$ value of 0.95 µM. The curves were very steep and Compound 85 showed fairly similar concentration-response curve in all the cell lines tested, with $IC_{50}$ values ranging from 0.215 µM (CXF LS 174T) to 1.847 µM (PAXF 1657).

TABLE 3

[]Anti-Cancer Activity of Compound 85

| Cell Line | | Tumor type | BRCA mutation |
|---|---|---|---|
| PRXF | PC-3 | Prostate | none |
| PRXF | DU-145 | Prostate | BRCA2 mutation |
| PAXF | HUP-T3 | Pancreas | BRCA2 mutation |
| PAXF | 1657 | Pancreas | none |
| OVXF | A2780 | Ovarian | none |
| OVXF | 899 | Ovarian | BRCA1 mutation |
| CXF | LS 174T | Colon | BRCA1 mutation |
| CXF | HCC-2998 | Colon | none |
| CNXF | U-87 MG | Glioblastoma | none |
| CNXF | 498 | Glioblastoma | none |

TABLE 4

Test-versus-Control Values for []Compound 85 at Different Concentrations

| Cell Line | | Test/Control (%) at Drug Concentration [µM] | | | | |
|---|---|---|---|---|---|---|
| | | 0.003 | 0.03 | 0.3 | 3 | 30 |
| PRXF | PC-3 | 104 | 103 | 103 | 2 | 1 |
| PRXF | DU-145 | 100 | 110 | 102 | 11 | 6 |
| PAXF | HUP-T3 | 100 | 101 | 79 | 16 | 6 |
| PAXF | 1657 | 100 | 100 | 100 | 3 | 1 |
| OVXF | A2780 | 101 | 94 | 101 | 1 | 0 |
| OVXF | 899 | 108 | 106 | 86 | 2 | 1 |
| CXF | LS 174T | 103 | 101 | 35 | 4 | 0 |
| CXF | HCC-2998 | 97 | 100 | 90 | 13 | 1 |
| CNXF | U-87 MG | 99 | 102 | 102 | 1 | 4 |
| CNXF | 498 | 106 | 107 | 113 | 2 | 1 |

TABLE 5

Anti-Cancer Activity of Compound 85

| Cell Line | | Top (%) | Bot. (%) | Unit | Rel. $IC_{50}$ | Rel. $IC_{70}$ | Abs. $IC_{50}$ | Abs. $IC_{70}$ |
|---|---|---|---|---|---|---|---|---|
| PRXF | PC-3 | 103 | 1 | µM | 1.076 | 1.326 | 1.096 | 1.349 |
| PRXF | DU-145 | 105 | 6 | µM | 1.005 | 1.376 | 1.088 | 1.528 |
| PAXF | HUP-T3 | 101 | 0 | µM | 0.785 | 1.505 | 0.794 | 1.518 |
| PAXF | 1657 | 100 | 1 | µM | 1.841 | 2.043 | 1.847 | 2.055 |
| OVXF | A2780 | 99 | 0 | µM | 1.699 | 1.872 | 1.694 | 1.868 |
| OVXF | 899 | 107 | 1 | µM | 0.522 | 0.739 | 0.553 | 0.775 |
| CXF | LS 174T | 103 | 1 | µM | 0.204 | 0.328 | 0.215 | 0.346 |
| CXF | HCC-2998 | 99 | 1 | µM | 1.031 | 1.630 | 1.022 | 1.628 |
| CNXF | U-87 MG | 101 | 3 | µM | 0.935 | 0.987 | 0.940 | 0.994 |
| CNXF | 498 | 109 | 1 | µM | 1.706 | 1.868 | 1.740 | 1.901 |
| Geometric mean IC value [µM]: | | | | | 0.926 | 1.226 | 0.948 | 1.258 |

Example 2. Cell Viability Assay of Compound 85

The CellTiter-Blue® Cell Viability Assay was used to assess the viability of cells from various cancer cell lines, in the presence or absence of Compound 85 (at different concentrations). This assay provides a homogeneous, fluorometric method for estimating the number of viable cells present in multi-well plates. Viable cells retain the ability to reduce resazurin to resorufin, which is highly fluorescent. Nonviable cells rapidly lose metabolic capacity, do not reduce the indicator dye (resazurin) due to the lack of energy in the form of ATP, and thus do not generate a fluorescent signal. The fluorescence produced is proportional to the number of viable cells. There is a linear relationship between cell number and fluorescence.

Cancer cells (see Table 6) were harvested from exponential phase cultures, counted and plated in 96 well flat-bottom microtiter plates, at a cell density 6,000-20,000 cells/well, depending on the cell line's growth rate. The culture medium was supplemented with 10% (v/v) foetal calf serum and 50 μg/mL gentamicin (140 μL/well). Cultures were incubated at 37° C. and 5% $CO_2$ in a humidified atmosphere.

Compound 85 was serially diluted in DMSO, and five Compound 85 concentrations in half-log increments were used: 0.03 μM, 0.09 μM, 0.30 μM, 1.0 μM, and 3.0 μM. After 24 h, 10 μL of Compound 85 (dissolved in DMSO) or control (DMSO) medium were added, in duplicates, and left on the cells for another 72 h. Compound 85 solutions were added to the assay plates using a Tecan Freedom EVO 200 robotic platform. The DMSO concentration was kept constant at 0.3% v/v across the assay plate.

After incubation of up to 72 hours, fluorescence (FU) was measured using the EnSpire® multimode plate reader (Perkin Elmer) (excitation λ=570 nm, emission λ=600 nm).

Cancer cell lines used: Compound 85's anti-cancer effect was tested in 20 human cancer-cell lines representing nine cancer types (Table 6).

TABLE 6

[]Cancer Types and Cell Lines

| Tumour type | Cell line 1 | Cell line 2 |
|---|---|---|
| glioblastoma | CNXF-498 | CNXF-478 MG |
| pancreas | PAXF hup-T3 (BRCA2) | PAXF-1657 |
| prostate | PRXF-du-145b (BRCA2) | PRXF-Pc-3-CDX |
| ovarian | OVXf-A2780 | OVXF-899 (BRCA1) |
| colon | CXF-HCC-2998 | CXF-LS174T (BRCA1, MS) |
| breast | MAXFHER JIMT-1 | MAXFHER BT474 *(BRCA2, SC) |
| | MAXFTN MDA-MB-453 | MAXFTN-401 **(BRCA1, n FS) |
| melanoma | MEXF 1737 | MEXF 1341 (BRCA1/BRCA2, both has FS) |
| soft tissue sarcoma | SXFS 1301 | SXFS-Hs 729 (BRCA1/BRCA2, both has MS) |
| osteosarcoma | SXFO 678L | SXFO Saos-2 |

BRCA = BReast CAncer gene,
MS = missense mutation,
SC = stop codon mutation,
FS = frameshift mutation Results, Results are presented as:

(i) Percentage of viable cells (T/C %).

(ii) Relative and absolute $IC_{50}$ and $IC_{70}$ values, and (iii) Concentration-effect curves/plots for individual cancers.

Percentage of Viable Cells

The percentage of viable cells in the presence of Compound 85 (Test condition, T), at different concentrations, are presented in Table 7 and expressed as a percentage of the number of viable cells in the presence of DMSO without Compound 85 (Control condition, C).

Where T/C percentage is about 100, there is no effect of Compound 85 on the cancer-cell growth. A value below 100% indicates an anti-cancer effect, while a value above 100% indicates enhancement of cancer growth. Small changes in the % are not considered significant. The data show that at concentration of 0.95 μM, Compound 85 has significant anti-cancer activity in 20 human cancer-cell lines representing nine cancer types.

TABLE 7

[]T/C % at Different Concentration of Compound 85

| Cancer | | | Concentration of Compound 85 (μM) | | | | |
|---|---|---|---|---|---|---|---|
| Type | Cell line | | 0.03 | 0.095 | 0.3 | 0.95 | 3.0 |
| Colon | CXF | HCC-2998 | 98 | 99 | 98 | 40 | 22 |
| colon | CXF | LS 174T | 96 | 96 | 72 | 5 | 3 |
| Breast | MAXFHER | BT-474 | 101 | 106 | 99 | 46 | 17 |
| Breast | MAXFHER | JIMT-1 | 97 | 97 | 96 | 30 | 14 |
| Breast | MAXFTN | 401 | 99 | 99 | 87 | 3 | 1 |
| Breast | MAXFTN | MDA-MB-453 | 101 | 97 | 101 | 3 | 1 |
| Melanoma | MEXF | 1341 | 97 | 91 | 82 | 0 | 0 |
| Melanoma | MEXF | 1737 | 99 | 97 | 101 | 27 | 16 |
| Ovarian | OVXF | 899 | 98 | 94 | 65 | 1 | 0 |
| Ovarian | OVXF | A2780 | 102 | 96 | 87 | 0 | 0 |
| Pancreatic | PAXF | 1657 | 97 | 94 | 97 | 66 | 1 |
| Pancreatic | PAXF | HUP-T3 | 95 | 102 | 88 | 21 | 16 |
| Glioblastoma | CNXF | U-87 MG | 99 | 102 | 102 | 1 | 4 |
| Glioblastoma | CNXF | 498 | 106 | 107 | 113 | 2 | 1 |
| Prostate | PRXF | PC-3 | 104 | 103 | 103 | 2 | 1 |
| Prostate | PRXF | DU-145 | 100 | 110 | 102 | 11 | 6 |
| Soft tissues Sarcoma | SXFS | 1301 | 105 | 106 | 102 | 3 | 2 |
| Soft tissues Sarcoma | SXFS- | Hs 729 | 99 | 99 | 99 | 13 | 7 |
| Osteosarcoma | SXFO | 678 | 101 | 97 | 91 | 2 | 1 |
| Osteosarcoma | SXFO | Saos-2 | 97 | 93 | 99 | 1 | 0 |

Relative and Absolute $IC_{50}$ and $IC_{70}$ Values

The relative $IC_{50}$ is determined as the Compound 85 concentration giving a response halfway between the maximum cell viability signal (i.e., a 100% cell viability, no Compound 85 response) and the minimal viability signal (i.e. maximum cell viability inhibition achieved by Compound 85), in a sigmoidal concentration-effect curve.

The absolute $IC_{50}$ is determined as the concentration that is associated with a T/C ratio of 50%.

Table 8, below, shows values for absolute and relative $IC_{50}$ and $IC_{70}$ in different human cancer cell lines. The geometric means for relative and absolute $IC_{50}$ values were 0.583 μM and 0.596 μM, respectively. It is accepted that for most anti-cancer therapeutics a mean $IC_{50}$ of <1.0 μM indicates a cancer cell line that is sensitive to the therapy. The Geometric means for relative and absolute $IC_{70}$ values were 0.675 and 0.712 μM, respectively,

TABLE 8

| []Absolute and relative $IC_{50}$ and $IC_{70}$ values (μM) of Compound 85 in different human cancer cell lines | | | | | | |
|---|---|---|---|---|---|---|
| Cancer Type | Cell line | | Relative $IC_{50}$ | Relative $IC_{70}$ | Absolute $IC_{50}$ | Absolute $IC_{70}$ |
| Colon | CXF | HCC-2998 | 0.765 | 0.891 | 0.844 | 1.125 |
| Colon | CXF | LS 174T | 0.384 | 0.467 | 0.383 | 0.474 |
| Breast | MAXFHER | BT-474 | 0.766 | 1.01 | 0.886 | 1.316 |
| Breast | MAXFHER | JIMT-1 | 0.702 | 0.844 | 0.742 | 0.957 |
| Breast | MAXFTN | 401 | 0.429 | 0.5 | 0.429 | 0.503 |
| Breast | MAXFTN | MDA-MB-453 | 0.717 | 0.763 | 0.719 | 0.765 |
| Melanoma | MEXF | 1341 | 0.399 | 0.451 | 0.391 | 0.445 |
| Melanoma | MEXF | 1737 | 0.799 | 0.864 | 0.826 | 0.925 |
| Ovarian | OVXF | 899 | 0.352 | 0.423 | 0.346 | 0.418 |
| Ovarian | OVXF | A2780 | 0.406 | 0.463 | 0.405 | 0.463 |
| Pancreatic | PAXF | 1657 | 1.049 | 1.169 | 1.041 | 1.166 |
| Pancreatic | PAXF | HUP-T3 | 0.487 | 0.602 | 0.532 | 0.723 |
| Osteosarcoma | SXFO | 678 | 0.458 | 0.531 | 0.458 | 0.532 |
| Osteosarcoma | SXFO | Saos-2 | 0.712 | 0.75 | 0.709 | 0.747 |
| Soft tissue sarcoma | SXFS | 1301 | 0.49 | 0.558 | 0.501 | 0.57 |
| Soft tissue sarcoma | SXFS | Hs 729 | 0.724 | 0.789 | 0.733 | 0.808 |
| Prostate | PRXF | PC-3 | 1.07585 | 1.32629 | 1.09606 | 1.34929 |
| Prostate | PRXF | DU-145 | 1.0054 | 1.37576 | 1.0883 | 1.52792 |
| Glioblastoma | CNXF | U-87 MG | 0.93519 | 0.98695 | 0.93966 | 0.99376 |
| Glioblastoma | CNXF | 498 | 1.70611 | 1.86824 | 1.74025 | 1.90105 |

Compound 85 showed concentration dependent anti-cancer activity in all of the 20 human cancer cell lines tested, with an absolute geometric mean $IC_{50}$ value of 0.6 μM. Individual absolute $IC_{50}$ values were in the range of 0.35 μM and 1.0 μM, indicating that Compound 85 has significant anti-cancer activity.

INCORPORATION BY REFERENCE

Each reference disclosed in this application is incorporated by reference herein in its entirety.

What is claimed is:

1. A method for treating cancer, comprising administering to a subject in need thereof an effective amount of a compound having the structure

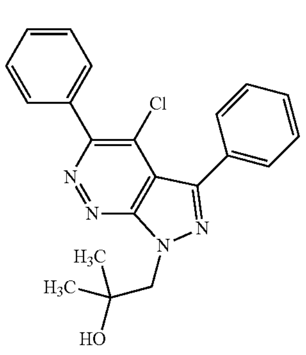 [SMILES: CC(C)(O)Cn1nc(-c2ccccc2)c2c(Cl)c(-c3ccccc3)nnc21]

or a pharmaceutically acceptable salt thereof, wherein the cancer is colorectal cancer, glioblastoma, lung cancer, ovarian cancer, pancreatic cancer, cervical cancer, prostate cancer, breast cancer, gastric cancer, head and neck cancer, liver cancer, melanoma, lymphopoietic cancer, hematopoietic cancer, soft tissue sarcoma, or osteosarcoma.

2. The method of claim 1, wherein the cancer has one or more disease-associated mutations in BRCA1 or BRCA2.

3. The method of claim 1, wherein the cancer has one or more disease-associated mutations in BRCA1 and one or more disease-associated mutations in BRCA2.

4. The method of claim 1, wherein the cancer has one or more disease-associated mutations in BRCA1 but harbors no disease-associated mutations in BRCA2.

5. The method of claim 1, wherein the cancer has one or more disease-associated mutations in BRCA2 but harbors no disease-associated mutations in BRCA1.

6. The method of claim 1, wherein the cancer has no disease-associated mutations in BRCA1 or BRCA2.

7. The method of claim 1, wherein the cancer is BRCA-driven cancer.

8. The method of claim 1, wherein the cancer is BRCA1-driven cancer.

9. The method of claim 1, wherein the cancer is BRCA2-driven cancer.

10. The method of claim 1, wherein the cancer is BRCA1- and BRCA2-driven cancer.

11. The method of claim 1, wherein the cancer is neither BRCA1-nor BRCA2 driven cancer.

12. The method of any one of claims 1 and 2-11, wherein the method further comprises administering an anti-cancer therapy to the subject.

13. The method of claim 12, wherein the anti-cancer therapy is neoadjuvant therapy or an adjuvant therapy.

14. The method of claim 12, wherein the anti-cancer therapy is chemotherapy, targeted therapy, hormone therapy, immunotherapy, T-cell therapy, or stem cell therapy.

15. A method for treating or preventing an inflammatory disease or treating an autoimmune disease, comprising administering to a subject in need thereof an effective amount of a compound having the structure

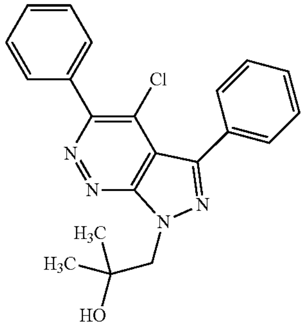 [SMILES: CC(C)(O)Cn1nc(-c2ccccc2)c2c(Cl)c(-c3ccccc3)nnc21]

or a pharmaceutically acceptable salt thereof.

16. The method of claim 15, wherein the inflammatory disease is atherosclerosis, cardiac myopathy, epidermolysis bullosa, asthma, psoriasis, or inflammatory bowel disease, and the autoimmune disease is rheumatoid arthritis, juvenile idiopathic arthritis, celiac disease, dermatitis herpetiformis, autoimmune blistering skin disease, type 1 diabetes, dermatomyositis, alopecia areata, antiphospholipid antibody syndrome, autoimmune hepatitis, multiple sclerosis, Guillain-Barre syndrome, demyelinating polyneuropathy, Graves's disease, Hashimoto's thyroiditis, myasthenia gravis, vasculitis, hemolytic anemia, idiopathic thrombocytopeniapurpura, inflammatory myopathy, primary biliary cirrhosis, scleroderma, Sjögren's syndrome, systemic lupus erythematosus, or vitiligo.

17. The method of claim 16, wherein the inflammatory disease is inflammatory bowel disease, and the inflammatory bowel disease is colitis or Crohn's disease.

18. The method of claim 13, wherein the neoadjuvant therapy or the adjuvant therapy is chemotherapy, targeted therapy, hormone therapy, immunotherapy, T-cell therapy, or stem cell therapy.

19. The method of claim 1, wherein the subject is a human.

20. The method of any one of claims 15, 16, and 17 wherein the subject is a human.

21. The method of claim 19, comprising administering to the subject in need thereof an effective amount of a compound having the structure

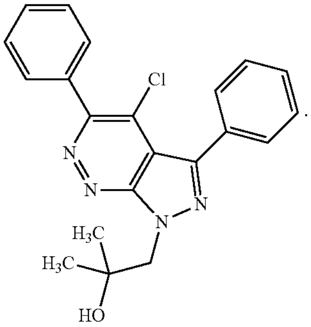 [SMILES: CC(C)(O)Cn1nc(-c2ccccc2)c2c(Cl)c(-c3ccccc3)nnc21]

22. The method of claim 20, comprising administering to the subject in need thereof an effective amount of a compound having the structure

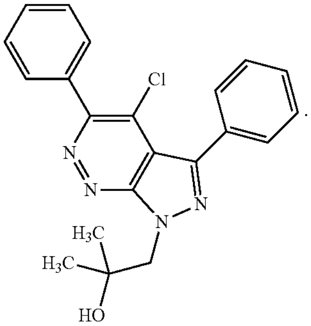 [SMILES: CC(C)(O)Cn1nc(-c2ccccc2)c2c(Cl)c(-c3ccccc3)nnc21]

* * * * *